(12) United States Patent
Patton et al.

(10) Patent No.: US 9,932,479 B2
(45) Date of Patent: Apr. 3, 2018

(54) DYES AND COMPOSITIONS, AND PROCESSES FOR USING SAME IN ANALYSIS OF PROTEIN AGGREGATION AND OTHER APPLICATIONS

(71) Applicant: Enzo Biochem, Inc., New York, NY (US)

(72) Inventors: Wayne Forrest Patton, Dix Hills, NY (US); Sergiy M. Yarmoluk, Kyiv (UA); Praveen Pande, Holbrook, NY (US); Vladyslava Kovalska, Kyiv (UA); Lijun Dai, Farmingville, NY (US); Kateryna Volkova, Kyiv (UA); Jack Coleman, East Northport, NY (US); Mykhaylo Losytskyy, Kyiv (UA); Anthony Ludlum, Ypsilanti, MI (US); Anatoliy Balanda, Kyiv (UA)

(73) Assignee: Enzo Biochem, Inc., Farmingdale, NY (US)

( * ) Notice: Subject to any disclaimer, the term of this patent is extended or adjusted under 35 U.S.C. 154(b) by 325 days.

(21) Appl. No.: 14/812,171

(22) Filed: Jul. 29, 2015

(65) Prior Publication Data
US 2015/0376411 A1 Dec. 31, 2015

Related U.S. Application Data

(62) Division of application No. 12/592,639, filed on Nov. 30, 2009, now Pat. No. 9,133,343.

(51) Int. Cl.
| | | |
|---|---|---|
| *C09B 23/16* | (2006.01) | |
| *C09B 23/14* | (2006.01) | |
| *G01N 33/58* | (2006.01) | |
| *G01N 33/68* | (2006.01) | |
| *C07D 401/12* | (2006.01) | |
| *C09B 23/01* | (2006.01) | |
| *C09B 23/04* | (2006.01) | |
| *C09B 23/06* | (2006.01) | |
| *C09B 23/10* | (2006.01) | |
| *C12Q 1/68* | (2018.01) | |

(52) U.S. Cl.
CPC .......... *C09B 23/145* (2013.01); *C07D 401/12* (2013.01); *C09B 23/0008* (2013.01); *C09B 23/0025* (2013.01); *C09B 23/0058* (2013.01); *C09B 23/0066* (2013.01); *C09B 23/04* (2013.01); *C09B 23/06* (2013.01); *C09B 23/102* (2013.01); *C09B 23/141* (2013.01); *G01N 33/582* (2013.01); *G01N 33/6845* (2013.01); *G01N 2458/30* (2013.01); *G01N 2800/2821* (2013.01); *G01N 2800/2835* (2013.01)

(58) Field of Classification Search
CPC .................................................. C09B 23/145
USPC .......................................... 546/165; 435/6.1
See application file for complete search history.

(56) References Cited

U.S. PATENT DOCUMENTS

| | | |
|---|---|---|
| 4,256,458 A | 3/1981 | Degen |
| 4,868,103 A | 9/1989 | Stavrianopoulos et al. |
| 4,925,770 A | 5/1990 | Ichimura |
| 5,118,801 A | 6/1992 | Lizardi et al. |
| 5,192,737 A | 3/1993 | Kubodera et al. |
| 5,210,015 A | 5/1993 | Gelfand et al. |
| 5,401,847 A | 3/1995 | Glazer et al. |
| 5,538,848 A | 7/1996 | Livak et al. |
| 5,580,990 A | 12/1996 | Van Den Berg et al. |
| 5,646,264 A | 7/1997 | Glazer et al. |
| 5,800,996 A | 9/1998 | Lee et al. |
| 5,925,517 A | 7/1999 | Tyagi et al. |
| 5,994,056 A | 11/1999 | Higuchi et al. |
| 6,008,373 A | 12/1999 | Waggoner et al. |
| 6,020,141 A | 2/2000 | Pantoliano et al. |
| 6,174,670 B1 | 1/2001 | Wittwer et al. |
| 6,593,465 B1 | 7/2003 | Wolff et al. |
| 6,685,940 B2 | 2/2004 | Andya et al. |
| 6,737,401 B2 | 5/2004 | Kim et al. |
| 6,977,142 B2 | 12/2005 | Huang et al. |
| 2003/0225247 A1 | 12/2003 | Stavrianopoulos et al. |
| 2005/0137388 A1 | 6/2005 | Rabbani et al. |
| 2008/0125361 A1 | 5/2008 | Ludvigsen et al. |

FOREIGN PATENT DOCUMENTS

| | | |
|---|---|---|
| CH | 648859 | 4/1985 |
| DE | 3136259 | 3/1983 |
| FR | 2912140 | 8/2008 |
| GB | 2 011 457 | 7/1979 |
| WO | WO2007/110538 | 10/2007 |
| WO | WO2007/110542 | 10/2007 |
| WO | WO2009/109457 | 9/2009 |

OTHER PUBLICATIONS

Demeule et al., Detection and characterization of protein aggregates by fluorescence microscopy, Intl. J. Pharmaceutics 2007, 37-45.
Kovalska et al., Fluorescent homodimer styrylcyanines: synthesis and spectral-luminescent studies in nucleic acids and protein complexes, Dyes and Pigments 2005, 47-54, 67.
Kovalska et al.. Studies on the spectral-luminescent properties of the novel homodimer styryl dyes in complexes with DNA, Journal of Fluorescence 2005, 215-219, 15.
Arakawa et al., Aggregation Analysis of Therapeutic Proteins, Part 1, BioProcess International 2006, 32-42, 4.
Arakawa et al., Aggregation Analysis of Therapeutic Proteins, Part 2, BioProcess International 2007, 38-47, 5.
Arakawa et al., Aggregation Analysis of Therapeutic Proteins, Part 3, BioProcess International 2007, 52-70, 5.

(Continued)

*Primary Examiner* — Jezia Riley
(74) *Attorney, Agent, or Firm* — Paul Diamond, Esq.

(57) ABSTRACT

Provided are dyes and compositions which are useful in a number of applications, such as the detection and monitoring protein aggregation, kinetic studies of protein aggregation, neurofibrillary plaques analysis, evaluation of protein formulation stability, protein thermal stability shift assay and analysis of molecular chaperone activity. These dyes and compositions are also useful as probes in nucleic acid and protein detection.

7 Claims, 46 Drawing Sheets

(56) References Cited

OTHER PUBLICATIONS

Capelle et al., A High Throuhput Protein Formulation Platform: Case Study of Salmon Calcitonin, Pharmaceutical Research 2009, 118-128, 26.

Demeule et al.. Detection and characterization of protein aggregates by fluorescence microscopy, International Journal of Pharmaceutics 2007, 37-45, 329.

Ericsson et al., Thermofluor-based high-throughput stability optimization of proteins for structural studies, Analytical Biochemistry 2006, 289-298, 357.

Ferrari et al., The protein disulphide-isomerase family : unravelling a string of folds, Biochem. J. 1999, 1-10, 339.

Garcia-Mata et al., Hassles with Taking Out the Garbage: Aggravating Aggresomes, Traffic 2002; 388-396, 3.

Hawe et al., Extrinsic Fluorescent Dyes as Tools for Protein Characterization, Pharmaceutical Research, 2008, 1487-1499, 25.

Khurana, et al., Is Congo Red an Amyloid-specific Dye?, The Journal of Biological Chemistry 2001, 22715-22721, 276.

Klunk et al., Chrysamine-G, a Lipophilic Analogue of Congo Red, Inhibits A Beta-Induced Toxicity in PC12 Cells, Life Sciences, 1998, 1807-1814, 63.

Krishnamurthy et al., Emerging Analytical Technologies for Biotherapeutics Development, BioProcess International 2008, 32-34, 6.

Kumar et al., Suppression of lysozyme aggregation at alkaline pH by tri-N-acetylchitotriose, Biochimica et Biophysica Acta 2009, 913-920, 1794.

Li et al., Delta 12-Prostaglandin J2 inhibits the ubiquitin hydrolase UCH-L1 and elicits ubiquitin-protein aggregation without proteasome inhibition, Biochemical and Biophysical Research Communications 2004, 1171-1180, 319.

Lindgren et al., Detection and Characterization of Aggregates, Prefibrillar Amyloidogenic Oligomers, and Protofibrils Using Fluorescence Spectroscopy, Biophysical Journal 2005, 4200-4212, 88.

Lundstrom et al., Protein Disulfide-Isomerase Is a Substrate for Thioredoxin Reductase and Has Thioredoxin-like Activity, The Journal of Biological Chemistry, 1990, 9114-9120, 265.

Lyles et al., Catalysis of the Oxidative Folding of Ribonuclease A by Protein Disulfide Isomerase: Dependence of the Rate on the Composition of the Redox Buffer, Biochemistry 1991, 613-619, 30.

Matulis et al., Thermodynamic Stability of Carbonic Anhydrase: Measurements of Binding Affinity and Stoichiometry Using ThermoFluor, Biochemistry 2005, 5258-5266, 44.

Mezzasalma et al., Enhancing Recombinant Protein Quality and Yield by Protein Stability Profiling, Journal of Biomolecular Screening 2007,418-428, 12.

Morris et al., Protein aggregation kinetics, mechanism, and curve-fitting: A review of the literataure, Biochemica et Biophysica Acta 2009, 375-397, 1794.

Murakamai et al., Neurotoxicity and Physiochemical Properties of A Beta Mutant Peptides from Cerebral Amyloid Angiopathy, The Journal of Biological Chemistry 2003, 46179-46187, 278.

Puig et al., Protein Disulfide Isomerase Exhibits Chaperone and Anti-chaperone Activity in the Oxidative Refolding of Lysozyme, The Journal of Biological Chemistry, 1994, 7764-7771, 269.

Raibekas, Andrei A., Estimation of protein aggregation propensity with a melting point apparatus, Analytical Biochemistry 2008; 331-332, 380.

Raturi et al., Characterization of redox state and reductase activity of protein disulfide isomerase under different redox environments using a sensitive fluorescent assay, Free Radical Biology & Medicine 2007, 62-70, 43.

Smith et al., A High-Throughput Turbidometric Assay for Screening Inhibitors of Protein Disulfide Isomerase Activity, Journal of Biomolecular Screening 2004, 614-620, 9.

Stefani, Massimo, Protein misfolding and aggregation: new examples in medicine and biology of the dark side of the protein world, Biochimica et Biophysica Acta 2004, 5-25, 1739.

Stefani et al., Protein aggregation and aggregate toxicity: new insights into protein folding, misfolding diseases and biological evolution, J Mol Med 2003, 678-699, 81.

Todd et al., Affinity assays for decrypting protein targets of unknown function, Drug Discovery Today: Technologies, 2005, 267-273, 2.

Van Raaij et al., Quantitative Morphological Analysis Reveals Ultrastructural Diversity of Amyloid Fibrils from Alpha-Synuclein Mutants, Biophysical Journal: Biophysical Letters, 2006, L96-L98, 91.

Volkova et al., Cyanine dye-protein interactions: Looking for fluorescent probes for amyloid structures, J. Biochem. Biophys. Methods 2007, 727-733, 70.

Volkova et al., Specific fluorescent detection of fibrillar alpha-synuclein using mono- and trimethine cyanine dyes, Bioorganic & Medicinal Chemistry 2008, 1452-1459, 16.

Volkova et al., Explorations of the application of cyanine dyes for quantitative alpha-synuclein detection, Biotechnic & Histochemistry 2009, 55-61, 84.

Bondos et al., "Detection and prevention of protein aggregation before, during, and after purification," *Analytical Biochemistry*, vol. 316, pp. 223-231 (2003).

Nizomov et al., "Spectral-luminescent study of the interaction of some styrylcyanine dyes with bovine serum albumin and DNA in acqueous solutions," *Journal of Molecular Structure*, vol. 906, pp. 199-205 (2009).

Yashchuk et al., Proceedings of SPIE—The International Society for Optical Engineering, 2007, 6996, Pt. 1—Photonics North; 67960M/1-67960M/14 (abstract only).

Kawaguchi et al., "The Deacetylase HDAC6 Regulates Aggresome Formation and Cell Viability in Response to Misfolded Protein Stress," *Cell*, vol. 118, pp. 727-738 (2003).

Figure 1A

| Dye | Dye Alone: $\lambda_{Ex}$ (nm) | Dye Alone: $\lambda_{Em}$ (nm) | Dye with Aggregate: $\lambda_{Ex}$ (nm) | Dye with Aggregate: $\lambda_{Em}$ (nm) | Fluorescence $I_{dye}$ | Fluorescence $I_{Mono}$ | Fluorescence $I_{Agg}$ | $I_{Agg}/I_{Mono}$ |
|---|---|---|---|---|---|---|---|---|
| S25 | 485 | 613 | 516 | 607 | 3.4 | 4.6 | 87.3 | 19.0 |
| S43 | 527 | 637 | 550 | 623 | 0.35 | 0.58 | 27.3 | 47 |
| TOL3 | 471 | 611 | 511 | 603 | 2.7 | 2.7 | 40.2 | 14.9 |
| Yat 2134 | 500 | 620 | 535 | 613 | 4.2 | 4.9 | 63.2 | 12.9 |
| Yat 2148 | 520 | 632 | 553 | 625 | 1.2 | 3.4 | 53 | 15.6 |
| Yat 2149 | 502 | 614 | 534 | 617 | 0.6 | 0.7 | 29.5 | 42 |
| Yat 2150 | 485 | 612 | 515 | 610 | 6.7 | 9.7 | 42.3 | 4.4 |
| F | 460 | 610 | 518 | 607 | 3.6 | 3.4 | 57.4 | 16.9 |
| L-33 | 465 | 527 | 462 | 504 | 7.7 | 7.6 | 53 | 7.0 |
| S49 | 501 | 584 | 524 | 576 | 2.2 | 2.2 | 20.1 | 9.1 |
| S33 | 479 | 616 | 513 | 611 | 5.5 | 5.7 | 19.4 | 3.4 |
| TOL-11 | 389 | 539 | 554 | 603 | 10 | 6.5 | 22.5 | 3.5 |
| SL-2131 | 491 | 578 | 516 | 578 | 7.4 | 7.5 | 30.3 | 4.1 |
| SL-2592 | 401 | 608 | 400 | 608 | 7.5 | 8 | 25.4 | 7.5 |

Figure 1A (cont'd)

| Dye | Dye Alone: $\lambda_{Ex}$ (nm) | Dye Alone: $\lambda_{Em}$ (nm) | Dye with Aggregate: $\lambda_{Ex}$ (nm) | Dye with Aggregate: $\lambda_{Em}$ (nm) | Fluorescence $I_{dye}$ | Fluorescence $I_{Mono}$ | Fluorescence $I_{Agg}$ | $I_{Agg}/I_{Mono}$ |
|---|---|---|---|---|---|---|---|---|
| Tio-1 | 494 | 578 | 526 | 578 | 2.8 | 2.8 | 19 | 6.8 |
| S-13 | 568 | 662 | 580 | 670 | 0.2 | 0.2 | 3.1 | 15.5 |
| L-30 | 457 | 515 | 478 | 512 | 1.5 | 1.8 | 8 | 4.4 |
| YA-1 | 446 | 491 | 461 | 498 | 7.7 | 11 | 45 | 4.1 |
| YA-3 (Diph40) | 460 | 514 | 456 | 537 | 6.4 | 7.9 | 24.2 | 3.1 |
| TOL-2 [T-33] | 527 | 595 | 566 | 600 | 0.5 | 0.5 | 3.5 | 7 |
| TOL-5 | 428 | 581 | 460 | 535 | 3.8 | 4.5 | 22.2 | 4.9 |
| Dil-10 [TOL-7] | 548 | 595 | 564 | 599 | 3.7 | 3.6 | 15.3 | 4.3 |
| S-39 | 540 | 599 | 577 | 605 | 3.1 | 3.3 | 11.3 | 3.4 |
| Fm [b] | 461 | 610 | 504 | 597 | 5.5 | 5.5 | 21 | 3.8 |
| S-42 | 547 | 600 | 559 | 603 | 1.1 | 1.1 | 5 | 4.5 |
| S-48 | 491 | 581 | 527 | 588 | 2.3 | 2.3 | 15.8 | 6.9 |
| TOL-6 | 501 | 559 | 512 | 559 | 4.6 | 4.6 | 17.5 | 3.8 |
| Lu-1 | 453 | 583 | 452 | 526 | 7.3 | 7.6 | 24 | 3.2 |
| Lu-2 | 473 | 506 | 485 | 503 | 3.8 | 3 | 14 | 4.7 |

Figure 1A (cont'd)

| Dye | Dye Alone: $\lambda_{Ex}$ (nm) | Dye Alone: $\lambda_{Em}$ (nm) | Dye with Aggregate: $\lambda_{Ex}$ (nm) | Dye with Aggregate: $\lambda_{Em}$ (nm) | Fluorescence $I_{dye}$ | Fluorescence $I_{Mono}$ | Fluorescence $I_{Agg}$ | $I_{Agg}/I_{Mono}$ |
|---|---|---|---|---|---|---|---|---|
| Yat2135 | 500 | 618 | 540 | 620 | 0.9 | 0.7 | 12.5 | 17.9 |
| Yat2214 | 507 | 626 | 549 | 625 | 1.5 | 1.4 | 6.4 | 4.6 |
| Yat2213 | 483 | 622 | 540 | 622 | 0.6 | 1.2 | 5.5 | 4.6 |
| D-95 | 450 | 585 | 555 | 598 | 0.6 | 1 | 8.4 | 8.4 |
| D-97 | 516 | 650 | 587 | 650 | 3.6 | 3.7 | 13.4 | 3.6 |
| S-8 | 547 | 671 | 566 | 667 | 0.8 | 0.8 | 2.8 | 3.5 |
| Yat2324 | 500 | 619 | 551 | 619 | 0.8 | 0.7 | 7.1 | 10.1 |
| S-22 | 543 | 598 | 562 | 602 | 0.5 | 0.8 | 2.4 | 3.0 |

Figure 1B

| Dye | Structure |
|---|---|
| S25 | 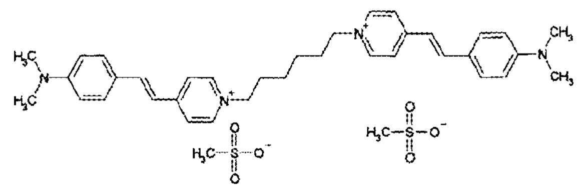 |
| S43 | 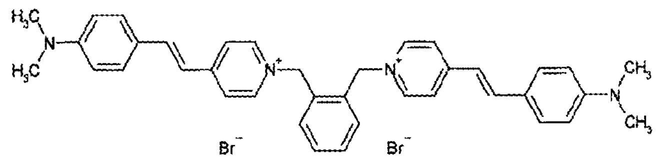 |
| TOL3 | 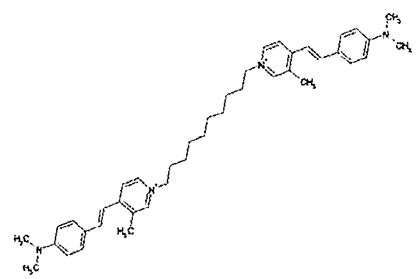 |
| Yat 2134 | 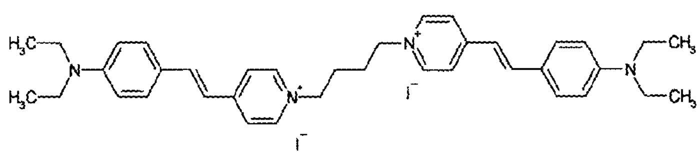 |
| Yat 2148 | 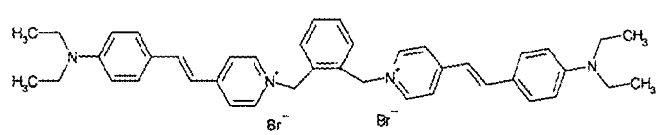 |
| Yat 2149 | 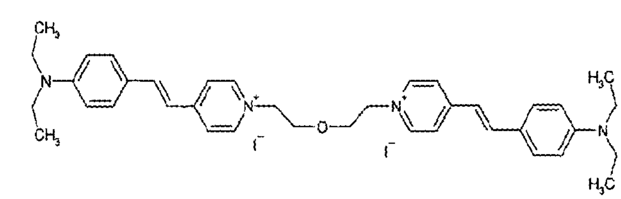 |

Figure 1B (cont'd)

| Dye | Structure |
|---|---|
| Yat 2150 | (chemical structure) |
| F | (chemical structure) |
| L-33 | (chemical structure) |
| S49 | (chemical structure) |
| S-33 | (chemical structure) |

Figure 1B (cont'd)

| Dye | Structure |
|---|---|
| TOL-11 | 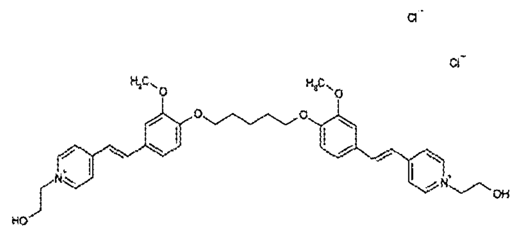 |
| S-22 | 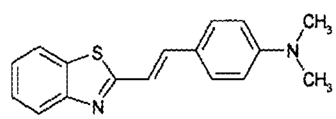 |
| SL-2131 | 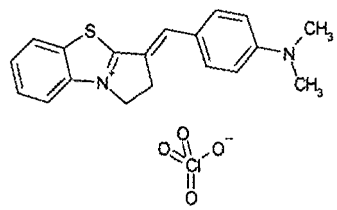 |
| SL-2592 | 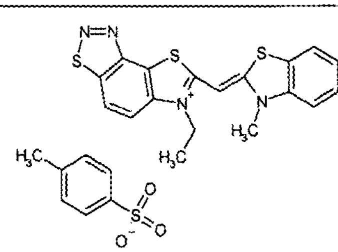 |
| Tio-1 | 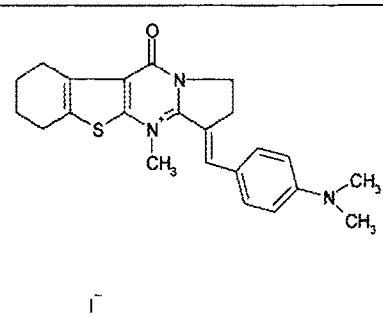 |

Figure 1B (cont'd)

| Dye | Structure |
|---|---|
| S-13 | 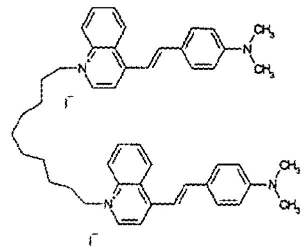 |
| L-30 | 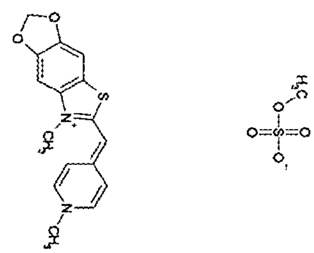 |
| YA-1 | 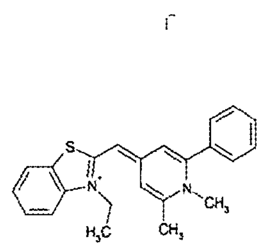 |
| YA-3 (Diph40) | 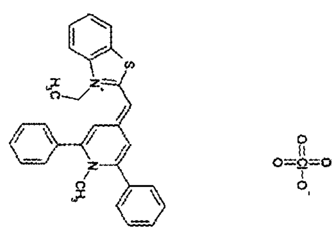 |
| TOL-2 [T-33] | 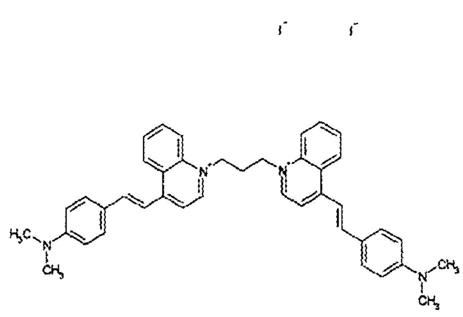 |

| Dye | Structure |
|---|---|
| TOL-5 | 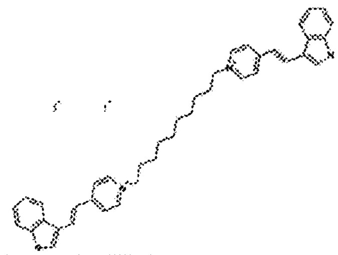 |
| DiI-10 [TOL-7] | 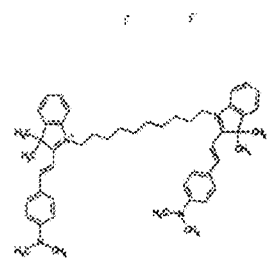 |
| S-39 | 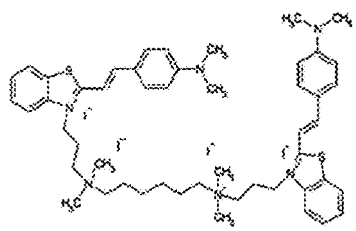 |
| Fm [b] | 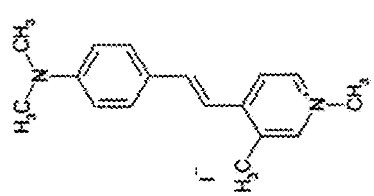 |
| S-42 | 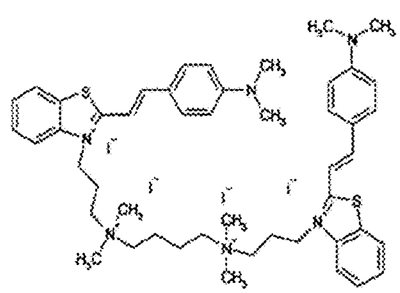 |

| Dye | Structure |
|---|---|
| S-48 | 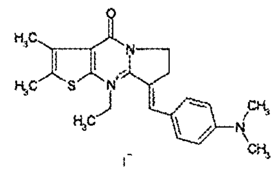 |
| TOL-6 | 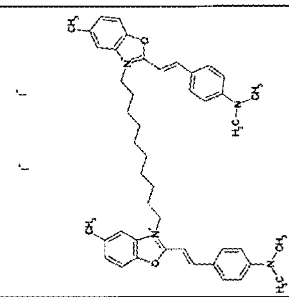 |
| Lu-1 | 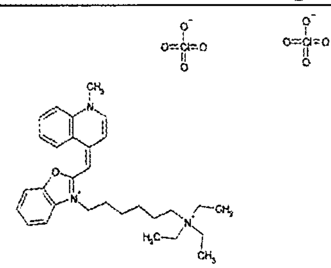 |
| Lu-2 | 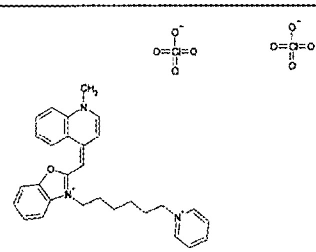 |
| Yat-2135 | 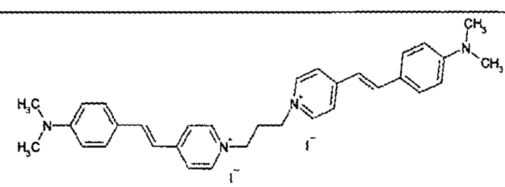 |
| Yat-2214 | 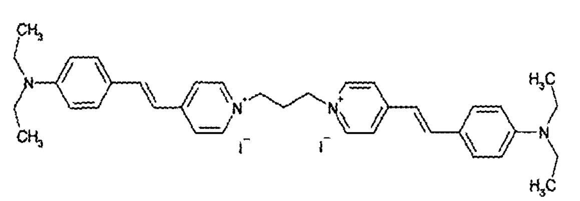 |

Figure 1B (cont'd)

| Dye | Structure |
|---|---|
| Yat-2213 | (structure shown) |
| D-95 | (structure shown) |
| D-97 | (structure shown) |
| S-8 | (structure shown) |
| Yat2324 | (structure shown) |

Figure 2A

| Dye | Dye alone: Excitation wavelength (nm) | Dye alone: Emission wavelength (nm) | Dye with aggregate: Excitation wavelength (nm) | Dye with aggregate: Emission wavelength (nm) | Fluorescence enhancement: Aggregate/ monomer |
|---|---|---|---|---|---|
| S-11 | 531 | 594 | 560 | 600 | 2.6 |
| S-12 | 539 | 597 | 553 | 599 | 2.2 |
| SH-330 | 393 | 278 | 398 | 483 | 1.6 |
| SH-654 | 370 | 443 | 359 | 434 | 0.91 |
| SH-675 | 445 | 472 | 449 | 475 | 1.8 |
| SH-975 | 471 | 631 | 471 | 630 | 1.8 |
| SH-1036 | 478 | 611 | 464 | 605 | 2.7 |
| SI-2599 | 468 | 564 | 468 | 569 | 1.1 |
| SI-2600 | 518 | 535 | 518 | 536 | 1.9 |
| S-7 | 460 | 612 | 465 | 609 | 1.1 |
| L-28 | 460 | 654 | 572 | 577 | 1.4 |
| L-31 | 450 | 527 | 462 | 534 | 2.7 |
| TOL-4 | 488 | 665 | 458 | 654 | 1.4 |
| TOL-10 | 394 | 544 | 397 | 539 | 1.4 |
| S-26 | 532 | 593 | 562 | 602 | 2.7 |
| S-29 | 543 | 597 | 554 | 600 | 1.6 |
| S-44 | 498 | 586 | 525 | 582 | 2.8 |
| S-45 | 534 | 596 | 558 | 600 | 2.3 |

Figure 2A (cont'd)

| Dye | Dye alone: Excitation wavelength (nm) | Dye alone: Emission wavelength (nm) | Dye with aggregate: Excitation wavelength (nm) | Dye with aggregate: Emission wavelength (nm) | Fluorescence enhancement: Aggregate/ monomer |
|---|---|---|---|---|---|
| Dbt-5 [TOL-9] | 539 | 597 | 545 | 598 | 2.2 |
| S-30 | 530 | 598 | 570 | 600 | 1.9 |
| Sip-7 [TOL-12] | 397 | 576 | 397 | 576 | 1.2 |
| S-28 | 384 | 608 | 384 | 608 | 1 |
| S-23 | 464 | 546 | 471 | 553 | 1.2 |
| SH-1070 | 408 | 500 | 408 | 480 | 1.2 |
| Yat2212 | 485 | 623 | 530 | 620 | 2.6 |
| D-91 | 395 | 520 | 396 | 517 | 1.03 |
| D-78 | 426 | 621 | 426 | 621 | 0.94 |
| D-68 | 553 | 696 | 558 | 694 | 1.1 |
| D-69 | 483 | 638 | 483 | 637 | 1.07 |
| D-160 | 481 | 631 | 493 | 617 | 1.2 |
| D-155 | 500 | 625 | 516 | 619 | 1.6 |
| D-72 | 380 | 477 | 375 | 469 | 1.1 |
| D-163 | 493 | 588 | 490 | 589 | 1.06 |
| D-159 | 487 | 603 | 494 | 593 | 1.5 |
| D-80 | 489 | 669 | 486 | 668 | 0.31 |

Figure 2A (cont'd)

| Dye | Dye alone: Excitation wavelength (nm) | Dye alone: Emission wavelength (nm) | Dye with aggregate: Excitation wavelength (nm) | Dye with aggregate: Emission wavelength (nm) | Fluorescence enhancement: Aggregate/monomer |
|---|---|---|---|---|---|
| D-84 | 494 | 623 | 507 | 602 | 2.8 |
| D-90 | 475 | 662 | 479 | 655 | 0.36 |
| D-162 | 472 | 706 | 565 | 692 | 9.9 |
| D-70 | 506 | 615 | 506 | 614 | 0.92 |
| D-86 | 388 | 544 | 387 | 544 | 1 |
| D-87 | 430 | 534 | 428 | 534 | 1.08 |
| D-85 | 450 | 515 | 534 | 608 | 2.3 |
| Tol-24 | 530 | 594 | 540 | 598 | 2.4 |
| Yat2325 | 503 | 624 | 538 | 622 | 2.5 |
| S-5 | 527 | 597 | 535 | 598 | 1.1 |
| S-38 | 535 | 599 | 555 | 602 | 2.1 |
| S-37 | 545 | 600 | 551 | 602 | 1.9 |
| S-3 | 562 | 595 | 565 | 596 | 1.2 |
| S-27 | 522 | 607 | 540 | 608 | 1.2 |
| SIP-2 | 397 | 576 | 397 | 575 | 1.3 |
| D-74 | 517 | 601 | 527 | 601 | 1 |
| Sbt | 520 | 592 | 551 | 594 | 2.8 |
| D-75 | 494 | 554 | 494 | 555 | 1.5 |

Figure 2A (cont'd)

| Dye | Dye alone: Excitation wavelength (nm) | Dye alone: Emission wavelength (nm) | Dye with aggregate: Excitation wavelength (nm) | Dye with aggregate: Emission wavelength (nm) | Fluorescence enhancement: Aggregate/ monomer |
|---|---|---|---|---|---|
| D-71 | 482 | 585 | 498 | 587 | 1.4 |
| Dbo-10 | 505 | 559 | 515 | 597 | 2.1 |
| SI-1999 | 582 | 595 | 582 | 595 | 1 |
| SL-42 | 555 | 567 | 555 | 567 | 0.9 |
| Dimer-NN | 431 | 577 | 440 | 580 | 1.12 |
| SIP-3 | 398 | 579 | 408 | 582 | 0.98 |
| SIP-10 | 404 | 582 | 440 | 590 | 0.79 |
| Dst-NN-6 | 397 | 572 | 402 | 572 | 1 |
| SIP-8 | 446 | 582 | 442 | 584 | 0.28 |
| Dst-NN-10 | 396 | 572 | 398 | 572 | 1.24 |
| Dst-NN-11 | 398 | 584 | 413 | 600 | 0.76 |
| Dst-NN-12 | 404 | 581 | 412 | 595 | 0.79 |
| SI-1035 | 512 | 545 | 512 | 546 | 1 |
| SI-1047 | 574 | 596 | 575 | 596 | 0.95 |
| SI-1056 | 546 | 571 | 548 | 572 | 1 |
| SL-1722 | 673 | 700 | 676 | 699 | 1 |

Figure 2A (cont'd)

| Dye | Dye alone: Excitation wavelength (nm) | Dye alone: Emission wavelength (nm) | Dye with aggregate: Excitation wavelength (nm) | Dye with aggregate: Emission wavelength (nm) | Fluorescence enhancement: Aggregate/ monomer |
|---|---|---|---|---|---|
| SL-2153 | 547 | 573 | 547 | 573 | 0.9 |
| SI-2596 | 491 | 594 | 492 | 609 | 1.1 |
| SI-2611 | 456 | 554 | 460 | 555 | 1 |
| T-164 | 559 | 575 | 559 | 572 | 1 |
| SH-0229 | 520 | 628 | 525 | 641 | 0.7 |
| T-33 | 589 | 656 | 589 | 656 | 0.7 |
| SH-0423 | 409 | 536 | 409 | 588 | 1 |
| SH-0428 | 588 | 601 | 588 | 603 | 2.3 |
| SH-0627 | 558 | 569 | 558 | 569 | 1.1 |
| T-333 | 559 | 576 | 559 | 576 | 1 |
| T-74 | 561 | 576 | 561 | 576 | 0.9 |
| SH-0999 | 640 | 653 | 585 | 596 | 2 |
| T-165 | 583 | 623 | 588 | 632 | 2.3 |
| T-364 | 582 | 628 | 581 | 630 | 1.4 |
| Dst-NN-13 | 398 | 576 | 409 | 576 | 0.65 |
| T-119 | 530 | 635 | 532 | 636 | 1 |
| T-15 | 554 | 571 | 564 | 575 | 1.2 |

Figure 2A (cont'd)

| Dye | Dye alone:<br><br>Excitation wavelength (nm) | Dye alone:<br><br>Emission wavelength (nm) | Dye with aggregate:<br><br>Excitation wavelength (nm) | Dye with aggregate:<br><br>Emission wavelength (nm) | Fluorescence enhancement:<br><br>Aggregate/ monomer |
|---|---|---|---|---|---|
| TOL-26 | 563 | 609 | 564 | 607 | 0.9 |
| Dst-NN-8 | 366 | 474 | 374 | 472 | 1.26 |
| SL-2057 | 589 | 603 | 591 | 605 | 1.26 |
| SL-2059 | 582 | 608 | 582 | 607 | 0.97 |
| SL-2132 | 532 | 604 | 558 | 609 | 1.46 |

| Dye | Structure | Dye | Structure |
|---|---|---|---|
| S-11 | 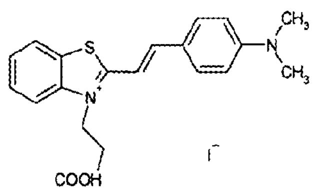 | SH-975 | 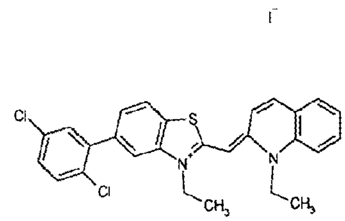 |
| S-12 | 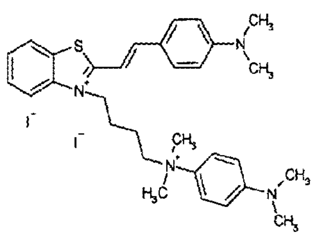 | SH-1036 | 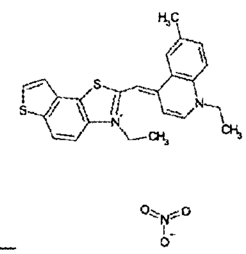 |
| SH-330 | 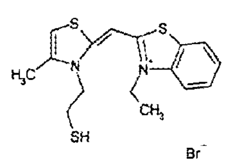 | SI-2599 | 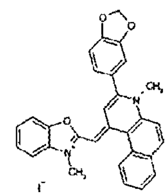 |
| SH-654 | 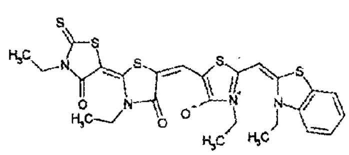 | SI-2600 | 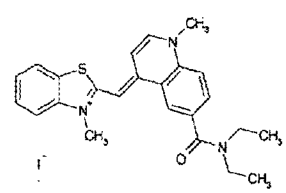 |
| SH-675 | 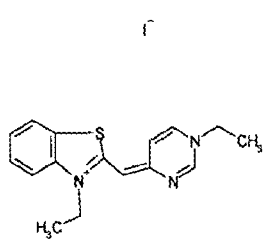 | S-7 | 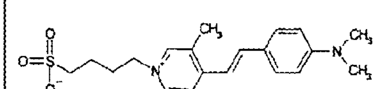 |

Figure 2B (cont'd)

| Dye | Structure | Dye | Structure |
|---|---|---|---|
| L-28 | | S-29 | |
| L-31 | 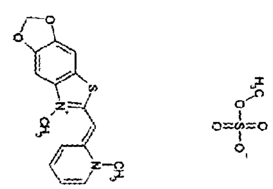 | S-44 | 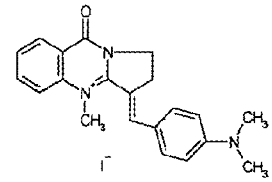 |
| L-28 | | S-45 | |
| TOL-4 | 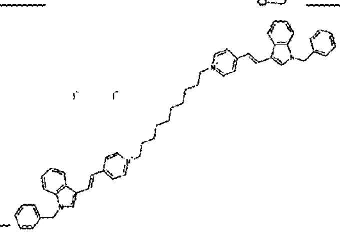 | S-30 | 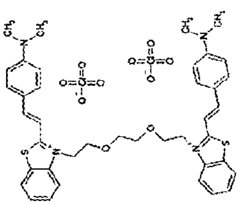 |
| TOL-10 | 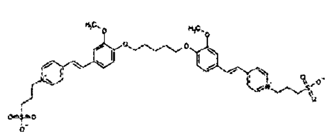 | Dbt-5 [TOL-9] | 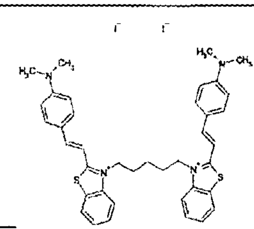 |
| S-26 | 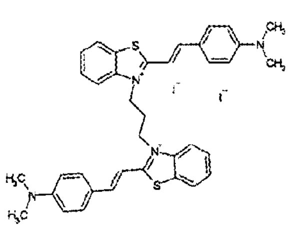 | Sip-7 [TOL-12] | 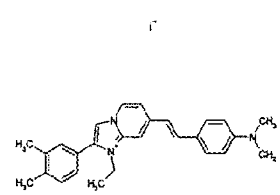 |

Figure 2B (cont'd)

| Dye | Structure | Dye | Structure |
|---|---|---|---|
| S-28 | 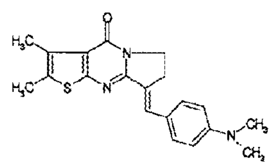 | D-68 | 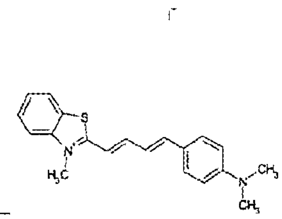 |
| S-23 | 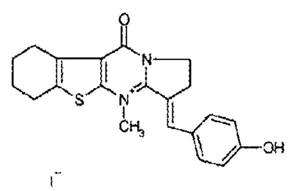 | D-69 | 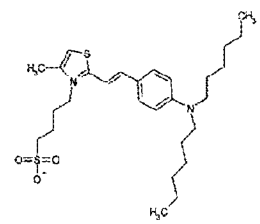 |
| SH-1070 | 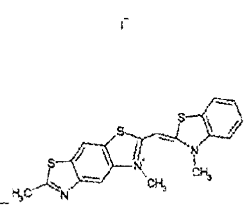 | D-160 | 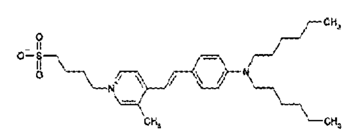 |
| Yat-2212 | 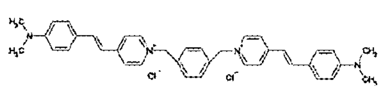 | D-155 | 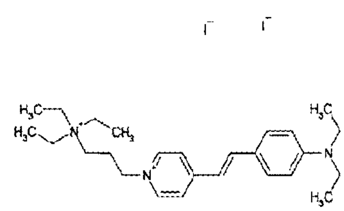 |
| D-91 | 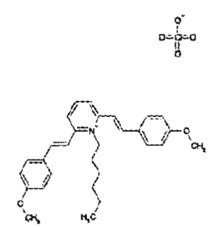 | D-72 | 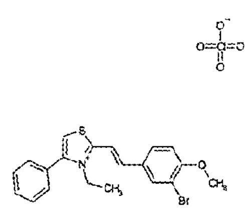 |
| D-78 | 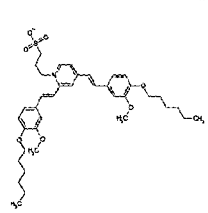 | D-163 | 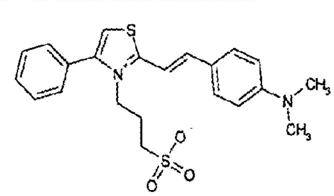 |

Figure 2B (cont'd)

| Dye | Structure | Dye | Structure |
|---|---|---|---|
| D-159 | 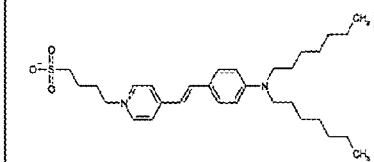 | D-86 | 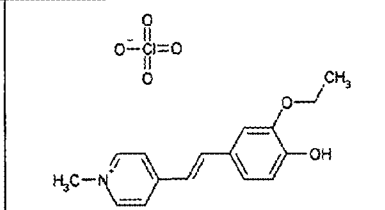 |
| D-80 | 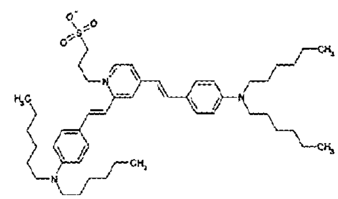 | D-87 | 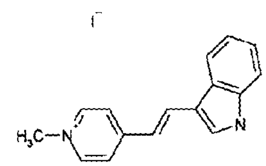 |
| D-84 | 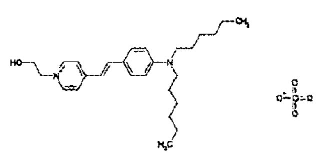 | D-85 | 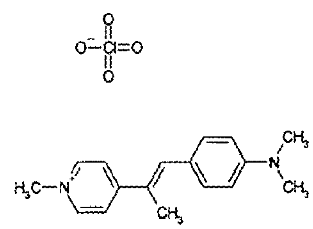 |
| D-90 | 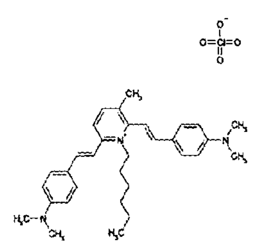 | Tol-24 | 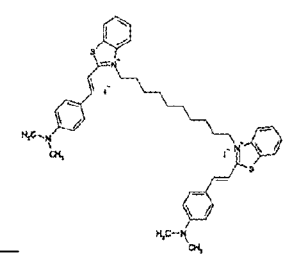 |
| D-162 | 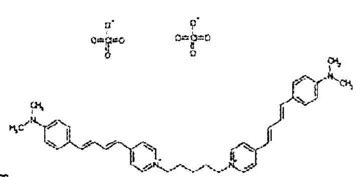 | Yat2325 | 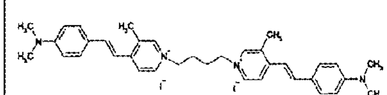 |
| D-70 | 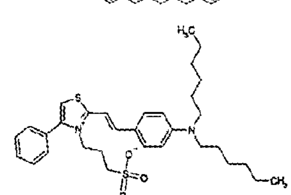 | S-5 | 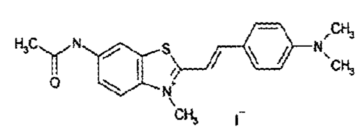 |

Figure 2B (cont'd)

| Dye | Structure | Dye | Structure |
|---|---|---|---|
| S-38 | 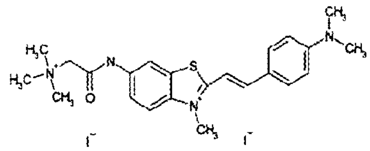 | Sbt | 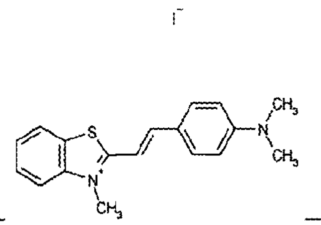 |
| S-37 | 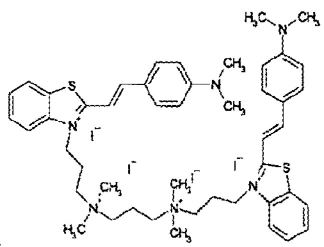 | D-75 | 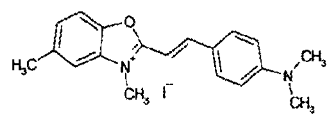 |
| S-3 | 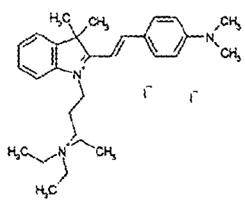 | D-71 | 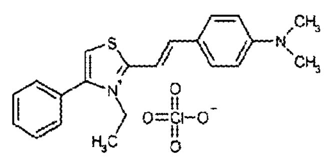 |
| S-27 | 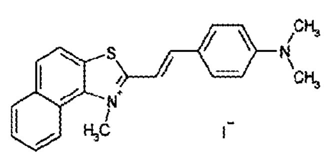 | Dbo-10 | 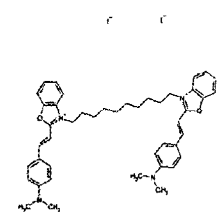 |
| SIP-2 | 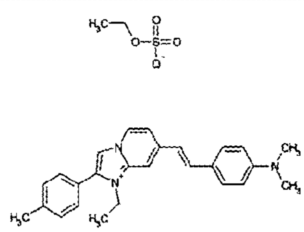 | SI-1999 | 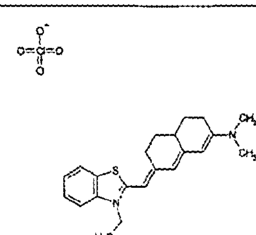 |
| D-74 | 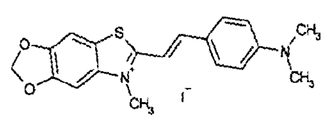 | SL-42 | 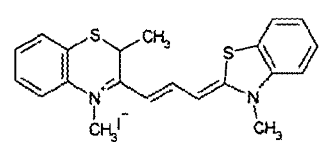 |

Figure 2B (cont'd)

| Dye | Structure | Dye | Structure |
|---|---|---|---|
| Dimer-NN | 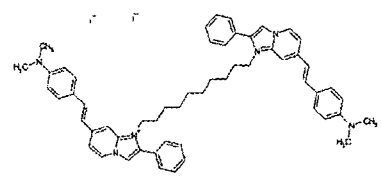 | Dst-NN-10 | 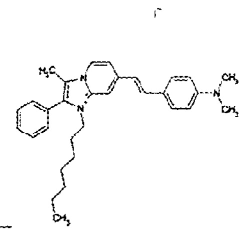 |
| SIP-3 | 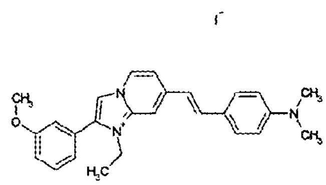 | Dst-NN-11 | 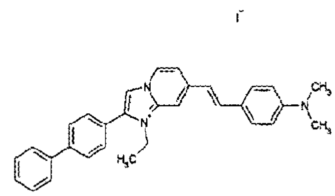 |
| SIP-10 | 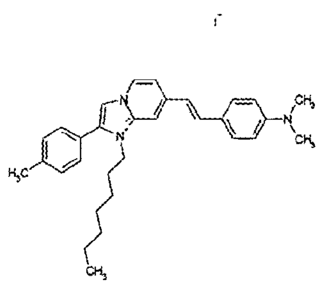 | Dst-NN-12 | 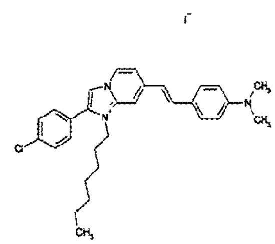 |
| Dst-NN-6 | 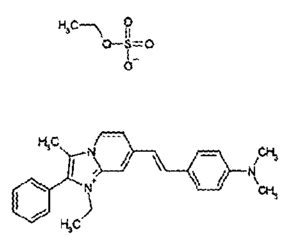 | SI-1035 | 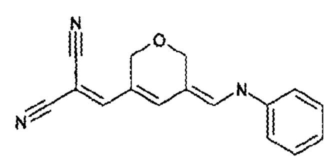 |
| SIP-8 | 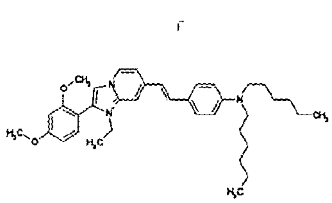 | SI-1047 | 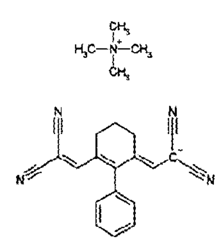 |

Figure 2B (cont'd)

| Dye | Structure | Dye | Structure |
|---|---|---|---|
| SI-1056 | 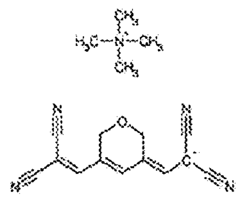 | SH-0229 | 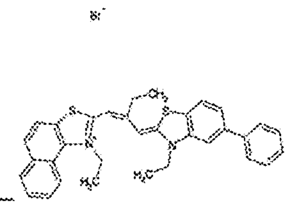 |
| SL-1722 | 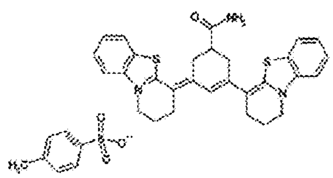 | T-33 | 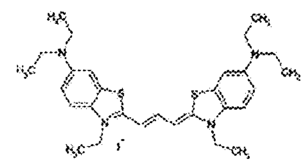 |
| SL-2153 | 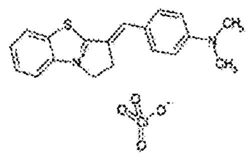 | SH-0423 | 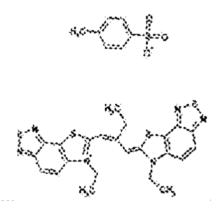 |
| SI-2596 | 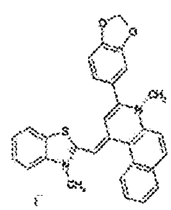 | SH-0428 | 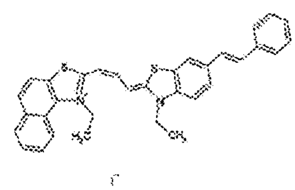 |
| SI-2611 | 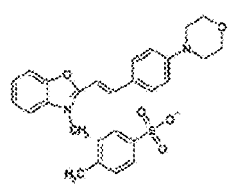 | SH-0627 | 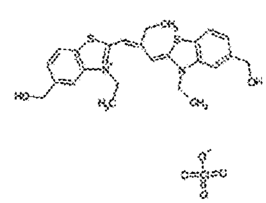 |
| T-164 | 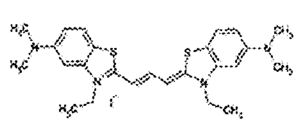 | T-333 | 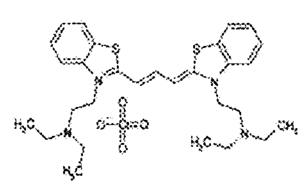 |

Figure 2B (cont'd)

| Dye | Structure | Dye | Structure |
|---|---|---|---|
| T-74 | 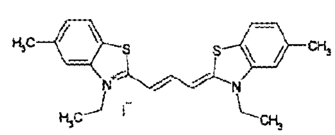 | T-15 | 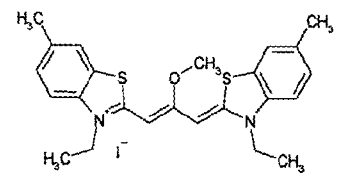 |
| SH-0999 | 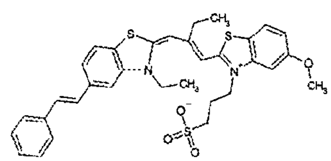 | TOL-26 | 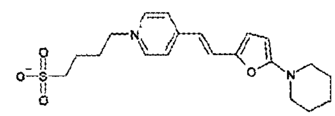 |
| T-165 | 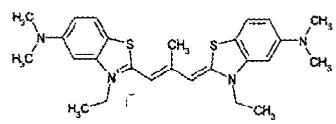 | Dst-NN-8 | 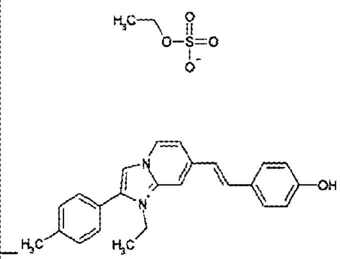 |
| T-364 | 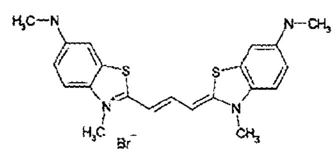 | SL-2057 | 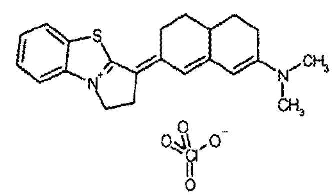 |
| Dst-NN-13 | 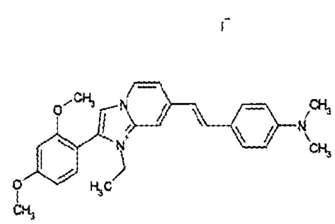 | SL-2059 | 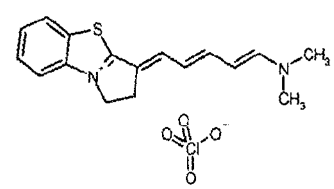 |
| T-119 | 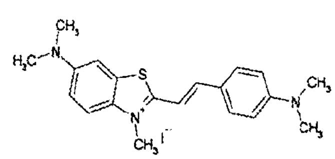 | SL-2132 | 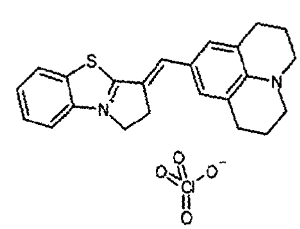 |

Fluorescence ratio of excipients added before heating vs. after heating using no excipients as a reference BLG Thermal Shift Curves

US 9,932,479 B2

DYES AND COMPOSITIONS, AND PROCESSES FOR USING SAME IN ANALYSIS OF PROTEIN AGGREGATION AND OTHER APPLICATIONS

CROSS-REFERENCE TO RELATED APPLICATIONS

This application is a divisional patent application Ser. No. 12/592,639 filed on Nov. 30, 2009, and is incorporated herein, by reference, in its entirety.

FIELD OF THE INVENTION

The field of the invention relates to novel dyes and compositions which are useful in processes for the analysis of protein aggregation and other applications including biopharmaceutical manufacturing and imaging diagnostics. More particularly, the present invention relates to compositions and methods for evaluating the aggregation state of peptides and polypeptides.

BACKGROUND OF THE INVENTION

The deposition of insoluble protein aggregates, known as amyloid fibrils, in various tissues and organs is associated with a number of neurodegenerative diseases, including Alzheimer's, Huntington's and Parkinson's diseases, senile systemic amyloidosis and spongiform encephalopathies [(Volkova K D, Kovalska V B, Balanda A O, Vermeij R J, Subramaniam V, Slominskii Y L, Yarmoluk S M (2007), "Cyanine dye-protein interactions: looking for fluorescent probes for amyloid structures". *J. Biochem. Biophys. Methods* 70: 727-733); and (Stefani M, Dobson C M (2003), "Protein aggregation and aggregate toxicity: new insights into protein folding, misfolding diseases and biological evolution". *J. Mol. Med.* 81: 678-699)]. Fibrillar deposits with characteristics of amyloid are also formed by several other proteins unrelated to disease, including the whey protein beta-lactoglobulin (BLG). All amyloid fibers, independent of the protein from which they were formed, have very similar morphology: long and unbranched, a few nanometers in diameter, and they all exhibit a cross-beta X-ray diffraction pattern. The ability to form amyloid fibrils of structurally and functionally diverse proteins, some of which are not associated with amyloid-deposition diseases, suggests that this property is common to all polypeptides Such amyloid structures are also known to possess a binding affinity for certain dyes, notably, Thioflavin T and Congo Red dyes.

Many proteins are known to be only marginally stable in solution, undergoing conformational changes due to various stresses during purification, processing and storage [(Arakawa T, Philo J S, Ejima D, Sato H, Tsumoto K. (2007), "Aggregation analysis of therapeutic proteins, part 3". *Bioprocess International* November (52-70). Such stresses may include elevated temperature, agitation and exposure to extremes of pH, ionic strength, or various interfaces (e.g., an air-liquid interface) and high protein concentration (as observed for some monoclonal antibody formulations). A wide variety of aggregates are encountered in biopharmaceutical samples, which range in size and physiochemical characteristics (e.g., solubility, reversibility). Protein aggregates span a broad size range, from small oligomers that are only a couple nanometers in length to insoluble micron-sized aggregates that extend to millions of monomeric units. Structurally altered proteins have an especially strong tendency to aggregate, often leading to their eventual precipitation. Irreversible aggregation is a major problem for the long-term storage and stability of therapeutic proteins and for their shipment and handling.

Mechanisms of Protein Aggregation

Aggregation is a major degradation pathway that needs to be characterized and controlled during the development of protein pharmaceuticals. In the bioprocessing arena, the mechanisms of protein aggregation are still not fully understood, despite the fact that aggregation is a major problem in therapeutic protein development (Arakawa T, Philo J S, Ejima D, Tsumoto K, Arisaka F (2006), "Aggregation analysis of therapeutic proteins, part 1". *Bioprocess International* 4 (10): 32-42). One plausible mechanism is that aggregation is driven or catalyzed by the presence of a small amount of a contaminant which serves as a nucleation site. That contaminant could be a damaged form of the protein product itself, host cell proteins, or even nonprotein materials, such as leachates from the container or resin particles associated with purification of the protein.

If the contaminant is the damaged protein itself, then its aggregation may lead to soluble oligomers, which become larger aggregates, visible particulates, or insoluble precipitates. Such soluble oligomers, host-cell contaminants, or nonprotein materials may serve as a nucleus onto which native proteins assemble and are incorporated into larger aggregates. Damaged forms of a protein product can also arise from chemical modification (such as oxidation or deamidation) and from conformationally damaged forms arising from thermal stress, shear, or surface-induced denaturation. Minimizing protein aggregation thus requires ensuring both chemical and physical homogeneity; that is, chemically modified or conformationally altered proteins must be removed from the final product.

A second mechanism that often leads to protein aggregation is initiated by the partial unfolding of the native protein during its storage. Protein conformation is not rigid—the structure fluctuates around the time-averaged native structure to different extents depending upon environmental conditions. Some partially or fully unfolded protein molecules are always present at equilibrium in all protein solutions, but most such molecules simply refold to their native structure. These unfolded proteins may in some instances, however, aggregate with other such molecules or may be incorporated into an existing aggregate nucleus, eventually forming larger aggregates, as described above. Factors such as elevated temperature, shaking (shear and air-liquid interface stress), surface adsorption, and other physical or chemical stresses may facilitate partial unfolding of proteins, leading to the cascade of events that cause aggregation.

A third aggregation mechanism is reversible self-association of the native protein to form oligomers. According to the law of mass action, the content of such reversible aggregates will change with total protein concentration. The tendency of different proteins to associate reversibly with one another is highly variable, and the strength of that association typically varies significantly with solvent conditions, such as pH and ionic strength. In principle, these reversible oligomers will dissociate completely as the protein becomes highly diluted, for example, after delivery of a therapeutic protein in vivo. Consequently, this class of aggregates is generally less of a concern than irreversible aggregates. Such reversible oligomers can eventually become irreversible aggregates, however. Preventing accumulation of irreversible aggregates may thus require minimizing the reversible association as well. Further, reversible self-association of proteins can significantly alter overall pharmaceutical properties of product solutions, such as solution viscosity.

Detection of reversible aggregates can be an especially challenging task. As such, aggregates can dissociate after their dilution during attempts to measure them. Additionally, the results of any analysis method incorporating a separation process in the workflow may depend very much upon the kinetic rates of the reversible association-dissociation reactions as well as the equilibrium constants.

One consequence of the complexities of monitoring aggregate formation processes is the difficulty of linking the effect (presence of aggregates) to its underlying cause, particularly because the key damage may occur at a time or place quite separated from the observed consequence. One example arises during the large-scale production of therapeutic monoclonal antibodies (MAbs). Acid stability plays a major role in the aggregation of MAbs because the process for their purification usually involves both low-pH elution from protein-A affinity columns and acid-treatment for viral inactivation.

The exposure of MAbs to a low-pH environment can result in small but significant conformational changes that can additionally depend upon factors such as temperature, and solvent composition. While such partially unfolded MAbs may not aggregate at low pH, they may aggregate during subsequent manufacturing steps involving changes in pH or ionic strength. A larger conformational change at low pH generally leads to more aggregates upon increasing the pH. Typically, protein aggregate formation from the low-pH structure is not a fast process, but it does occur slowly from the association of damaged monomers that have not returned to their fully native structure. This and other types of protein aggregation phenomena may not manifest themselves until months after manufacturing a particular lot of protein or until later stages of the product development process. Regardless of the mechanism of aggregation, preventing aggregation problems requires sensitive and reliable technologies for quantitative determination of aggregate content and aggregate characteristics.

Since the earliest clinical applications of protein pharmaceuticals in medicine, aggregation problems have been implicated in adverse reactions in humans and other safety issues. In order to minimize such risks from therapeutic proteins in the clinic, formulations must be optimized to minimize aggregation during storage, handling, and shipping.

Analysis of Protein Aggregation

The analysis of protein aggregation can be formally classified into four experimental types [(Arakawa T, Philo J S, Ejima D, Tsumoto K, Arisaka F (2006), "Aggregation analysis of therapeutic proteins, part 1". *Bioprocess International* 4(10): 32-42); (Arakawa T, Philo J S, Ejima D, Tsumoto K, Arisaka F (2007), "Aggregation analysis of therapeutic proteins, part 2". *Bioprocess International* 5(4): 36-47); (Arakawa T, Philo J S, Ejima D, Sato H, Tsumoto K (2007), "Aggregation analysis of therapeutic proteins, part 3". *Bioprocess International* 5(10): 52-70) (Krishnamurthy R, Sukumar M, Das T K, Lacher N A (2008), "Emerging analytical technologies for biothererapeutics development". *Bioprocess International* 6(5): 32-42)].

The first type of protein aggregation analysis is the most conventional approach, wherein a small volume of sample is applied to a separation medium and forms a band or zone. As the band migrates through the medium, the proteins separate according to differences in size, electrophoretic charge, or mass. Gel electrophoresis, size exclusion chromatography (SEC), field flow fractionation (FFF), and the occasionally used band sedimentation technique belong to this class of methods. The movement of the band or zone in these methods is often monitored using absorbance or refractive index detection.

In the second type of analysis, the sample initially and uniformly fills a measurement cell. When an electrical or centrifugal driving force is then applied, the protein moves along the applied field, leaving a protein-depleted solvent, which creates a boundary between protein-free and protein-containing solution phases. The movement of this boundary over time is measured. This mode of separation is used in analytical ultracentrifugation-sedimentation velocity (AUC-SV) and moving-boundary electrophoresis.

The third type of analysis is a measurement of particle size with no physical separation. An example of this method is referred to as correlation spectroscopy and it measures the fluctuation of particles in solution due to Brownian motion (i.e., measures protein diffusion coefficients). Fluctuations of scattered light and of fluorescence intensity have been employed in this type of measurement. One of the most widely employed methods in this category is referred to as dynamic light scattering (DLS).

SEC is the most commonly implemented control method and has become an industry benchmark for quantification of protein aggregates. SEC is seen as a versatile technique for separation and quantification of protein aggregates because of its high precision, high throughput, ease of use, compatibility with a quality control (QC) environment, and in most cases ability to accurately quantify protein aggregates. In spite of these strengths, several concerns exist with the technique including: a potential loss of aggregates (especially multimers), interaction of samples with a column matrix, the required change of a sample buffer matrix to an SEC mobile phase, and the inherent requirement for dilution of samples. Additionally, perturbation of the distribution of protein aggregates under standard SEC methodological conditions is possible.

AUC-SV relies on hydrodynamic separation of various species in a heterogeneous protein mixture under strong centrifugal force. AUC-SV complements SEC in resolving and quantifying low levels of protein aggregates. The main advantages of AUC-SV are seen in its ability to detect and measure higher order aggregates (which may elute in the void volume of an SEC column) and to conduct these measurements without exposing samples to a column resin or SEC mobile phase. AUC-SV is considered an accurate method because it does not require standards or dissociate aggregates; thus it can be used as an orthogonal method to verify the accuracy of SEC results. AUC-SV suffers from lower precision than SEC, however. The practical aspects of AUC-SV that impact precision and accuracy are beginning to be understood better, and several recent studies have demonstrated the utility of AUC-SV to detect and quantify aggregates present at relatively low (~1%) levels. Despite its advantages, AUC-SV is not yet readily amenable for use as a routine release test in the biotechnology industry because of issues related to low throughput, the need for specialized equipment, performance problems at high protein concentrations, the need for skilled practitioners of the method, and difficulty in validating data analysis software.

DLS uses the time-dependent fluctuations of a scattered-light signal to calculate the hydrodynamic diameter of protein aggregates and their relative proportions. This method is highly sensitive to large aggregates because the intensity of scattered light increases proportionally with molecular weight. As a result, very large aggregates (e.g., a 1,000-mer) present at trace levels (≤0.1%) can be detected with high sensitivity. If present, such aggregates would elute in the void volume of an SEC column or they may be filtered out. Although this method is ideal for detecting very low mass fractions of large aggregates, it cannot resolve species that are similar in size. At least a three- to five-fold difference in hydrodynamic diameter is required for resolving different species. DLS is also not amenable to use as a control method because it is semi-quantitative and very sensitive to dust or other extraneous particles. Results also depend on the algorithm used for data analysis, which is often proprietary to the manufacturer of a particular instrument.

As an orthogonal technique to SEC and AUC-SV, analytical field-flow fractionation (aFFF) has gained popularity in recent years for its ability to fractionate protein aggregates without a column. aFFF most commonly uses two fluid flows ("fields") in a channel to achieve particle separation based upon molecular weight and hydrodynamic size (diffusion coefficient). Injected macromolecular species are held in place by a cross flow on a semi-permeable membrane while a perpendicular channel flow carries molecules forward based on their diffusion coefficient, thereby providing size-based fractionation. Because aFFF involves no column interactions, it is considered a gentler separation technique than SEC. Concerns regarding the interaction of aggregates with the membrane have yet to be completely addressed, however. aFFF can be coupled with different detectors including light scattering, refractive index, and ultraviolet (UV) detectors. When compared with SEC, the precision and limit of detection of aFFF is inferior in the high-molecular-weight range, because of increased baseline noise. Experimental conditions (e.g., cross-flow rate) for reasonable separations in one size range are also not generally applicable to other size ranges, making the technique cumbersome, especially when analyzing a broad range of masses. Along with other limitations, such as the need for specialized equipment and a skilled operator, and the difficulty in validating the method prevents the use of aFFF in applications for release and stability monitoring.

Resolution and the size range that can be evaluated in one particular analysis vary widely among the above mentioned techniques. SEC cannot handle a large range of sizes because the pore size or degree of polymerization of the resin must be adjusted to the size of the protein species. If a protein sample contains widely different sizes, many techniques are unsuitable for analyzing all sizes simultaneously. FFF and DLS can cover a very large range of sizes, but in the case of DLS, resolution is generally fairly poor, and FFF entails some trade-off between resolution and dynamic range. SV-AUC is intermediate in capability relative to FFF and DLS. The dynamic range of SV-AUC is fairly good, generally a factor of 100 or more in molecular weight at any particular rotor speed. The resolution of SV-AUC is generally not ideal for separating monomer from dimer, compared with the best SEC columns (especially for lower molecular weight proteins). SV-AUC is often much better, however, than SEC for resolving moderate size oligomers, (tetramers to decamers).

The cited analytical techniques also differ significantly with respect to their overall sensitivity, in other words, their ability to detect and quantify small percentages of irreversible aggregates. SEC, FFF, and SV-AUC are all capable of detecting aggregates at levels as low as ~0.1% when they are well separated from other species. The quantification of species that elute from SEC or FFF is quite good, but aggregates can easily be lost during the separation process. Thus, SEC and FFF may provide good precision but poor accuracy. For SV-AUC, loss of protein aggregates to surfaces is usually not a problem, but accurate quantification of small oligomers (dimer-tetramer) at total levels of ~2% or less is quite difficult.

The sensitivity of DLS increases linearly with the stoichiometry of the protein aggregate. DLS is for all practical purposes useless for detecting oligomers smaller than an octamer, because the technique cannot resolve such oligomers from monomeric species, and for those protein aggregate species that are resolved, the accuracy of the weight fractions is quite poor, typically plus or minus factors of two to ten. DLS exhibits excellent sensitivity, however, for very large aggregate species, which can often be detected at levels far below 0.01% by weight.

Overall, no single analytical technique is ideal for every protein or is optimal for analyzing the wide range of aggregation problems that can arise with protein pharmaceutical formulation. One important industry trend are recent requests from regulatory agencies that the protein aggregation analytical method used for lot release and/or formulation development. Typically, this means SEC which is cross-checked through one or more orthogonal approaches to ensure detection of all relevant protein aggregate species. Comparison of protein aggregate content using various technologies is thus an emerging topic of interest in biotechnology research.

Fluorescent Dyes and Protein Aggregation

In a fourth method of aggregate analysis, fluorescent dyes have been used to stain amyloidogenic material in histology, while insights into the prerequisites and kinetics of amyloid formation have been obtained by the in vitro analysis of this process using similar dyes [(Volkova K D, Kovalska V B, Balanda A O, Losytskyy My, Golub A G, Vermeij R J, Subramaniam V, Tolmachev O I, Yarmoluk S M (2008), "Specific fluorescent detection of fibrillar α-synuclein using mono- and trimethine cyanine dyes". *Bioorganic & Medicinal Chemistry* 16:1452-1459); (Volkova K D, Kovalska V B, Balanda A O, Vermeij R J, Subramaniam V, Slominskii Y L, Yarmoluk S M (2007), "Cyanine dye-protein interactions: looking for fluorescent probes for amyloid structures". *J. Biochem. Biophys. Methods* 70:727-733); (Volkova K D, Kovalska V B, Segers-Nolten G M, Veldhuis G, Subramaniam V, Slominskii Y L, Yarmoluk S M (2009), "Detection and characterization of protein aggregates by fluorescence microscopy". *Biotechnic & Histochemistry* 84(2): 55-61); (Demeule B, Gurny R, Arvinte T (2007), "Explorations of the application of cyanine dyes for quantitative α-synuclein detection". *International Journal of Pharmaceutics* 329: 37-45]. The fluorescent probes, Thioflavin T and Congo Red, have been the most frequently used dyes to detect the presence of amyloid deposits. Both the benzothiazole dye Thioflavin T and the symmetrical sulfonated azo dye Congo Red have been adapted to study the formation of amyloid fibrils in solution using the fluorescence properties of these molecules. The amyloid aggregates cause large enhancements in fluorescence of the dye thioflavin T, exhibit green-gold birefringence upon binding the dye Congo red, and cause a red-shift in the absorbance spectrum of Congo red. Amyloid fibril detection assays have suffered from several drawbacks, however, when using Thioflavin T, Congo Red and their derivatives. For instance, Congo Red can bind to native α-proteins such as citrate synthase and interleukin-2 [Khurana R, Uversky V N, Nielsen L, Fink A L (2001), "Is Congo Red an Amyloid-specific Dye". *J. Biol. Chem* 276: 22715-22721]. As a consequence of its poor optical properties, the Congo Red derivative Chrysamine-G only weakly stains neuritic plaques and cerebrovascular amyloid in post-mortem tissue [Klunk W E, Debnath M L, Koros A M, Pettegrew J W (1998) "Chrysamine-G, a lipophilic analogue of Congo Red, inhibits A beta-induced toxicity in PC12 cells.". *Life Sci.* 63: 1807-1814]. Furthermore, the binding of dyes can influence the stability of amyloid aggregates, and the interplay with other components (for example, during testing of potential amyloid inhibitors) is unpredictable [Murakami K, Irie K, Morimoto A, Ohigashi H, Shindo M, Nagao M, Shimizu T, Shirasawa T (2003), "Neurotoxicity and Physicochemical Properties of Aβ Mutant Peptides from Cerebral Amyloid Angiopathy: IMPLICATION FOR THE PATHOGENESIS OF CEREBRAL AMYLOID ANGIOPATHY AND ALZHEIMER'S DISEASE". *J. Biol. Chem* 278: 46179-46187]. Importantly, there exists a great variability among the different amyloid fibrils in their ability to bind Congo Red and Thioflavin T. Fluorescence intensity using Thioflavin T can vary depending upon the structure and morphology of the amyloid fibrils [Murakami K, Irie K, Morimoto A, Ohigashi H, Shindo M, Nagao M, Shimizu T, Shirasawa T (2003), "Neurotoxicity and Physicochemical Properties of Aβ Mutant Peptides from Cerebral Amyloid Angiopathy: IMPLICATION FOR THE PATHOGENESIS OF CEREBRAL AMYLOID ANGIOPATHY AND ALZHEIMER'S DISEASE". *J. Biol. Chem* 278: 46179-46187]. Despite the widespread use of Thioflavin T, its application to amyloid quantification often generates inconsistent and inaccurate results. Variations in spectral properties caused by buffer conditions and protein-dye ratios result in poor reproducibility, complicating the use of Thioflavin T for quantitative assessment of fibril formation. In the absence of other more reliable assays, investigators have relied heavily upon Thioflavin T as a reporter probe for amyloid protein aggregation. A reliable method for amyloid quantification likely would be useful not only for detecting mature amyloid fibrils, but also for monitoring the kinetics of fibrillogenesis, which is essential for better understanding of the underlying biophysics and mechanism of the protein aggregation process. Furthermore, such an assay would be a tool for discovery and development of therapeutic compounds capable of blocking protein aggregation.

Thus the design of new dyes which can selectively interact with fibrillar amyloidogenic proteins is of substantial importance for basic research, and has a crucial practical significance for biotechnology and medicine. Dialkylamino-substituted monomethine cyanine T-284 and meso-ethyl-substituted trimethine cyanine SH-516 have demonstrated higher emission intensity and selectivity to aggregated α-synuclein (ASN) than the classic amyloid stain Thioflavin T; while the trimethinecyanines T-49 and SH-516 exhibit specifically increased fluorescence in the presence of fibrillar β-lactoglobulin (BLG) [Volkova K D, Kovalska V B, Balanda A O, Vermeij R J, Subramaniam V, Slominskii Y L, Yarmoluk S M (2007), "Cyanine dye-protein interactions: looking for fluorescent probes for amyloid structures". *J. Biochem. Biophys. Methods* 70: 727-733]. These dyes demonstrated the same or higher emission intensity and selectivity to aggregated BLG as Thioflavin T. Recently, Nile Red dye has been used to detect antibody A aggregate, but it did not stain all types of protein aggregates, underscoring the need to several analytical methods in order to assess protein aggregation [Demeule B, Gurny R, Arvinte T (2007), "Detection and characterization of protein aggregates by fluorescence microscopy". *International Journal of Pharmaceutics* 329: 37-45].

Optimization of Protein Formulations

Another potential application of a fluorescence based protein aggregate detection technique relates to pharmaceutical protein formulations [(Kim S, Antwerp W P V, Gross T M, Gulati P S (2004), "Methods of evaluating protein formulation stability and surfactant-stabilized insulin formulations derived there from". U.S. Pat. No. 6,737,401 B2); [(Hsu C C, Nguyen H M, Wu S S (1993), "Reconstituteable lyophilized protein formulation". U.S. Pat. No. 5,192,737); (Andya J, Cleland J L, Hsu C C, Lam X M, Overcashier D E, Shire S J, Yang J Y-F, Wu S S-Y (2004), "Protein formulation". U.S. Pat. No. 6,685,940 B20); [(Ludvigsen S, Schein M, Boving T E G, Bonde C, Lilleore A, Engelund D K, Nielsen B R (2008), "Stable formulations of peptides". US patent: application 2008/0125361 A1)]. The physical stability of pharmaceutical protein formulations is of great importance because there is always a time delay between production, protein formulation and its subsequent delivery to a patient. The physical stability of a protein formulation becomes even more critical when using drug delivery devices to dispense the protein formulation, such as infusion pumps and the like. When the delivery device is worn close to the body or implanted within the body, a patient's own body heat and body motion, plus turbulence generated in the delivery tubing and pump, impart a high level of thermo-mechanical stress to a protein formulation. In addition, infusion delivery devices expose the protein to hydrophobic interfaces in the delivery syringes and catheters. These interfacial interactions tend to destabilize the protein formulation by inducing denaturation of the native structure of the protein at these hydrophobic interfaces.

In an optimized protein formulation, the protein should remain stable for several years, maintaining the active conformation, even under unfavorable conditions that may occur during transport or storage. Protein formulation screening needs to be performed before the assessment of safety, toxicity, ADME (absorption distribution metabolism excretion), pharmacology and the testing of biological activity in animals. Currently, protein formulation in the pharmaceutical industry is generally a slow process and would benefit from fast formulation screening approaches that do not require overly complicated instrumentation techniques.

The formulation of protein drugs is a difficult and time-consuming process, mainly due to the structural complexity of proteins and the very specific physical and chemical properties they possess. Most protein formulations contain excipients which are added to stabilize protein structure, such as a particular buffer system, isotonic substances, metal ions, preservatives and one or more surfactants, with various concentration ranges to be tested. The conventional analytical methods usually require a long period of time to perform, typically twenty or more days, as well as manual intervention during this period. The development of new formulations is costly in terms of time and resources. Moreover, even for a known protein formulation, batch to batch quality control analysis is often less than optimal using the current state of the art methods. Therefore, a versatile, reliable, rapid and resource-efficient analytical method is desired for both developing novel protein formulations and identifying protein stability in quality control procedures. The ideal analytical method would be sensitive, accurate, and linear over a broad range, resistant to sample-matrix interference, capable of measuring all possible structural variants of a protein, and compatible with high throughput screening.

A high throughput screening (HTS) platform for optimization of protein formulation has been proposed based upon the use of multi-well microplates ([(Capelle Martinus A H, Gurny R, Arvinte T (2009), "A high throughput protein formulation platform: Case study of salmon calcitonin". *Pharmaceutical Research* 26(1): 118-128). Basically, such an HTS platform was envisioned to consist of two components: (i) sample preparation and (ii) sample analysis. Sample preparation involves automated systems for dispensing the drug and the formulation ingredients in both liquid and powder form. The sample analysis involves specific methods developed for each protein to investigate physical and chemical properties of the formulations in the microplates.

The techniques that could be coupled with such an HTS platform include UV-Visible absorbance/turbidity, light scatter, fluorescence intensity, resonance energy transfer, fluorescence anisotropy, Raman spectroscopy, circular dichroism, Fourier transform infrared spectroscopy (FTIR), surface plasmon resonance and fluorescence lifetime. Ideally, however, the analysis technique should be specific, quantitative, robust, cost-effective, easily accessed, easy to use and informative (Avinte et al utilized several assays coupled with HTS to optimize a salmon calcitonin formulation: turbidity (absorbance at 350 nm), intrinsic tyrosine fluorescence, 1-anilino-naphthalene-8-sulfonate (ANS) fluorescence and Nile Red fluorescence. Addition of the dyes (Nile Red and ANS) were employed to examine protein conformational changes. Their findings were in accordance with the salmon calcitonin formulations that were patented and used commercially, lending credence to the concept that fluorescent probe-based approaches can be employed in protein formulation optimization activities. The use of several complementary analytical methods permits the selection of formulations using carefully designed assay criteria. The investigators found that in some cases, an increase in turbidity was observed without an increase in ANS or Nile Red fluorescence. In other formulations, an increase in fluorescence was detected without an increase in turbidity. This suggests that these dyes are not necessarily measuring the exact same biophysical phenomenon as the turbidity measurements. Measuring the fluorescence of at least two dyes in combination with turbidity and intrinsic fluorescence was, therefore, recommended.

Among these techniques, fluorescence detection from externally added dyes, which enhances fluorescence intensity upon interacting with misfolded or aggregated protein, is most attractive, because this technique requires minimum protein concentration due to its high sensitivity and simple implementation on a microplate reader.

Real time stability testing of a particular formulation may demonstrate no immediately apparent effect on physical or chemical stability. Accelerated stability testing can help, therefore, in facilitating the determination of the most suitable excipients and concentrations. Storage at different target temperatures (0-50° C.), illumination of samples, mechanical stress (i.e., agitation that simulates handling and transportation), multiple freeze-thaw cycles (mimicking frozen storage, freeze drying), oxygen purging, increased humidity and seeding are different ways to accelerate protein degradation.

High throughput spectroscopy is a fast and versatile method for initial screening of the physical stability of protein formulations. The microplate well-based platform could be enhanced with accelerated stress testing and methods to determine chemical stability, e.g., electrophoresis, HPLC, mass spectrometry. For instance, Thioflavin T has been used to select and optimize FDA-approved surfactant(s) in insulin formulations using magnetically stirring to accelerate insulin aggregation (U.S. Pat. No. 6,737,401 B2).

Thermal Shift Assay

Fluorescent dyes have been used to monitor protein stability by systematically varying the temperature of test samples, also known as the Thermofluor® technique [(Pantoliano M W, Rhind A W, Salemme F R (2000), "Microplate thermal shift assay for ligand development and multivariable protein chemistry optimization". U.S. Pat. No. 6,020,141); (Matulis D, Kranz J K, Salemme F R, Todd M J (2005), "Thermodynamic stability of carbonic anhydrase: Measurements of binding affinity and stoichiometry using thermofluor". *Biochemistry* 44: 5258-5266); (Mezzasalma T M, Kranz J K, Chan W, Struble G T, Schalk-Hihi C, Deckman I C, Springer B A, Todd M J (2007), "Enhancing recombinant protein quality and yield by protein stability profiling". *J. Biomolecular Screening* 12(3): 418-428); [(Volkova K D, Kovalska V B, Balanda A O, Losytskyy My, Golub A G, Vermeij R J, Subramaniam V, Tolmachev O I, Yarmoluk S M (2008), "Specific fluorescent detection of fibrillar α-synuclein using mono- and trimethine cyanine dyes". *Bioorganic & Medicinal Chemistry* 16: 1452-1459); (Ericsson U B, Hallberg B M, DeTitta G T, Dekker N, Nordlund P (2006), "Thermofluor-based high-throughput stability optimization of proteins for structural studies". *Analytical Chemistry* 357: 289-298); (Todd M J, Cummings M D, Nelen M I (2005), "Affinity assays for decrypting protein targets of unknown function". *Drug Discovery Today* 2 (3): 267-273)]. Protein stability can be altered by various additives including but not limited to excipients, salts, buffers, co-solvents, metal ions, preservatives, surfactants, and ligands. Protein stability can be shifted by various stresses, including elevated temperature, referred to as thermal shift, or chemical denaturants, such as urea, guanidine isocyanate or similar agents. A protein stability shift assay offers a wide spectrum of applications in the investigation of protein refolding conditions, optimization of recombinant protein expression/purification conditions, protein crystallization conditions, selection of ligand/drug/vaccine/diagnostic reagents and protein formulations.

The classic thermal shift technology utilizes the dye SYPRO® Orange and involves the use of a melting point device to raise the temperature stepwise [(Raibekas A A (2008), "Estimation of protein aggregation propensity with a melting point apparatus". *Anylytical Biochemistry*, 380: 331-332). Thermal shift technology is coupled with aggregation detection technologies, such as light scattering technology or internal fluorescence from protein (such as tyrosine or tryptophan) to monitor protein aggregation and unfolding respectively. This type of technology usually requires a high protein concentration, therefore, it is not cost-effective. In addition, thermal shift technology cannot work effectively on formulations with low protein concentrations or finalize protein formulations which require a very low detection limit (typically ~1-5% protein aggregates).

Fluorometric Screening Assay for Protein Disulfide Isomerase (PDI)

Protein disulfide isomerase (PDI, EC5.3.4.1) is a 57-kDa enzyme expressed at high levels in the endoplasmic reticulum (ER) of eukaryotic cells [(Ferrari D M, Soling H D (1999), "The protein disulfide-isomerase family: unraveling a string of folds". Biochem. J. 339: 1-10)]. PDI was the first enzyme known to possess the disulfide isomerase activity and has been well characterized over the past three decades. In ER, PDI catalyzes both the oxidation and isomerization of disulfides of nascent polypeptides. Under the reducing condition of the cytoplasm, endosomes and cell surface, PDI catalyzes the reduction of protein disulfide bonds.

Folding catalysts such as PDI and peptidylprolyl isomerase accelerate slow chemical steps that accompany folding. Disulfide bond formation can occur quite rapidly, even before the completion of synthesis, but for some proteins disulfide bond formation is delayed and occurs post-translationally. PDI catalyzes disulfide formation and rearrangement by thiol/disulfide exchange during protein folding in the ER. As a member of the thioredoxin superfamily, which also includes homologs such as ERp57, PDIp, ERp72, PDIr and ERp5, PDI has two independent but non-equivalent active sites, with one positioned close to the C-terminus and another close to the N-terminus. Each site possesses two cysteine residues (CGHC) that cycle between the dithiol and disulfide oxidation states. The disulfide bond at the active site of PDI is a good oxidant that directly introduces a disulfide bond into protein substrates. The dithiol redox state is essential for catalyzing disulfide rearrangements. The necessity of having oxidized and reduced active sites for catalysis of different steps results in a redox optimum. Besides its major role in the processing and maturation of secretory proteins in ER, PDI and its homologs have been implicated in other important cellular processes. For example, cellular insulin degradation occurs in a sequential fashion with several identified steps. The initial degradative step occurs in endosomes with two or more cleavages in the B chain occurring. This is followed by reduction of disulfide bonds by PDI, or a related enzyme, generating an intact A chain and fragments of B chain. The insulin fragments are further cleaved by multiple proteolytic systems, such as the lysosomal degradation pathway.

PDI and its homologs also play roles in the processing and maturation of various secretory and cell surface proteins in the ER following their synthesis. Several in vitro studies have also suggested a chaperone function of PDI, that is to assist in protein folding or refolding. During ER stress, as for example during hypoxia in endothelial cells and astrocytes in the cerebral cortex, PDI is up-regulated. This indicates that PDI is involved in protecting cells under pathological or stressful conditions.

Besides ER, PDI also exists on many cell surfaces, such as endothelial cells, platelets, lymphocytes, hepatocytes, pancreatic cells and fibroblasts. For the reductive activity of plasma membrane, PDI is required for endocytosis of certain exogenous macromolecules. The cytotoxicity of diphtheria toxin is blocked by PDI inhibitors, which block the cleavage of the inter-chain disulfide bonds in the toxin. PDI also mediates reduction of disulfide bonds in human immunodeficiency virus envelope glycoprotein 120, which is essential for infectivity. PDI inhibitors can thus prevent virus entry into cells. Such functional activities make PDI and its homologs attractive drug targets.

Biochemical assays related to measuring PDI activity have been described. (1) ScRNase assay: PDI converts scrambled (inactive) RNase into native (active) RNase that further acts on its substrate. The reported sensitivity of the assay is in the micromolar range [Lyles M M, Gilbert H F (1991). "Catalysis of the oxidative folding of ribonuclease A by protein disulfide isomerase: dependence of the rate on the composition of the redox buffer". *Biochemistry* 30(3): 613-619]. (2) The Insulin Turbidity Assay: PDI breaks the two disulfide bonds between the two insulin chains (A and B) that results in precipitation of the B chain. This precipitation can be monitored by measuring turbidity (absorbance at 620 nm), which in turn indicates PDI activity. Sensitivity of this assay is in the micromolar range [Lundstrom J, Holmgren A (1990), "Protein disulfide-isomerase is a substrate for thioredoxin reductase and has thioredoxin-like activity". *J. Biol. Chem.* 265(16): 9114-9120]. Recently an end-point, high throughput screening assay of PDI isomerase activity based on enzyme-catalyzed reduction of insulin in the presence of dithiothreitol using hydrogen peroxide as a stop reagent has been developed [(Smith A M, Chan J, Oksenberg D, Urfer R, Wexler D S, O W A, Gao L, McAlorum A, Huang S (2004). "A high-throughput turbidometric assay for screening inhibitors of protein disulfide isomerase activity" (*J. Biomolecular Screening* 9 (7): 614-620); (Huang S, Oksenberg D, Urfer R (2005). "High-throughput turbidometric assay for screening inhibitors of protein disulfide isomerase activity" (U.S. Pat. No. 6,977,142 B2).

(3) The Di-E-GSSG assay: This is the fluorometric assay that can detect picomolar quantities of PDI and is, therefore, considered the most sensitive assay to date for detecting PDI activity. Di-E-GSSG has two eosin molecules attached to oxidized glutathione (GSSG). The proximity of eosin molecules leads to the quenching of its fluorescence. Upon breakage of the disulfide bond by PDI, however, fluorescence increases 70 fold [Raturi A, Mutus B (2007). "Characterization of redox state and reductase activity of protein disulfide isomerase under different redox environments using a sensitive fluorescent assay". *Free Radic. Biol. Med.* 43(1): 62-70]. Certain common excipients can cause signal generation as well, such as 2-mercaptoethanol and dithiothreitol.

In view of the important functional activities of PDI and homologous enzymes, sensitive, real-time, high throughput methods that are time and cost-effective are highly desirable.

Chaperone/Anti-Chaperone Activity

A chaperone is a protein that can assist unfolded or incorrectly folded proteins to attain their native state by providing a microenvironment in which losses due to competing folding and aggregation reactions are reduced. ((Puig A, Gilbert H F (1994), "Protein disulfide isomerase exhibits chaperone and anti-chaperone activity in the oxidative refolding of lysozyme". *The Journal of Biological Chemistry* 269(10): 7764-7771). Chaperones also mediate the reversibility of pathways leading to incorrectly folded structures. One of the major complications encountered in both in vitro and in vivo protein folding is aggregation resulting from the commonly encountered low solubility of the unfolded protein or different folding intermediates. The efficiency of folding depends upon how the unfolded protein partitions between pathways leading to aggregation and pathways leading to the native structure. In vivo, the partitioning between productive and non-productive folding pathways may be influenced by "foldases" and molecular chaperones. Foldases accelerate folding by catalyzing the slow chemical steps, such as disulfide bond formation and proline isomerization that may retard folding. Molecular chaperones do not appreciably accelerate folding but bind to nonnative proteins in a way that is thought to inhibit non-productive aggregation and misfolding. In order to prevent these improper interactions, chaperones must be present at concentrations that are stoichiometric with the newly synthesized proteins. Consequently, chaperones are often found at very high concentrations in the cell.

PDI is a very abundant protein within cells. Although primarily classified as a foldase, PDI has also been shown to possess chaperone or anti-chaperone activity (Puig and Gilbert, the Journal of Biological Chemistry (1994) 269: 7764-7771). PDI accelerates lysozyme folding, and at high concentration, it displays a chaperone-like activity that prevents lysozyme misfolding and aggregation. In addition, PDI also exhibits an unusual "anti-chaperone" activity. Under conditions that favor lysozyme aggregation, low concentrations of PDI greatly reduce the yield of native lysozyme and facilitate the formation of aggregates that are extensively cross-linked by intermolecular disulfide bonds. Similarly, PDI breaks the two disulfide bonds between two insulin chains (A and B) that results in precipitation of The B chain, thus serving as an "anti-chaperone in this case." (Lundstrom J, Holmgren A (1990), "Protein disulfide-isomerase is a substrate for thioredoxin reductase and has thioredoxin-like activity". *J. Biol. Chem.* 265 (16): 9114-20).

Alpha-crystallin, a major protein component of the mammalian lens of the eye, belongs to the heat shock protein (Hsp) family and acts as a molecular chaperone by preventing aggregation of target proteins (e.g. beta and gama-crystallins) under stress conditions through the formation of stable, soluble high-molecular mass complexes with them. Aggregation of BLG (beta-lactoglobulin) occurs mainly via intermolecular disulfide bond exchange. Upon heating, BLG aggregates, which can be accelerated by subjecting the protein to either an elevated pH or through the additional of DTT. α-crystallin prevents heat-induced BLG aggregation, acting as a chaperone in the absence of DTT; in the presence of DTT, however, this chaperone activity is less efficient due to faster aggregation of heated and reduced beta-lactoglobulin. Another Hsp protein, Hsp 27, protects myosin 51 from heat-induced aggregation, but not from thermal denaturation and ATPase inactivation.

Highly sensitive fluorescent probes useful to monitoring various protein functions relating to aggregation should assist in formulation optimization. Preferably, these probes should be applicable to a broad ranges of proteins and concentrations even in the presence of excipients, salts and buffers, providing sensitive limits of detection and excellent linear dynamic ranges.

REFERENCES (1.) Andya J, Cleland J L, Hsu C C, Lam X M, Overcashier D E, Shire S J, Yang J Y-F, Wu S S-Y (2004), "Protein formulation". U.S. Pat. No. 6,685,940 B20.
(2.) Arakawa T, Philo J S, Ejima D, Sato H, Tsumoto K (2007), "Aggregation analysis of therapeutic proteins, part 3". *Bioprocess International* 5 (10): 52-70
(3.) Arakawa T, Philo J S, Ejima D, Tsumoto K, Arisaka F (2006), "Aggregation analysis of therapeutic proteins, part 1". *Bioprocess International* 4 (10): 32-42.
(4.) Arakawa T, Philo J S, Ejima D, Tsumoto K, Arisaka F (2007), "Aggregation analysis of therapeutic proteins, part 2". *Bioprocess International* 5 (4): 36-47
(5.) Demeule B, Gurny R, Arvinte T (2007), "Explorations of the application of cyanine dyes for quantitative α-synuclein detection". *International Journal of Pharmaceutics* 329: 37-45.
(6.) Ericsson U B, Hallberg B M, DeTitta G T, Dekker N, Nordlund P (2006), "Thermofluor-based high-throughput stability optimization of proteins for structural studies". *Analytical Chemistry* 357: 289-298.
(7.) Ferrari D M, Söling H D (1999), "The protein disulfide-isomerase family: unravelling a string of folds". *Biochem. J.* 339: 1-10).
(8.) Hsu C C, Nguyen H M, Wu S S (1993), "Reconstitute-able lyophilized protein formulation". U.S. Pat. No. 5,192,737.
(9.) Huang S, Oksenberg D, Urfer R (2005). "High-throughput turbidometric assay for screening inhibitors of protein disulfide isomerase activity" (U.S. Pat. No. 6,977,142 B2).
(10.) Kim S, Antwerp W P V, Gross T M, Gulati P S (2004), "Methods of evaluating protein formulation stability and surfactant-stabilized insulin formulations derived therefrom". U.S. Pat. No. 6,737,401 B2.
(11.) Krishnamurthy R, Sukumar M, Das T K, Lacher N A (2008), "Emerging analytical technologies for biotherapeutics development". *Bioprocess International* 6 (5): 32-42.
(12.) Ludvigsen S, Schein M, Boving T E G, Bonde C, Lilleore A, Engelund D K, Nielsen B R (2008), "Stable formulations of peptides". US 2008/0125361 A1.
(13.) Lundström J, Holmgren A (1990), "Protein disulfide-isomerase is a substrate for thioredoxin reductase and has thioredoxin-like activity". *J. Biol. Chem.* 265 (16): 9114-9120.
(14.) Lyles M M, Gilbert H F (1991). "Catalysis of the oxidative folding of ribonuclease A by protein disulfide isomerase: dependence of the rate on the composition of the redox buffer" *Biochemistry* 30 (3): 613-619.
(15.) Matulis D, Kranz J K, Salemme F R, Todd M J (2005), "Thermodynamic stability of carbonic anhydrase: Measurements of binding affinity and stoichiometry using thermofluor". *Biochemistry* 44: 5258-5266.
(16.) Mezzasalma T M, Kranz J K, Chan W, Struble G T, Schalk-Hihi C, Deckman I C, Springer B A, Todd M J (2007), "Enhancing recombinant protein quality and yield by protein stability profiling". *J. biomolecular screening* 12 (3): 418-428.
(17.) Pantoliano M W, Rhind A W, Salemme F R (2000), "Microplate thermal shift assay for ligand development and multivariable protein chemistry optimization". U.S. Pat. No. 6,020,141.
(18.) Puig A, Gilbert H F (1994), "Protein disulfide isomerase exhibits chaperone and anti-chaperone activity in the oxidative refoding of lysozyme". *The Journal of Biological Chemistry* 269(10): 7764-7771.
(19.) Raturi A, Mutus B (2007). "Characterization of redox state and reductase activity of protein disulfide isomerase under different redox environments using a sensitive fluorescent assay". *Free Radic. Biol. Med.* 43 (1): 62-70.
(20.) Smith A M, Chan J, Oksenberg D, Urfer R, Wexler D S, O W A, Gao L, McAlorum A, Huang S (2004). "A high-throughput turbidometric assay for screening inhibitors of protein disulfide isomerase activity". *J. Biomolecular Screening* 9 (7): 614-620)
(21.) Stefani M, Dobson C M (2003), "Protein aggregation and aggregate toxicity: new insights into protein folding, misfolding diseases and biological evolution". *J. Mol. Med.* 81: 678-699.
(22.) Todd M J, Cummings M D, Nelen M I (2005), "Affinity assays for decrypting protein targets of unknown function". *Drug discovery today: technology* 2 (3): 267-273.
(23.) Volkova K D, Kovalska V B, Balanda A O, Losytskyy My, Golub A G, Vermeij R J, Subramaniam V, Tolmachev O I, Yarmoluk S M (2008), "Specific fluorescent detection of fibrillar α-synuclein using mono- and trimethine cyanine dyes". *Bioorganic & Medicinal Chemistry* 16: 1452-1459.
(24.) Volkova K D, Kovalska V B, Balanda A O, Losytskyy My, Golub A G, Vermeij R J, Subramaniam V, Tolmachev O I, Yarmoluk S M (2008), "Specific fluorescent detection of fibrillar α-synuclein using mono- and trimethine cyanine dyes". *Bioorganic & Medicinal Chemistry* 16: 1452-1459.
(25.) Volkova K D, Kovalska V B, Balanda A O, Vermeij R J, Subramaniam V, Slominskii Y L, Yarmoluk S M (2007), "Cyanine dye-protein interactions: looking for fluorescent probes for amyloid structures". *J. Biochem. Biophys. Methods* 70: 727-733.

(26.) Volkova K D, Kovalska V B, Balanda A O, Vermeij R J, Subramaniam V, Slominskii Y L, Yarmoluk S M (2007), "Cyanine dye-protein interactions: looking for fluorescent probes for amyloid structures". *J. Biochem. Biophys. Methods* 70: 727-733).

(27.) Volkova K D, Kovalska V B, Segers-Nolten G M, Veldhuis G, Subramaniam V, Slominskii Y L, Yarmoluk S M (2009), "Detection and characterization of protein aggregates by fluorescence microscopy". *Biotechnic & Histochemistry* 84 (2): 55-61.

SUMMARY OF THE INVENTION

The present invention provides a compound comprising S25, S43, TOL3, YAT2134, YAT2148, YAT2149, S13, YAT2135 or YAT2324.

The present invention also provides a kit for assaying aggregation of a protein, comprising in packaged combination: (a) one or more compounds from FIG. 1B; and (b) instructions therefor.

This invention additionally provides a composition comprising any of the compounds from FIG. 1B or FIG. 2B, wherein said compound or compounds have been modified by the addition of a reactive group (Rx) for attachment of a target molecule thereto.

Also provided by this invention is a labeled target molecule comprising: (a) a target molecule attached to (b) any of the compounds from FIG. 1B or FIG. 2B, wherein the compound or compounds were modified by the addition of a reactive group (Rx) for attachment of the target molecule thereto.

The invention herein also provides a composition comprising a solid support to which is attached any of the compounds from FIG. 1B or FIG. 2B, wherein the compound or compounds were modified by the addition of a reactive group (Rx) for attachment of the target molecule thereto.

Additionally, this invention provides a kit for assaying aggregation of a protein, comprising in packaged combination: (a) two or more compounds, wherein one compound is from FIG. 1B and the other compound provides a higher intensity of fluorescence when measured in the presence of a protein aggregate as compared to the intensity of fluorescence when measured in the presence of a native monomeric form of the protein; and (b) instructions therefor.

The present invention provides further a kit for assaying aggregation of a protein, comprising in packaged combination: (a) two or more compounds, wherein each of the compounds provides a higher intensity of fluorescence when measured in the presence of a protein aggregate as compared to the intensity of fluorescence when measured in the presence of a native monomeric form of the protein, and wherein the emission maxima of the compounds is within 50 nanometers (nm) of each other when measured in the presence of a protein aggregate; and (b) instructions therefor.

The present invention provides yet further a multi-dye composition comprising at least three dyes, wherein each of the at least three dyes in the presence of an aggregate of the protein has a higher florescent intensity as compared to the fluorescent intensity when measured in the presence of the native monomeric form of the protein.

This invention additionally provides a compound comprising any of D95, D97, L-30, L-33, Lu-1, Lu-2, S-8, S13. S22, S25, S33, S39, S42, S43, S48, S49, SL2131, SL2592, Tio-1, TOL-2, TOL-3, TOL-5, TOL-6, TOL-7, TOL-11, YA-1, YA-3, YAT2134, YAT2135, YAT2148, YAT2149, YAT2150, YAT2213, YAT2214 or YAT2324.

Still yet provides by the present invention is a multi-dye composition comprising two or more dyes, wherein at least one of the two or more dyes comprises Dye F, Dye Fm(b), D95, D97, L-30, L-33, Lu-1, Lu-2, S-8, S13. S22, S25, S33, S39, S42, S43, S48, S49, SL2131, SL2592, Tio-1, TOL-2, TOL-3, TOL-5, TOL-6, TOL-7, TOL-11, YA-1, YA-3, YAT2134, YAT2135, YAT2148, YAT2149, YAT2150, YAT2213, YAT2214 or YAT2324.

The present invention provides a number of useful methods and processes including a method for detecting the presence of aggregates of a protein in a sample: (i) providing: (a) a sample; (b) one or more dye compounds, wherein at least one of the dye compounds comprises Dye F, Dye Fm(b), D95, D97, L-30, L-33, Lu-1, Lu-2, S-8, S13. S22, S25, S33, S39, S42, S43, S48, S49, SL2131, SL2592, Tio-1, TOL-2, TOL-3, TOL-5, TOL-6, TOL-7, TOL-11, YA-1, YA-3, YAT2134, YAT2135, YAT2148, YAT2149, YAT2150, YAT2213, YAT2214 or YAT2324; and (c) means for detecting fluorescence; (ii) forming a mixture comprising the sample (a) and the one or more dye compounds (b); and (iii) measuring the amount of fluorescence in the mixture, thereby detecting the presence of any protein aggregates in the sample.

Another method of the present invention is a method for detecting the presence of aggregates of a protein in a sample: (i) providing: (a) a sample; (b) one or more compositions having the formula

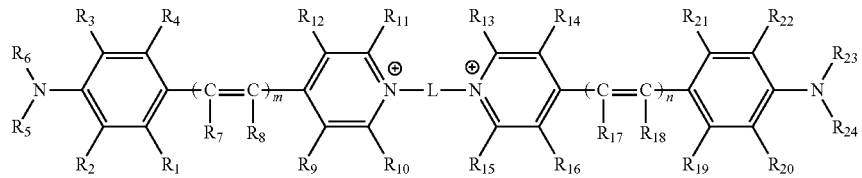

wherein m and n can independently be 1, 2 or 3; wherein L is a linker arm comprising carbon, sulfur, oxygen, nitrogen, or any combinations thereof; wherein $R_1$, $R_2$, $R_3$, $R_4$, $R_9$, $R_{10}$, $R_{11}$, $R_{12}$, $R_{13}$, $R_{14}$, $R_{15}$, $R_{16}$, $R_{19}$, $R_{20}$, $R_{21}$ and $R_{22}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken in combination $R_1$ and $R_2$, or $R_3$ and $R_4$, or $R_9$ and $R_{10}$, or $R_{11}$ and $R_{12}$, or $R_{19}$ and $R_{20}$, or $R_{21}$ and $R_{22}$ form a five or six membered ring wherein the the ring is saturated or unsaturated, substituted or unsubstituted;

wherein $R_7$, $R_8$, $R_{17}$ and $R_{18}$ can independently be hydrogen, Z, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken together, $R_7$ and $R_8$ and $R_{17}$ and $R_{18}$, may form a 5 or 6 membered ring wherein the ring is saturated or unsaturated, substituted or unsubstituted;

wherein Z comprises a carboxyl group ($CO_2^-$), a carbonate ester ($COER_{25}$), a sulfonate ($SO_3^-$), a sulfonate ester ($SO_2ER_{25}$), a sulfoxide ($SOR_{25}$), a sulfone ($SO_2CR_{25}R_{26}R_{27}$), a sulfonamide ($SO_2NR_{25}R_{26}$), a phosphate ($PO_4^=$), a phosphate monoester ($PO_3^-ER_{25}$), a phosphate diester ($PO_2ER_{25}ER_{26}$), a phosphonate ($PO_3^=$) a phosphonate monoester ($PO_2^-ER_{25}$) a phosphonate diester ($POER_{25}ER_{26}$), a thiophosphate ($PSO_3^=$), a thiophosphate monoester ($PSO_2^-ER_{25}$) a thiophosphate diester ($PSOER_{25}ER_{26}$), a thiophosphonate ($PSO_2$), a thiophosphonate monoester ($PSO^-ER_{25}$) a thiophosphonate diester ($PSER_{25}ER_{26}$), a phosphonamide ($PONR_{25}R_{26}NR_{28}R_{29}$), its thioanalogue ($PSNR_{25}R_{26}NR_{28}R_{29}$), a phosphoramide ($PONR_{25}R_{26}NR_{27}NR_{28}R_{29}$), its thioanalogue ($PSNR_{25}R_{26}NR_{27}NR_{28}R_{29}$), a phosphoramidite ($PO_2R_{25}NR_{28}R_{29}$) or its thioanalogue ($POSR_{25}NR_{28}R_{29}$) where E can be independently O or S;

wherein Z is attached directly, or indirectly through a linker arm comprising carbon, sulfur, oxygen, nitrogen, and any combinations thereof and wherein the linker arm may be saturated or unsaturated, linear or branched, substituted or unsubstituted and any combinations thereof;

wherein $R_9$, $R_{10}$, $R_{11}$, $R_{12}$, $R_{13}$, $R_{14}$, $R_{15}$ and $R_{16}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when $R_9$ and $R_{10}$ or $R_{11}$ and $R_{12}$ or $R_{13}$ and $R_{14}$ or $R_{15}$ and $R_{16}$ comprise alkyl chains that are joined together, a quinoline moiety can be formed;

wherein $R_5$, $R_6$, $R_{23}$ and $R_{24}$ can independently be hydrogen or an alkyl group wherein the alkyl group is saturated or unsaturated, linear or branched, substituted or unsubstituted, or when taken in combination $R_5$ and $R_6$ or $R_2$ and $R_5$ or $R_3$ and $R_6$ or $R_{23}$ and $R_{24}$ or $R_{22}$ and $R_{23}$ or $R_{20}$ and $R_{24}$ form a five or six membered ring wherein the ring is saturated or unsaturated, substituted or unsubstituted; and (c) means for detecting fluorescence; (ii) forming a mixture comprising the sample (a) and the one or more dye compounds (b); and (iii) measuring the amount of fluorescence in said mixture, thereby detecting the presence of any protein aggregates in said sample.

Another method provided by this invention is for detecting the formation of aggregates of a protein in a sample. This method comprises the steps of: (i) providing: (a) a sample; (b) one or more dye compounds, wherein at least one of the dye compounds comprises Dye F, Dye Fm(b), D95, D97, L-30, L-33, Lu-1, Lu-2, S-8, S13. S22, S25, S33, S39, S42, S43, S48, S49, SL2131, SL2592, Tio-1, TOL-2, TOL-3, TOL-5, TOL-6, TOL-7, TOL-11, YA-1, YA-3, YAT2134, YAT2135, YAT2148, YAT2149, YAT2150, YAT2213, YAT2214 or YAT2324; and (c) means for detecting fluorescence; (ii) forming a mixture with the sample (a) and the one or more dye compounds (b); (iii) measuring at preselected time intervals the amount of fluorescence in the mixture formed in step (ii), thereby detecting the formation of protein aggregates.

This invention also provides a method for detecting the formation of aggregates of a protein in a sample in which the method comprises the steps of: (i) providing: (a) a sample; (b) one or more compositions having the formula

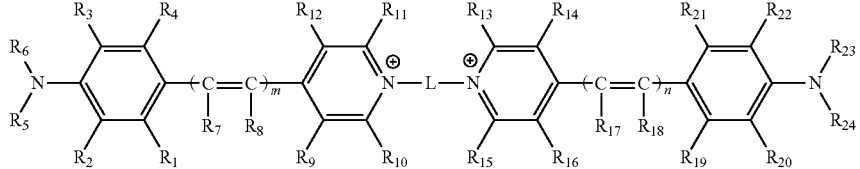

wherein m and n can independently be 1, 2 or 3; wherein L is a linker arm comprising carbon, sulfur, oxygen, nitrogen, or any combinations thereof;

wherein $R_1$, $R_2$, $R_3$, $R_4$, $R_9$, $R_{10}$, $R_{11}$, $R_{12}$, $R_{13}$, $R_{14}$, $R_{15}$, $R_{16}$, $R_{19}$, $R_{20}$, $R_{21}$ and $R_{22}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken in combination $R_1$ and $R_2$, or $R_3$ and $R_4$, or $R_9$ and $R_{10}$, or $R_{11}$ and $R_{12}$, or $R_{19}$ and $R_{20}$, or $R_{21}$ and $R_{22}$ form a five or six membered ring wherein the ring is saturated or unsaturated, substituted or unsubstituted;

wherein $R_7$, $R_8$, $R_{17}$ and $R_{18}$ can independently be hydrogen, Z, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken together, $R_7$ and $R_8$ and $R_{17}$ and $R_{18}$, may form a 5 or 6 membered ring wherein the ring is saturated or unsaturated, substituted or unsubstituted;

wherein Z comprises a carboxyl group ($CO_2^-$), a carbonate ester ($COER_{25}$), a sulfonate ($SO_3^-$), a sulfonate ester ($SO_2ER_{25}$), a sulfoxide ($SOR_{25}$), a sulfone ($SO_2CR_{25}R_{26}R_{27}$), a sulfonamide ($SO_2NR_{25}R_{26}$), a phosphate ($PO_4^-$), a phosphate monoester ($PO_3^-ER_{25}$), a phosphate diester ($PO_2ER_{25}ER_{26}$), a phosphonate ($PO_3^-$) a phosphonate monoester ($PO_2^-ER_{25}$) a phosphonate diester ($POER_{25}ER_{26}$), a thiophosphate ($PSO_3^=$), a thiophosphate monoester ($PSO_2^-ER_{25}$) a thiophosphate diester ($PSOER_{25}ER_{26}$), a thiophosphonate ($PSO_2^=$), a thiophosphonate monoester ($PSO^-ER_{25}$) a thiophosphonate diester ($PSER_{25}ER_{26}$), a phosphonamide ($PONR_{25}R_{26}NR_{28}R_{29}$), its thioanalogue ($PSNR_{25}R_{26}NR_{28}R_{29}$), a phosphoramide ($PONR_{25}R_{26}NR_{27}NR_{28}R_{29}$), its thioanalogue ($PSNR_{25}R_{26}NR_{27}NR_{28}R_{29}$), a phosphoramidite ($PO_2R_{25}NR_{28}R_{29}$) or its thioanalogue ($POSR_{25}NR_{28}R_{29}$) where E can be independently O or S;

wherein Z is attached directly, or indirectly through a linker arm comprising carbon, sulfur, oxygen, nitrogen, and any combinations thereof and wherein the linker arm may be saturated or unsaturated, linear or branched, substituted or unsubstituted and any combinations thereof;

wherein $R_9$, $R_{10}$, $R_{11}$, $R_{12}$, $R_{13}$, $R_{14}$, $R_{15}$ and $R_{16}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when $R_9$ and $R_{10}$ or $R_{11}$ and $R_{12}$ or $R_{13}$ and $R_{14}$ or $R_{15}$ and $R_{16}$ comprise alkyl chains that are joined together, a quinoline moiety can be formed;

wherein $R_5$, $R_6$, $R_{23}$ and $R_{24}$ can independently be hydrogen or an alkyl group wherein the alkyl group is saturated or unsaturated, linear or branched, substituted or unsubstituted, or when taken in combination $R_5$ and $R_6$ or $R_2$ and $R_5$ or $R_3$ and $R_6$ or $R_{23}$ and $R_{24}$ or $R_{22}$ and $R_{23}$ or $R_{20}$ and $R_{24}$ form a five or six membered ring wherein the ring is saturated or unsaturated, substituted or unsubstituted; and (c) means for detecting fluorescence; (ii) forming a mixture with the sample (a) and the one or more dye compounds (b); (iii) measuring at preselected time intervals the amount of fluorescence in the mixture formed in step (ii), thereby detecting the formation of protein aggregates.

Yet another aspect of the present invention is a method for determining whether a test compound decreases aggregation of a protein. In this aspect, the method comprises the steps of: (i) providing: (a) the protein; (b) one or more of compounds comprising Dye F, Dye Fm(b), D95, D97, L-30, L-33, Lu-1, Lu-2, S-8, S13. S22, S25, S33, S39, S42, S43, S48, S49, SL2131, SL2592, Tio-1, TOL-2, TOL-3, TOL-5, TOL-6, TOL-7, TOL-11, YA-1, YA-3, YAT2134, YAT2135, YAT2148, YAT2149, YAT2150, YAT2213, YAT2214 or YAT2324; and (c) the test compound; (ii) forming a first mixture comprising the protein (a) and the one or more compounds (b); (iii) measuring the amount of fluorescence in the first mixture at prescribed intervals; (iv) forming a second mixture comprising the protein (a), the one or more compounds (b) and the test compound (c); (v) measuring the amount of fluorescence in the second mixture at prescribed intervals; and (vi) comparing the amount of fluorescence measured in step (iii) and step (v); thereby determining whether the test compound (c) decreases the aggregation of the protein (a).

Still yet another aspect of the present invention is a method for determining whether a test compound decreases aggregation of a protein. In this aspect, the method comprises the steps of: (i) providing: (a) the protein; (b) one or more compositions having the formula the alkyl group is saturated or unsaturated, linear or branched, substituted or unsubstituted, an alkoxy group wherein the alkoxy group is saturated or unsaturated, branched or linear, substituted or unsubstituted, or when taken in combination $R_1$ and $R_2$, or $R_3$ and $R_4$, or $R_9$ and $R_{10}$, or $R_{11}$ and $R_{12}$, or $R_{19}$ and $R_{20}$, or $R_{21}$ and $R_{22}$ form a five or six membered ring wherein the ring is saturated or unsaturated, substituted or unsubstituted;

wherein $R_7$, $R_8$, $R_{17}$ and $R_{18}$ can independently be hydrogen, Z, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken together, $R_7$ and $R_8$ and $R_{17}$ and $R_{18}$, may form a 5 or 6 membered ring wherein the ring is saturated or unsaturated, substituted or unsubstituted;

wherein Z comprises a carboxyl group ($CO_2^-$), a carbonate ester ($COER_{25}$), a sulfonate ($SO_3^-$), a sulfonate ester ($SO_2ER_{25}$), a sulfoxide ($SOR_{25}$), a sulfone ($SO_2CR_{25}R_{26}R_{27}$), a sulfonamide ($SO_2NR_{25}R_{26}$), a phosphate ($PO_4^-$), a phosphate monoester ($PO_3^-ER_{c25}$), a phosphate diester ($PO_2ER_{25}ER_{26}$), a phosphonate ($PO_3^=$) a phosphonate monoester ($PO_2^-ER_{25}$) a phosphonate diester ($POER_{25}ER_{26}$), a thiophosphate ($PSO_3^=$), a thiophosphate monoester ($PSO_2^-ER_{25}$) a thiophosphate diester ($PSOER_{25}ER_{26}$), a thiophosphonate ($PSO_2^=$), a thiophosphonate monoester ($PSO^-ER_{25}$) a thiophosphonate diester ($PSER_{25}ER_{26}$), a phosphonamide ($PONR_{25}R_{26}NR_{28}R_{29}$), its thioanalogue ($PSNR_{25}R_{26}NR_{28}R_{29}$), a phosphoramide ($PONR_{25}R_{26}NR_{27}NR_{25}R_{29}$), its thioanalogue ($PSNR_{25}R_{26}NR_{27}NR_{28}R_{29}$), a phosphoramidite ($PO_2R_{25}NR_{25}R_{29}$) or its thioanalogue ($POSR_{25}NR_{25}R_{29}$) where E can be independently O or S;

wherein Z is attached directly, or indirectly through a linker arm comprising carbon, sulfur, oxygen, nitrogen, and any combinations thereof and wherein the linker arm may be saturated or unsaturated, linear or branched, substituted or unsubstituted and any combinations thereof;

wherein $R_9$, $R_{10}$, $R_{11}$, $R_{12}$, $R_{13}$, $R_{14}$, $R_{15}$ and $R_{16}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when $R_9$ and $R_{10}$ or $R_{11}$ and $R_{12}$ or $R_{13}$ and $R_{14}$ or $R_{15}$ and $R_{16}$ comprise alkyl chains that are joined together, a quinoline moiety can be formed;

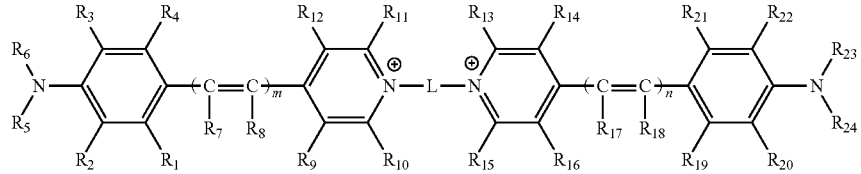

wherein m and n can independently be 1, 2 or 3;

wherein L is a linker arm comprising carbon, sulfur, oxygen, nitrogen, or any combinations thereof;

wherein $R_1$, $R_2$, $R_3$, $R_4$, $R_9$, $R_{10}$, $R_{11}$, $R_{12}$, $R_{13}$, $R_{14}$, $R_{15}$, $R_{16}$, $R_{19}$, $R_{20}$, $R_{21}$ and $R_{22}$ can independently be hydrogen, halogen, amino, ammonium, nitro, sulfo, sulfonamide, carboxy, ester, cyano, phenyl, benzyl, an alkyl group wherein wherein $R_5$, $R_6$, $R_{23}$ and $R_{24}$ can independently be hydrogen or an alkyl group wherein the alkyl group is saturated or unsaturated, linear or branched, substituted or unsubstituted, or when taken in combination $R_5$ and $R_6$ or $R_2$ and $R_5$ or $R_3$ and $R_6$ or $R_{23}$ and $R_{24}$ or $R_{22}$ and $R_{23}$ or $R_{20}$ and $R_{24}$ form a five or six membered ring wherein the ring is saturated or unsaturated, substituted or unsubstituted; (c) a test compound; and (d) means for detecting fluorescence; (ii) forming a first mixture with the protein (a) and the one or more compounds (b); (iii) measuring the amount of fluorescence in the first mixture at prescribed intervals; (iv) forming a second mixture with the protein (a), the one or more compounds (b) and the test compound to be assayed (c); (v) measuring the amount of fluorescence in the second mixture at prescribed intervals; and (vi) comparing the amount of fluorescence measured in step (iii) and step (v), thereby determining whether the test compound (c) decreases the aggregation of the protein (a).

This invention additionally provides a method for determining whether a test compound affects aggregation of a protein. In this aspect, the method comprises the steps of: (i) providing: (a) the protein; (b) two or more dyes wherein each of the dyes has a fluorescence intensity that is at least three times higher when measured in the presence of an aggregate of a protein as compared to the fluorescence intensity when measured in the presence of a native monomer of the protein; (c) a test compound; and (d) means for detection of fluorescence; (ii) forming a first mixture with the protein (a) and the two or more dyes (b); (iii) measuring the amount of fluorescence in the first mixture at prescribed intervals; (iv) forming a second mixture with the protein (a), the two or more dyes (b) and the compound to be assayed (c); (v) measuring the amount of fluorescence in the second mixture at prescribed intervals; and (vi) comparing the amount of fluorescence measured in step (iii) and step (v), thereby determining whether the test compound (c) affects aggregation of the protein.

Another method of the present invention is useful for determining whether a test compound affects aggregation of a protein, this method comprising the steps of: (i) providing: (a) the protein; (b) two or more dyes, wherein each of the two or more dyes in the presence of an aggregate of the protein has a higher florescent intensity as compared to the fluorescent intensity when measured in the presence of the native monomeric form of the protein, and wherein at least one of the dyes has the formula or unsaturated, linear or branched, substituted or unsubstituted, an alkoxy group wherein the alkoxy group is saturated or unsaturated, branched or linear, substituted or unsubstituted, or when taken together, $R_7$ and $R_8$ and $R_{17}$ and $R_{18}$, may form a 5 or 6 membered ring wherein the ring is saturated or unsaturated, substituted or unsubstituted;

wherein Z comprises a carboxyl group ($CO_2^-$), a carbonate ester ($COER_{25}$), a sulfonate ($SO_3^-$), a sulfonate ester ($SO_2ER_{25}$), a sulfoxide ($SOR_{25}$), a sulfone ($SO_2CR_{25}R_{26}R_{27}$), a sulfonamide ($SO_2NR_{25}R_{26}$), a phosphate ($PO_4^=$), a phosphate monoester ($PO_3^-ER_{25}$), a phosphate diester ($PO_2ER_{25}ER_{26}$), a phosphonate ($PO_3^=$) a phosphonate monoester ($PO_2^-ER_{25}$) a phosphonate diester ($POER_{25}ER_{26}$), a thiophosphate ($PSO_3^-$), a thiophosphate monoester ($PSO_2^-ER_{25}$) a thiophosphate diester ($PSOER_{25}ER_{26}$), a thiophosphonate ($PSO_2^=$), a thiophosphonate monoester ($PSO^-ER_{25}$) a thiophosphonate diester ($PSER_{25}ER_{26}$), a phosphonamide ($PONR_{25}R_{26}NR_{28}R_{29}$), its thioanalogue ($PSNR_{25}R_{26}NR_{28}R_{29}$), a phosphoramide ($PONR_{25}R_{26}NR_{27}NR_{25}R_{29}$), its thioanalogue ($PSNR_{25}R_{26}NR_{27}NR_{28}R_{29}$), a phosphoramidite ($PO_2R_{25}NR_{25}R_{29}$) or its thioanalogue ($POSR_{25}NR_{25}R_{29}$) where E can be independently O or S;

wherein Z is attached directly, or indirectly through a linker arm comprising carbon, sulfur, oxygen, nitrogen, and any combinations thereof and wherein the linker arm may be saturated or unsaturated, linear or branched, substituted or unsubstituted and any combinations thereof;

wherein $R_9$, $R_{10}$, $R_{11}$, $R_{12}$, $R_{13}$, $R_{14}$, $R_{15}$ and $R_{16}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when $R_9$ and $R_{10}$ or $R_{11}$ and $R_{12}$ or $R_{13}$ and $R_{14}$ or $R_{15}$ and $R_{16}$ comprise alkyl chains that are joined together, a quinoline moiety can be formed;

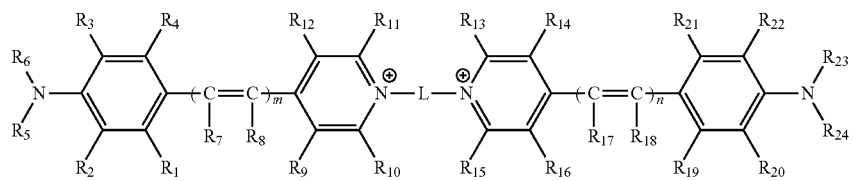

wherein m and n can independently be 1, 2 or 3;

wherein L is a linker arm comprising carbon, sulfur, oxygen, nitrogen, or any combinations thereof;

wherein $R_1$, $R_2$, $R_3$, $R_4$, $R_9$, $R_{10}$, $R_{11}$, $R_{12}$, $R_{13}$, $R_{14}$, $R_{15}$, $R_{16}$, $R_{19}$, $R_{20}$, $R_{21}$ and $R_{22}$ can independently be hydrogen, halogen, amino, ammonium, nitro, sulfo, sulfonamide, carboxy, ester, cyano, phenyl, benzyl, an alkyl group wherein said alkyl group is saturated or unsaturated, linear or branched, substituted or unsubstituted, an alkoxy group wherein the alkoxy group is saturated or unsaturated, branched or linear, substituted or unsubstituted, or when taken in combination $R_1$ and $R_2$, or $R_3$ and $R_4$, or $R_9$ and $R_{10}$, or $R_{11}$ and $R_{12}$, or $R_{19}$ and $R_{20}$, or $R_{21}$ and $R_{22}$ form a five or six membered ring wherein the ring is saturated or unsaturated, substituted or unsubstituted;

wherein $R_7$, $R_8$, $R_{17}$ and $R_{18}$ can independently be hydrogen, Z, an alkyl group wherein the alkyl group is saturated wherein $R_5$, $R_6$, $R_{23}$ and $R_{24}$ can independently be hydrogen or an alkyl group wherein the alkyl group is saturated or unsaturated, linear or branched, substituted or unsubstituted, or when taken in combination $R_5$ and $R_6$ or $R_2$ and $R_5$ or $R_3$ and $R_6$ or $R_{23}$ and $R_{24}$ or $R_{22}$ and $R_{23}$ or $R_{20}$ and $R_{24}$ form a five or six membered ring wherein the ring is saturated or unsaturated, substituted or unsubstituted; (c) a compound to be assayed; and (d) means for detecting fluorescence; (ii) forming a first mixture with the protein (a) and the two or more dyes (b); (iii) measuring the amount of fluorescence in the first mixture at prescribed intervals; (iv) forming a second mixture with the protein (a), the two or more dyes (b) and the compound to be assayed (c); (v) measuring the amount of fluorescence in the second mixture at prescribed intervals; and (vi) comparing the amount of fluorescence measured in step (iii) and step (v), thereby determining whether the test compound (c) affects aggregation of the protein.

Another method provided herein is a method for determining whether a test compound affects aggregation of a protein. Here, the method comprises the steps of: (i) providing: (a) the protein; (b) two or more dyes, wherein at least one of the dyes comprises Dye F, Dye Fm(b), D95, D97, L-30, L-33, Lu-1, Lu-2, S-8, S13. S22, S25, S33, S39, S42, S43, S48, S49, SL2131, SL2592, Tio-1, TOL-2, TOL-3, TOL-5, TOL-6, TOL-7, TOL-11, YA-1, YA-3, YAT2134, YAT2135, YAT2148, YAT2149, YAT2150, YAT2213, YAT2214 or YAT2324, and wherein each of the two or more dyes in the presence of an aggregate of the protein has a higher florescent intensity as compared to the fluorescent intensity when measured in the presence of the native monomeric form of the protein; (c) a compound to be assayed; and (d) means for detecting fluorescence; (ii) forming a first mixture with the protein (a) and the two or more dyes (b); (iii) measuring the amount of fluorescence in the first mixture at prescribed intervals; (iv) forming a second mixture with the protein (a), the two or more dyes (b) and the compound to be assayed (c); (v) measuring the amount of fluorescence in the second mixture at prescribed intervals; and (vi) comparing the amount of fluorescence measured in step (iii) and step (v), thereby determining whether the test compound (c) affects aggregation of the protein.

Also provided by the present invention is a method of determining temperature dependency of aggregation of a protein, this method comprising the steps of: (i) providing: (a) said protein; (b) two or more dyes, wherein each of the two or more dyes in the presence of an aggregate of the protein has a higher florescent intensity as compared to the fluorescent intensity when measured in the presence of the native monomeric form of the protein, and wherein at least one of the two or more dyes is selected from S13, S25, S39, S42, S43, TOL-2, TOL-3, YAT2134, YAT2135, YAT2148, YAT2149, YAT2150, YAT2213, YAT2214 and YAT2324; (c) means for detecting fluorescence; (ii) forming a first mixture with the protein (a) and the two or more dyes (b); (iii) measuring the amount of fluorescence in the first mixture at prescribed intervals; (iv) heating the first mixture and measuring the amount of fluorescence continuously or incrementally as the temperature of the first mixture is raised; (iv) comparing the measurements of fluorescence as the temperature is raised in step (iv) with the amount of fluorescence measured in step (iii), thereby determining the temperature dependency of aggregation of the protein.

The invention disclosed herein also provides a method of determining temperature dependency of aggregation of a protein. The method comprises the steps of: (i) providing: (a) the protein; (b) two or more dyes, wherein each of the two or more dyes in the presence of an aggregate of the protein has a higher florescent intensity as compared to the fluorescent intensity when measured in the presence of the native monomeric form of the protein, and wherein at least one of the dyes has the formula

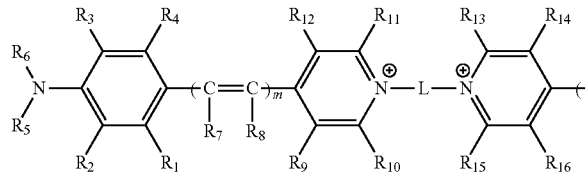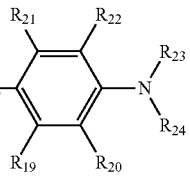

wherein m and n can independently be 1, 2 or 3;

wherein L is a linker arm comprising carbon, sulfur, oxygen, nitrogen, or any combinations thereof;

wherein $R_1$, $R_2$, $R_3$, $R_4$, $R_9$, $R_{10}$, $R_{11}$, $R_{12}$, $R_{13}$, $R_{14}$, $R_{15}$, $R_{16}$, $R_{19}$, $R_{20}$, $R_{21}$ and $R_{22}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken in combination $R_1$ and $R_2$, or $R_3$ and $R_4$, or $R_9$ and $R_{10}$, or $R_{11}$ and $R_{12}$, or $R_{19}$ and $R_{20}$, or $R_{21}$ and $R_{22}$ form a five or six membered ring wherein the ring is saturated or unsaturated, substituted or unsubstituted;

wherein $R_7$, $R_8$, $R_{17}$ and $R_{18}$ can independently be hydrogen, Z, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken together, $R_7$ and $R_8$ and $R_{17}$ and $R_{18}$, may form a 5 or 6 membered ring wherein the ring is saturated or unsaturated, substituted or unsubstituted;

wherein Z comprises a carboxyl group ($CO_2^-$), a carbonate ester ($COER_{25}$), a sulfonate ($SO_3^-$), a sulfonate ester ($SO_2ER_{25}$), a sulfoxide ($SOR_{25}$), a sulfone ($SO_2CR_{25}R_{26}R_{27}$), a sulfonamide ($SO_2NR_{25}R_{26}$), a phosphate ($PO_4^=$), a phosphate monoester ($PO_3^-ER_{25}$), a phosphate diester ($PO_2ER_{25}ER_{26}$), a phosphonate ($PO_3^=$) a phosphonate monoester ($PO_2^-ER_{25}$) a phosphonate diester ($POER_{25}ER_{26}$), a thiophosphate ($PSO_3^=$), a thiophosphate monoester ($PSO_2^-ER_{25}$) a thiophosphate diester ($PSOER_{25}ER_{26}$), a thiophosphonate ($PSO_2^=$), a thiophosphonate monoester ($PSO^-ER_{25}$) a thiophosphonate diester ($PSER_{25}ER_{26}$), a phosphonamide ($PONR_{25}R_{26}NR_{28}R_{29}$), its thioanalogue ($PSNR_{25}R_{26}NR_{28}R_{29}$), a phosphoramide ($PONR_{25}R_{26}NR_{27}NR_{28}R_{29}$), its thioanalogue ($PSNR_{25}R_{26}NR_{27}NR_{28}R_{29}$), a phosphoramidite ($PO_2R_{25}NR_{28}R_{29}$) or its thioanalogue ($POSR_{25}NR_{28}R_{29}$) where E can be independently O or S;

wherein Z is attached directly, or indirectly through a linker arm comprising carbon, sulfur, oxygen, nitrogen, and any combinations thereof and wherein the linker arm may be saturated or unsaturated, linear or branched, substituted or unsubstituted and any combinations thereof;

wherein $R_9$, $R_{10}$, $R_{11}$, $R_{12}$, $R_{13}$, $R_{14}$, $R_{15}$ and $R_{16}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when $R_9$ and $R_{10}$ or $R_{11}$ and $R_{12}$ or $R_{13}$ and $R_{14}$ or $R_{15}$ and $R_{16}$ comprise alkyl chains that are joined together, a quinoline moiety can be formed;

wherein $R_5$, $R_6$, $R_{23}$ and $R_{24}$ can independently be hydrogen or an alkyl group wherein the alkyl group is saturated or unsaturated, linear or branched, substituted or unsubstituted, or when taken in combination $R_5$ and $R_6$ or $R_2$ and $R_5$ or $R_3$ and $R_6$ or $R_{23}$ and $R_{24}$ or $R_{22}$ and $R_{23}$ or $R_{20}$ and $R_{24}$ form a five or six membered ring wherein the ring is saturated or unsaturated, substituted or unsubstituted; and (c) means for detecting fluorescence; (ii) forming a first mixture with the protein (a) and the two or more dyes (b); (iii) measuring the amount of fluorescence in the first mixture; (iv) heating the first mixture and measuring the amount of fluorescence continuously or incrementally as the temperature of the first mixture is raised; (iv) comparing the measurements of fluorescence as the temperature is in step (iv) with the amount of fluorescence measured in step (iii), thereby determining (measuring) the thermal profile of aggregation of the protein.

Also provided herein is a method of determining temperature dependency of aggregation of a protein, this method comprising the steps of: (i) providing: (a) said protein; (b) two or more dyes, wherein each of the two or more dyes in the presence of an aggregate of the protein has a higher florescent intensity as compared to the fluorescent intensity when measured in the presence of the native monomeric form of the protein, and wherein the dyes have emission maxima within 150 nm of each other in the presence of an aggregate of the protein; and (c) means for detecting fluorescence; (ii) forming a first mixture with the protein (a) and the two or more dyes (b); (iii) measuring the amount of fluorescence in the first mixture; (iv) heating the first mixture and measuring the amount of fluorescence continuously or incrementally as the temperature is raised; (iv) comparing the measurements of fluorescence in step (iv) with the amount of fluorescence measured in step (iii), thereby determining the temperature dependency of aggregation of the protein.

Another method provided by the present invention is one for measuring chaperone-like activity, the method comprising the steps of: (i) forming a reaction mixture comprising: (a) a chaperone; (b) a substrate for the chaperone; (c) one or more of compounds comprising Dye F, Dye Fm(b), D95, D97, L-30, L-33, Lu-1, Lu-2, S-8, S13. S22, S25, S33, S39, S42, S43, S48, S49, SL2131, SL2592, Tio-1, TOL-2, TOL-3, TOL-5, TOL-6, TOL-7, TOL-11, YA-1, YA-3, YAT2134, YAT2135, YAT2148, YAT2149, YAT2150, YAT2213, YAT2214 or YAT2324; (ii) exposing the reaction mixture to a stress for a period of time sufficient to induce aggregation of the substrate (b); and (iii) measuring the fluorescence intensity of the exposed mixture, wherein a decrease in the fluorescence intensity compared with the fluorescence intensity of a negative control is indicative of chaperone activity.

Still another method provided herein is one for measuring activity of a member of the thioredoxin superfamily, the method comprising the steps of: (i) forming a reaction mixture comprising: (a) a member of the thioredoxin superfamily; (b) a substrate for the member of the thioredoxin superfamily; (c) a reducing agent; and (d) one or more of compounds comprising Dye F, Dye Fm(b), D95, D97, L-30, L-33, Lu-1, Lu-2, S-8, S13. S22, S25, S33, S39, S42, S43, S48, S49, SL2131, SL2592, Tio-1, TOL-2, TOL-3, TOL-5, TOL-6, TOL-7, TOL-11, YA-1, YA-3, YAT2134, YAT2135, YAT2148, YAT2149, YAT2150, YAT2213, YAT2214 or YAT2324; (ii) incubating the reaction mixture for a period of time sufficient to reduce disulfide bonds in the substrate; and (iii) measuring the fluorescence intensity of the mixture, wherein an increase in the fluorescence intensity compared with the fluorescence intensity of a negative control is indicative of activity of the member of the thioredoxin superfamily.

The present invention yet provides another method for separating aggregates of proteins from monomeric forms of the proteins. In this method, steps are carried out comprising: (i) providing: (a) a sample having aggregates of the proteins and monomeric forms of said proteins; (b) one or more of compounds, wherein at least one of the compounds is selected from Dye F, Dye Fm(b), D95, D97, L-30, L-33, Lu-1, Lu-2, S-8, S13. S22, S25, S33, S39, S42, S43, S48, S49, SL2131, SL2592, Tio-1, TOL-2, TOL-3, TOL-5, TOL-6, TOL-7, TOL-11, YA-1, YA-3, YAT2134, YAT2135, YAT2148, YAT2149, YAT2150, YAT2213, YAT2214 and YAT2324, and wherein the one or more compounds are attached to a solid matrix; (ii) forming under binding conditions a mixture with the sample (a) and the one or more dyes (b) to allow binding between the one or more compounds (b) and any aggregates of the proteins in the sample (a); and (iii) separating unbound proteins from the aggregates bound to the one or more compounds (a) in step (ii).

Another method provided herein is for separating aggregates of proteins from monomeric forms of the proteins. Here, the method comprises the steps of: (i) providing: (a) a sample that having aggregates of the proteins and monomeric forms of the proteins; (b) two or more dyes, wherein each of the two or more dyes in the presence of an aggregate of the protein has a higher florescent intensity as compared to the fluorescent intensity when measured in the presence of the native monomeric form of the protein, and wherein at least one of the dyes has the formula

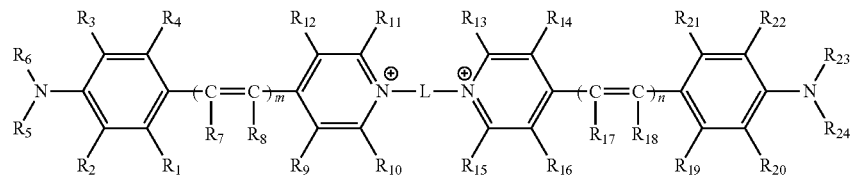

wherein m and n can independently be 1, 2 or 3;

wherein L is a linker arm comprising carbon, sulfur, oxygen, nitrogen, or any combinations thereof;

wherein $R_1$, $R_2$, $R_3$, $R_4$, $R_9$, $R_{10}$, $R_{11}$, $R_{12}$, $R_{13}$, $R_{14}$, $R_{15}$, $R_{16}$, $R_{19}$, $R_{20}$, $R_{21}$ and $R_{22}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken in combination $R_1$ and $R_2$, or $R_3$ and $R_4$, or $R_9$ and $R_{10}$, or $R_{11}$ and $R_{12}$, or $R_{19}$ and $R_{20}$, or $R_{21}$ and $R_{22}$ form a five or six membered ring wherein the ring is saturated or unsaturated, substituted or unsubstituted;

wherein $R_7$, $R_8$, $R_{17}$ and $R_{18}$ can independently be hydrogen, Z, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken together, $R_7$ and $R_8$ and $R_{17}$ and $R_{18}$, may form a 5 or 6 membered ring wherein the ring is saturated or unsaturated, substituted or unsubstituted;

wherein Z comprises a carboxyl group ($CO_2^-$), a carbonate ester ($COER_{25}$), a sulfonate ($SO_3^-$), a sulfonate ester ($SO_2ER_{25}$), a sulfoxide ($SOR_{25}$), a sulfone ($SO_2CR_{25}R_{26}R_{27}$), a sulfonamide ($SO_2NR_{25}R_{26}$), a phosphate ($PO_4^=$), a phosphate monoester ($PO_3^-ER_{25}$), a phosphate diester ($PO_2ER_{25}ER_{26}$), a phosphonate ($PO_3^=$) a phosphonate monoester ($PO_2^-ER_{25}$) a phosphonate diester ($POER_{25}ER_{26}$), a thiophosphate ($PSO_3^=$), a thiophosphate monoester ($PSO_2^-ER_{25}$) a thiophosphate diester ($PSOER_{25}ER_{26}$), a thiophosphonate ($PSO_2^=$), a thiophosphonate monoester ($PSO^-ER_{25}$) a thiophosphonate diester ($PSER_{25}ER_{26}$), a phosphonamide ($PONR_{25}R_{26}NR_{28}R_{29}$), its thioanalogue ($PSNR_{25}R_{26}NR_{28}R_{29}$), a phosphoramide ($PONR_{25}R_{26}NR_{27}NR_{28}R_{29}$), its thioanalogue ($PSNR_{25}R_{26}NR_{27}NR_{28}R_{29}$), a phosphoramidite ($PO_2R_{25}NR_{28}R_{29}$) or its thioanalogue ($POSR_{25}NR_{28}R_{29}$) where E can be independently O or S;

wherein Z is attached directly, or indirectly through a linker arm comprising carbon, sulfur, oxygen, nitrogen, and any combinations thereof and wherein the linker arm may be saturated or unsaturated, linear or branched, substituted or unsubstituted and any combinations thereof;

wherein $R_9$, $R_{10}$, $R_{11}$, $R_{12}$, $R_{13}$, $R_{14}$, $R_{15}$ and $R_{16}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when $R_9$ and $R_{10}$ or $R_{11}$ and $R_{12}$ or $R_{13}$ and $R_{14}$ or $R_{15}$ and $R_{16}$ comprise alkyl chains that are joined together, a quinoline moiety can be formed;

wherein $R_5$, $R_6$, $R_{23}$ and $R_{24}$ can independently be hydrogen or an alkyl group wherein the alkyl group is saturated or unsaturated, linear or branched, substituted or unsubstituted, or when taken in combination $R_5$ and $R_6$ or $R_2$ and $R_5$ or $R_3$ and $R_6$ or $R_{23}$ and $R_{24}$ or $R_{22}$ and $R_{23}$ or $R_{20}$ and $R_{24}$ form a five or six membered ring wherein the ring is saturated or unsaturated, substituted or unsubstituted; and, and wherein at least of the one or more compounds is attached to a solid support; (ii) forming under binding conditions a mixture with the sample (a) and the one or more dyes (b) to allow binding between the one or more compounds (b) and any aggregates of the proteins in the sample (a); and (iii) separating unbound proteins from the aggregates bound to the one or more compounds (a) in step (ii).

BRIEF DESCRIPTION OF THE FIGURES

FIGS. 1A and 1B show a group of compounds that exhibit a ratio of 3 or more for fluorescence from binding to aggregates compared to being in the presence of monomeric forms.

FIGS. 2A and 2B show a group of compounds that exhibit a ratio of less than 3 for fluorescence from binding to aggregates compared to being in the presence of monomeric forms.

DESCRIPTION OF THE INVENTION

Figure 1B:
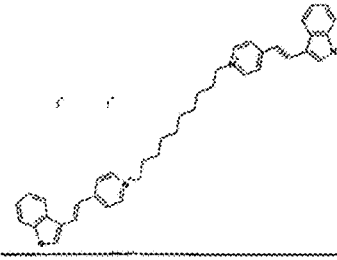
Figure 1B:
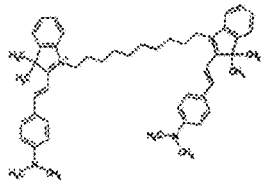
Figure 1B:
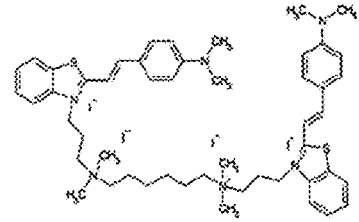
Figure 1B:
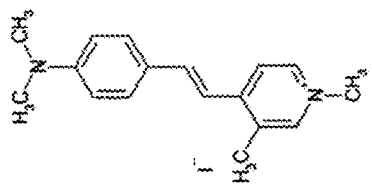
Figure 1B:
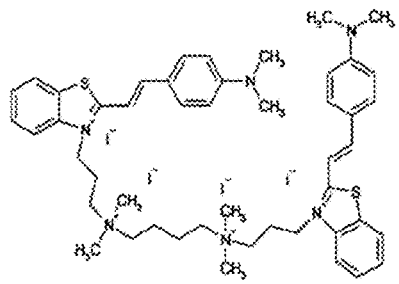
Figure 1B:
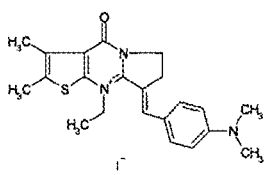
Figure 1B:
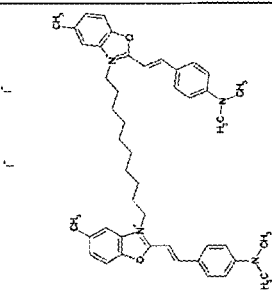
Figure 1B:
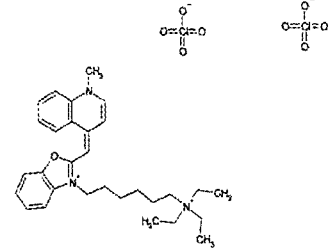
Figure 1B:
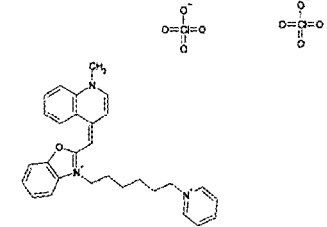
Figure 1B:
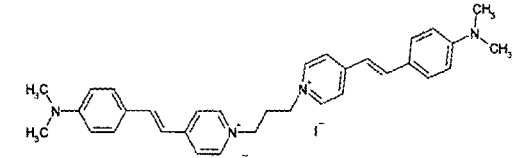
Figure 1B:
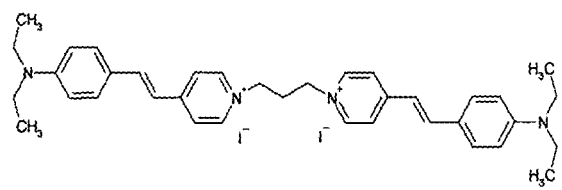

The present invention provides dyes, reagents and methods that may be used in the detection of protein aggregates; screening assays for compounds that promote or inhibit protein aggregation; establishment of storage formulations that prevent or decrease protein aggregation; screening assays for chaperone activity or compounds that affect chaperone activity. Many of the disclosed dyes may be used free in solution where the binding of the dye to the target molecule provides an increase in fluorescence intensity. The methods and compositions of the present invention satisfy needs for protein aggregation detection with fluorescent probes that provide desirable detection limits and dynamic ranges, excellent sensitivity and linearity for both in vivo and in vitro applications in medicine and the biotechnology field. The present invention further provides a family of cell-permeable organic probes that shows multi-fold fluorescence intensity enhancement upon binding specifically to the aggregated form of the protein, while remaining minimally fluorescent in the presence of the native form of the protein.

The present invention relates to the use of a family of dimeric styryl dyes containing either a picoline or lepidine ring and a dialkyl amino or alkyloxy substituent. The dyes of the invention are useful for generating fluorescence signals that depend upon the presence of an aggregated form of a protein, while conveying minimal levies of signals when only the native form of the protein is present. A number of novel dimeric styryl dyes having these properties are also disclosed.

The present invention also provides a method of: monitoring formation of protein aggregates; identifying storage formulations for proteins that prevent aggregation; screening compounds that promote or inhibit protein aggregation or measuring molecular chaperone activity, comprising the first step (A) of providing (i) the proteins of interest; and (ii) dimeric styryl dyes and/or other useful dyes, followed by incubating (B) the proteins of interest (i) with the compound(s) (ii) and monitoring the presence of aggregates or the formation of aggregates using by various fluorescence detection techniques known in the art.

Methods and kits are also provided for a real-time assay of PDI isomerase activity, as well as chaperone activity. This assay can be employed to: screen chemical libraries for small molecule inhibitors of chaperone; and for monitoring chaperone activity in clinical situations, for example in hypoxia. One method is based upon enzyme-catalyzed reduction of insulin in the presence of dithiothreitol; measuring the aggregation of reduced insulin B chain by exogenously added protein aggregation detection dyes of the invention in a real-time manner. This provides a sensitive, high throughput, real-time assay that is more robust and cost-effective than standard turbidity-based methods.

In another embodiment of the present invention, dimeric styryl dyes comprise a reactive group, thereby allowing their attachment to targets of interest. As such, a method of covalently labeling target molecules is disclosed comprising the steps of (a) providing: (i) a sample containing such target molecules; and (ii) a dimeric styryl dye, comprising at least one reactive group; and (b) attaching any of the compound or compounds (ii) by means of the reactive group to the target molecules in the sample (i), thereby labeling the target molecules.

Also provided by this invention is kits for monitoring formation of protein aggregates, for finding storage formulations of proteins that prevent aggregation, for screening of compounds that promote or inhibit protein aggregation and for sensitive measurement of molecular chaperone activity. The kits may contain in packaged combination the following components or elements: (A) any of the aforementioned compounds or mixtures of compounds, (B) controls containing positive and negative controls such as native and aggregated forms of a protein (C) optional buffers; and (D) instructions or a protocol for recommended use of the kit.

The complex properties of protein aggregation and amyloid formation require development of sophisticated yet operationally simple techniques which can provide detection as well as direct readout of structural changes in protein assemblies, such as the response of proteins to the addition of ligands, chaotropes and/or excipients. The invention additionally relates to methods for testing stabilizers of monomeric proteins as well as inhibitors of protein aggregation in order to provide formulations of proteins that are resistant to aggregation. The present invention further relates to the design of fluorescent probes for the imaging and diagnosis of a disease in which neurofibrillary tangles accumulate, as exemplified by the detection of senile plaques in the brain tissue of patients suffering from Alzheimer's disease. Finally, the invention relates to the assay of enzymes and proteins that alter the aggregation state of proteins.

Basic Fluorophore Core Structure:

Among the various aspects of the present invention, a number of probes are disclosed that are based on dimeric styryl dye chromophores containing a lepidine or picoline ring, forming symmetrical and asymmetrical canine dyes. Some of these dyes have been described previously in the context of binding to nucleic acids, but it has been discovered that many of these dyes demonstrate a useful property where an enhanced level of fluorescence is produced after binding to aggregated forms of proteins compared to the level that is emitted in the presence of the native forms. Some of these dyes also exhibit large Stokes shifts between their absorption and emission wavelength optima thereby increasing the ease of detection.

The dyes of the present invention can be modified by the addition of charged groups, as exemplified by sulfonates, phosphates, phosphonates and their derivatives and/or polar groups as exemplified by sulfoxide, sulfone and sulfonamide moieties. It is also understood that when a dye comprises an anionic group, there will also be a cationic counterion present. Any cation may serve this purpose as long as it doesn't interfere with the use of the dye. Examples of cations that may serve as counterions can include but are not limited to hydrogen, sodium, potassium, lithium, calcium, cesium, ammonium, alkyl ammonium, alkoxy ammonium and pyridinium. It is also understood that when a dye comprises a cationic group, there will also be an anionic counterion present. Any anion may serve this purpose as long as it doesn't interfere with the use of the dye. Examples of anions that may serve as counterions can include but not be limited to perchlorate ($ClO_4^-$), sulfate ($SO_4^=$), sulfonate, alkane sulfonate, aryl sulfonate, phosphate, tosylate, mesylate and tetrafluoroborate moieties and halides such as a bromide, chloride, fluoride and iodide. In some cases the counterion or counterions are provided by the dye being a salt where they exist as separate ionic species. In other cases, the counterion or counterions may be present as part of the compound (sometimes called inner salts). It is understood that there may also be a combination of ions that are provided by the compound and salts. With regard to acid moieties that are shown in forms such as COOH it is also understood that these compounds may be found in ionized forms such as $COO^-$.

It should also be appreciated by those skilled in the art that the stoichiometric number of counterion or counterions which balance the charge or charges on the compound can be the same or they can be different provided that the counterions balance the charge(s) on the compound. The combination of counterions can be selected from any of the above mentioned anions. This applies for the combination of cations also.

It should be further appreciated by those skilled in the art that the foregoing descriptions of the anions and their stoichiometric number and/or combination are applicable to the compounds and dyes of the present invention, and to methods which use these compounds and dyes.

Alkyl or alkoxy R groups may be substituted or unsubstituted. Examples of substitutions can include but are not limited to one or more fluorine, chlorine, bromine, iodine, hydroxy, carboxy, carbonyl, amino, cyano, nitro or azido groups as well as other alkyl or alkoxy groups. The length of the alkoxy groups may be as desired. For instance, they may independently comprise from 1 to 18 carbons in length. They may be shorter as well, for instance they may be only 1 to 6 carbons in length in a dye molecule of the present invention.

The polar groups, charged groups and other substituents may be connected to the dye directly or they may be connected by a linker arm comprising carbon, nitrogen, sulfur, oxygen or any combination thereof. The linker arm may be saturated or unsaturated, linear or branched, substituted or unsubstituted as well as any combination of the foregoing.

Among the useful dyes of the present invention are styryl cyanine dye chromophores having the general formula:

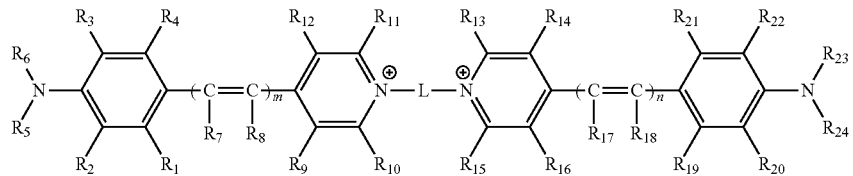

wherein m and n can independently be 1, 2 or 3;

wherein L is a linker arm comprising carbon, sulfur, oxygen, nitrogen, or any combinations thereof;

wherein $R_1$, $R_2$, $R_3$, $R_4$, $R_9$, $R_{10}$, $R_{11}$, $R_{12}$, $R_{13}$, $R_{14}$, $R_{15}$, $R_{16}$, $R_{19}$, $R_{20}$, $R_{21}$ and $R_{22}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken in combination $R_1$ and $R_2$, or $R_3$ and $R_4$, or $R_9$ and $R_{10}$, or $R_{11}$ and $R_{12}$, or $R_{19}$ and $R_{20}$, or $R_{21}$ and $R_{22}$ form a five or six membered ring wherein the ring is saturated or unsaturated, substituted or unsubstituted;

wherein $R_7$, $R_8$, $R_{17}$ and $R_{18}$ can independently be hydrogen, Z, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken together, $R_7$ and $R_8$ and $R_{17}$ and $R_{18}$, may form a 5 or 6 membered ring wherein the ring is saturated or unsaturated, substituted or unsubstituted;

wherein Z comprises a carboxyl group ($CO_2^-$), a carbonate ester ($COER_{25}$), a sulfonate ($SO_3^-$), a sulfonate ester ($SO_2ER_{25}$), a sulfoxide ($SOR_{25}$), a sulfone ($SO_2CR_{25}R_{26}R_{27}$), a sulfonamide ($SO_2NR_{25}R_{26}$), a phosphate ($PO_4^=$), a phosphate monoester ($PO_3^-ER_{25}$), a phosphate diester ($PO_2ER_{25}ER_{26}$), a phosphonate ($PO_3^=$) a phosphonate monoester ($PO_2^-ER_{25}$) a phosphonate diester ($POER_{25}ER_{26}$), a thiophosphate ($PSO_3^=$), a thiophosphate monoester ($PSO_2^-ER_{25}$) a thiophosphate diester ($PSOER_{25}ER_{26}$), a thiophosphonate ($PSO_2^=$), a thiophosphonate monoester ($PSO^-ER_{25}$) a thiophosphonate diester ($PSER_{25}ER_{26}$), a phosphonamide ($PONR_{25}R_{26}NR_{28}R_{29}$), its thioanalogue ($PSNR_{25}R_{26}NR_{28}R_{29}$), a phosphoramide ($PONR_{25}R_{26}NR_{27}NR_{28}R_{29}$), its thioanalogue ($PSNR_{25}R_{26}NR_{27}NR_{28}R_{29}$), a phosphoramidite ($PO_2R_{25}NR_{28}R_{29}$) or its thioanalogue ($POSR_{25}NR_{28}R_{29}$) where E can be independently O or S;

wherein Z is attached directly, or indirectly through a linker arm comprising carbon, sulfur, oxygen, nitrogen, and any combinations thereof and wherein the linker arm may be saturated or unsaturated, linear or branched, substituted or unsubstituted and any combinations thereof;

wherein $R_9$, $R_{10}$, $R_{11}$, $R_{12}$, $R_{13}$, $R_{14}$, $R_{15}$ and $R_{16}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when $R_9$ and $R_{10}$ or $R_{11}$ and $R_{12}$ or $R_{13}$ and $R_{14}$ or $R_{15}$ and $R_{16}$ comprise alkyl chains that are joined together, a quinoline moiety can be formed;

wherein $R_5$, $R_6$, $R_{23}$ and $R_{24}$ can independently be hydrogen or an alkyl group wherein the alkyl group is saturated or unsaturated, linear or branched, substituted or unsubstituted, or when taken in combination $R_5$ and $R_6$ or $R_2$ and $R_5$ or $R_3$ and $R_6$ or $R_{23}$ and $R_{24}$ or $R_{22}$ and $R_{23}$ or $R_{20}$ and $R_{24}$ form a five or six membered ring wherein the ring is saturated or unsaturated, substituted or unsubstituted.

In many instances, the dyes of the invention are symmetric dimers, such that substitutents on the left side outer ring are also present on the right side inner ring and a similar relationship exists with the left and right inner rings as well.

For all dyes on the invention, any net positive or negative charges possessed by the dye are balanced by a biologically compatible counterion or counterions as discussed above.

Among preferred dyes of the present invention are any and all of those comprising S25, S43, TOL3, YAT2134, YAT2148, YAT2149, S13, YAT2135 or YAT2324. The foregoing dyes are listed in FIG. 1A.

This invention also provides a multi-dye composition comprising at least three dyes, wherein each of the at least three dyes in the presence of an aggregate of the protein has a higher florescent intensity as compared to the fluorescent intensity when measured in the presence of the native monomeric form of the protein.

This invention further provides a compound comprising any of D95, D97, L-30, L-33, Lu-1, Lu-2, S-8, S13. S22, S25, S33, S39, S42, S43, S48, S49, SL2131, SL2592, Tio-1, TOL-2, TOL-3, TOL-5, TOL-6, TOL-7, TOL-11, YA-1, YA-3, YAT2134, YAT2135, YAT2148, YAT2149, YAT2150, YAT2213, YAT2214 or YAT2324. These dye compounds are listed in FIG. 1A together with corresponding emission characteristics and other properties.

Also provided by the invention herein is a multi-dye composition comprising two or more dyes, wherein at least one of the two or more dyes comprises Dye F, Dye Fm(b), D95, D97, L-30, L-33, Lu-1, Lu-2, S-8, S13. S22, S25, S33, S39, S42, S43, S48, S49, SL2131, SL2592, Tio-1, TOL-2, TOL-3, TOL-5, TOL-6, TOL-7, TOL-11, YA-1, YA-3, YAT2134, YAT2135, YAT2148, YAT2149, YAT2150, YAT2213, YAT2214 or YAT2324. Again, the foregoing dye compounds are listed in FIG. 1A together with other characteristics and properties.

Among useful kits of the present invention is a kit for assaying aggregation of a protein. This kit comprises in packaged combination: (a) one or more compounds from FIG. 1B; and (b) instructions therefor. Such a kit may further comprise (c) buffers; or (d) positive controls; or (e) negative controls, or (f) a combination of any of the foregoing. Additional instructions therefor are available for this kit. The aforementioned positive controls comprise protein aggregates and the negative controls comprise protein monomers. A microplate or a microarray may also be included in the kit.

Complex Ring Structures

As described above some of the R groups may be joined together to form one or more fused 5 or 6 membered ring structures. It is understood that the complex rings that are formed by closure of R groups may be further substituted with any of the R groups described previously. Examples of complex rings that may be formed for the picoline or lepidine portion of the cyanine dyes of the invention can comprise but not be limited to:

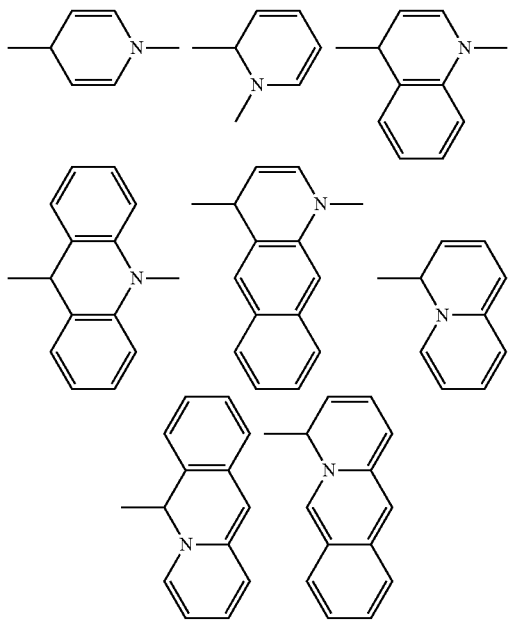

Examples of rings and complex rings that may be part of the styryl portion of the dye can comprise but not be limited to:

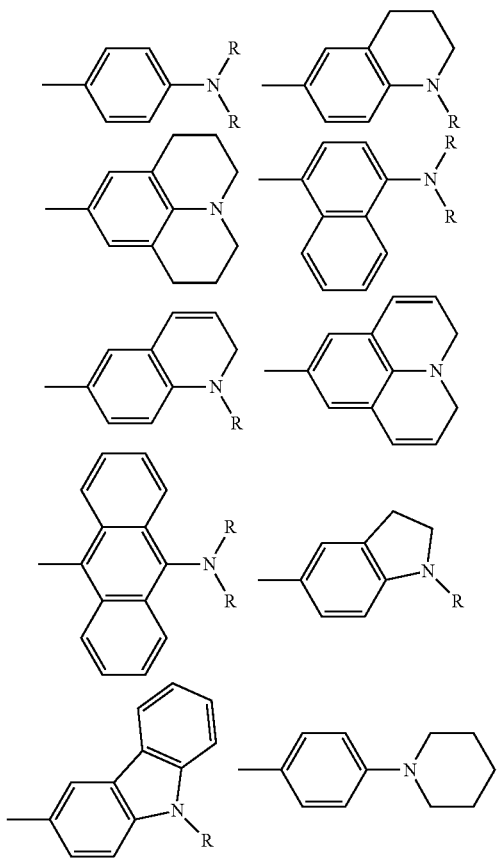

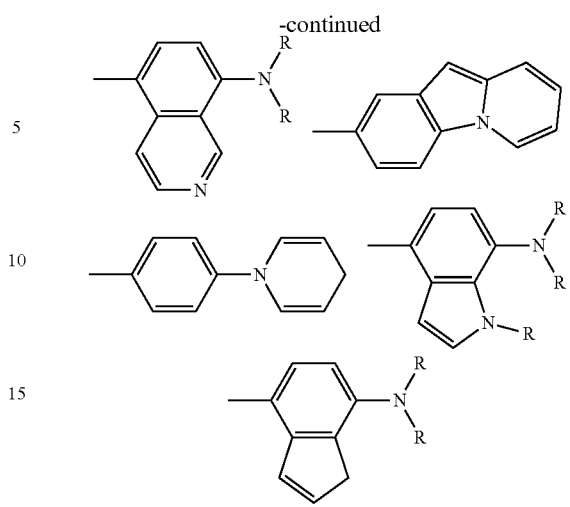

Reactive Groups and Targets

In another aspect of the present invention, advantage is taken of the large Stokes shift that some other these dyes enjoy, thereby making them suitable as labels of selected target molecules. For this particular application, one of the R groups is a reactive group thereby allowing the dyes of the present invention to be attached to a useful target molecule or solid-phase support. Examples of reactive groups that may find use in the present invention can include but not be limited to a nucleophilic reactive group, an electrophilic reactive group, a terminal alkene, a terminal alkyne, a platinum coordinate group or an alkylating agent.

There are a number of different electrophilic reactive groups that may find use with the present invention; examples can include but not be limited to isocyanate, isothiocyanate, monochlorotriazine, dichlorotriazine, 4,6,-dichloro-1,3,5-triazines, mono- or di-halogen substituted pyridine, mono- or di-halogen substituted diazine, maleimide, haloacetamide, aziridine, sulfonyl halide, acid halide, hydroxysuccinimide ester, hydroxysulfosuccinimide ester, imido ester, hydrazine, azidonitrophenol, azide, 3-(2-pyridyl dithio)-propionamide, glyoxal and aldehyde groups. Nucleophilic reactive groups can include but not be limited to reactive thiol, amine and hydroxyl groups. For purposes of synthesis of dyes, reactive thiol, amine or hydroxyl groups can be protected during various synthetic steps and the reactive groups generated after removal of the protective group. Use of a terminal alkene or alkyne groups for attachment of markers has been previously described in U.S. Patent Application Serial No. 2003/0225247, hereby incorporated by reference. The use of platinum coordinate groups for attachment of other dyes has been previously disclosed in U.S. Pat. No. 5,580,990 and the use of alkyl groups has been previously described in U.S. Pat. No. 6,593,465 B1, both of which patents are hereby incorporated by reference. In some cases the molecules that have been disclosed already have a suitable group that can be used as a reactive group; in other cases standard chemical manipulations can be used to modify a dye to comprise a desired reactive group.

Figure 2B:
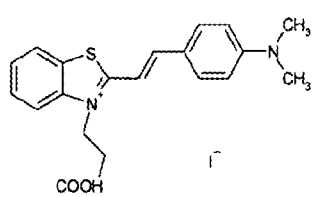
Figure 2B:
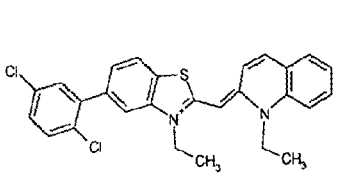
Figure 2B:
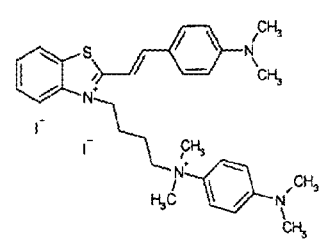
Figure 2B:
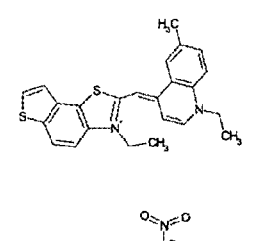
Figure 2B:
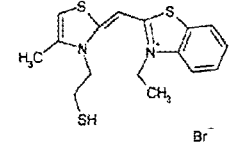
Figure 2B:
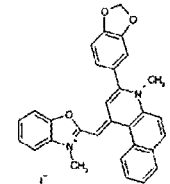
Figure 2B:
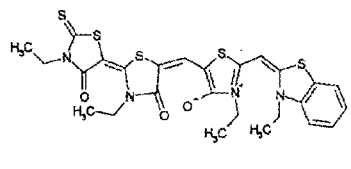
Figure 2B:
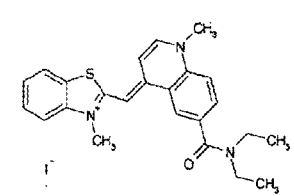
Figure 2B:
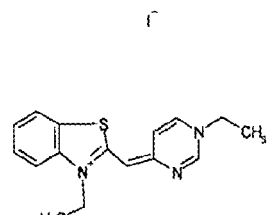
Figure 2B:
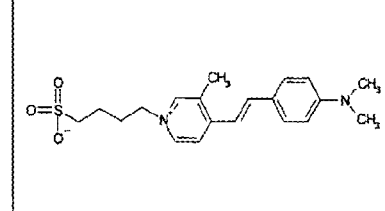

Thus, the present invention provides a composition comprising any of the compounds from FIG. 1B or FIG. 2B, wherein such compound or compounds have been modified by the addition of a reactive group (Rx) for attachment of a target molecule thereto. The reactive group (Rx) comprises an electrophilic reactive group comprising isocyanate, isothiocyanate, monochlorotriazine, dichlorotriazine, 4,6,-dichloro-1,3,5-triazines, mono- or di-halogen substituted pyridine, mono- or di-halogen substituted diazine, maleimide, haloacetamide, aziridine, sulfonyl halide, acid halide, hydroxysuccinimide ester, hydroxysulfosuccinimide ester, imido ester, hydrazine, azidonitrophenol, azide, 3-(2-pyridyl dithio)-propionamide, glyoxal or aldehyde groups, and a combination of any of the foregoing. In another embodiment, the reactive group (Rx) comprises a nucleophilic reactive group comprising reactive thiol, amine or hydroxyl, and a combination of the foregoing. In other aspects, the reactive group (Rx) comprises a terminal alkene group, a terminal alkyne group, a nickel coordinate group or a platinum coordinate group for attachment. The reactive group (Rx) can be attached to the compound through a linker arm.

Another aspect of the present invention is a labeled target molecule comprising: (a) a target molecule attached to (b) any of the compounds from FIG. 1B or FIG. 2B, wherein the compound or compounds were modified by the addition of a reactive group (Rx) for attachment of the target molecule thereto. Such a target molecule comprises a large number of different forms, including a nucleoside, a nucleotide, an oligonucleotide, a polynucleotide, a peptide nucleic acid, a protein, a peptide, an enzyme, an antigen, an antibody, a hormone, a hormone receptor, a cellular receptor, a lymphokine, a cytokine, a hapten, a lectin, avidin, streptavidin, digoxigenin, a carbohydrate, an oligosaccharide, a polysaccharide, a lipid, a liposomes, a glycolipid, a viral particle, a viral component, a bacterial cell, a bacterial component, a eukaryotic cell, a eukaryotic cell component, a natural drug or synthetic drug, and combinations of any of the foregoing.

The reactive group for attachment of the target molecule to such compounds from FIG. 1B or FIG. 2B comprise an electrophilic reactive group comprising isocyanate, isothiocyanate, monochlorotriazine, dichlorotriazine, 4,6,-dichloro-1,3,5-triazines, mono- or di-halogen substituted pyridine, mono- or di-halogen substituted diazine, maleimide, haloacetamide, aziridine, sulfonyl halide, acid halide, hydroxysuccinimide ester, hydroxysulfosuccinimide ester, imido ester, hydrazine, azidonitrophenol, azide, 3-(2-pyridyl dithio)-propionamide, glyoxal or aldehyde groups, a nucleophilic reactive group comprising reactive thiol, amine or hydroxyl, a nickel coordinate group, a platinum coordinate group, a terminal alkene or a terminal alkyne, and any combination of the foregoing. A linker arm can be positioned between the compound and the reactive group, or between the target molecule and the reactive group.

Examples of useful target molecules and solid-phase supports can include but are not limited to a nucleoside, nucleotide, oligonucleotide, polynucleotide, peptide nucleic acid, protein, peptide, enzyme, antigen, antibody, hormone, hormone receptor, cellular receptor, lymphokine, cytokine, hapten, lectin, avidin, strepavidin, digoxygenin, carbohydrate, oligosaccharide, polysaccharide, lipid, liposomes, glycolipid, viral particle, viral component, bacterial cell, bacterial component, eucaryotic cell, eukaryotic cell component, natural drug, synthetic drug, glass particle, glass surface, natural polymers, synthetic polymers, plastic particle, plastic surface, silicaceous particle, silicaceous surface, organic molecule, dyes and derivatives thereof.

The nucleoside, nucleotide, oligonucleotide, or polynucleotide can comprise one or more ribonucleoside moieties, ribonucleotide moieties, deoxyribonucleoside moieties, deoxyribonucleotide moieties, modified ribonucleosides, modified ribonucleotides, modified deoxyribonucleosides, modified deoxyribonucleotides, ribonucleotide analogues, deoxyribonucleotide analogues and any combination thereof.

As described above, the dyes of the present invention may have dyes as targets thereby creating composite dyes. By joining the dyes of the present invention to another dye, unique properties may be enjoyed that are not present in either dye alone. For instance, if one of the dyes of the present invention is joined to another dye such that it creates an extended conjugation system, the spectral characteristics of the dye may be different than either dye component. Another example of this method is where the conjugation systems do not overlap but the proximity allows an internal energy transfer to take place thereby extending the Stokes shift, a system that is commonly referred to as FRET (Fluorescent Resonance Energy Transfer) or Energy Transfer in short. For an example of this, see U.S. Pat. No. 5,401,847, U.S. Pat. No. 6,008,373 B1 and U.S. Pat. No. 5,800,996, all three of which patents are hereby incorporated by reference. Other properties may also be enhanced by this joining; for example, it has been previously described that the joining together of two ethidium bromide molecules generates a dye that has enhanced binding to nucleic acids and novel fluorescent properties that are different from the monomeric forms (U.S. Patent Application Publication No. 2003/0225247, hereby incorporated by reference). Other composite dyes have been described that simultaneously enjoy both properties, i.e., enhanced binding and energy transfer (U.S. Pat. No. 5,646,264, hereby incorporated by reference). Furthermore, these composites dyes are not limited to binary constructs of only two dyes, but may comprise oligomeric or polymeric dyes. These composite dyes may be comprised of the same dye or different dyes may be joined together depending upon the properties desired.

Utility may also be achieved by attaching a dye of the present invention to a target specific moiety. Thus, binding between the target specific moiety and its corresponding target may be monitored by essentially determining the presence or amount of dye that is bound to the target. Well-known examples of such assays are hybridizations between complementary nucleic acids as well as binding that take place between antibodies and their corresponding antigens. Other binding pairs that may be of interest can include but not be limited to ligand/receptor, hormone/hormone receptor, carbohydrate/lectin and enzyme/substrate. Assays may be carried out where one component is fixed to a solid-phase support and a corresponding partner is in solution. By binding to the component fixed to the support, the partner now becomes attached to the support as well. A well-known example of this method is the microarray assays where labeled analytes become bound to discrete sites on the microarray. Homogeneous probe dependent assays are also well known in the art and may take advantage of the present invention. Examples of such methods are energy transfer between adjacent probes (U.S. Pat. No. 4,868,103), the Taqman exonuclease assay (U.S. Pat. No. 5,538,848 and U.S. Pat. No. 5,210,015), Molecular Beacons (U.S. Pat. No. 5,118,801 and U.S. Pat. No. 5,925,517) and various real time assays (U.S. patent application Ser. No. 10/096,076), all of which are incorporated by reference.

In other aspects, this invention provides a composition comprising a solid support to which is attached any of the compounds from FIG. 1B or FIG. 2B, wherein the compound or compounds were modified by the addition of a reactive group (Rx) for attachment of the target molecule thereto. The solid support comprises glass particle, glass surface, natural polymers, synthetic polymers, plastic particle, plastic surface, silicaceous particle, silicaceous surface, glass, plastic or latex beads, controlled pore glass, metal particle, metal oxide particle, microplate or microarray, and combinations of any of the foregoing. The aforementioned reactive group for attachment comprises or may have comprised an electrophilic reactive group comprising isocyanate, isothiocyanate, monochlorotriazine, dichlorotriazine, 4,6,-dichloro-1,3,5-triazines, mono- or di-halogen substituted pyridine, mono- or di-halogen substituted diazine, maleimide, haloacetamide, aziridine, sulfonyl halide, acid halide, hydroxysuccinimide ester, hydroxysulfosuccinimide ester, imido ester, hydrazine, azidonitrophenol, azide, 3-(2-pyridyl dithio)-propionamide, glyoxal or aldehyde groups, a nucleophilic reactive group comprising reactive thiol, amine or hydroxyl, a nickel coordinate group, a platinum coordinate group, a terminal alkene or a terminal alkyne, and any combination of the foregoing. As in the case of other embodiments previously described above, a linker arm can be usefully positioned between the compound and the reactive group, or between the solid support and the reactive group.

Antibodies labeled with dyes of the present invention may be used in various formats. For example, an antibody with one of the dyes of the present invention may be used in an immunofluorescent plate assay or in situ analysis of the cellular location and quantity of various antigenic targets. Antibodies labeled with dyes may also be used free in solution in cell counting or cell sorting methods that use a flow cytometer or for in-vitro and in-vivo imaging of animal models.

The presence or absence of a signal may then be used to indicate the presence or absence of the target itself. An example of this is a test where it is sufficient to know whether a particular pathogen is present in a clinical specimen. On the other hand, quantitative assays may also be carried out where it is not so much the intention of evaluating if a target is present but rather the particular amount of target that is present. An example of this is the previously cited microarray assay where the particular rise or fall in the amount of particular mRNA species may be of interest.

In another embodiment of the present invention, dyes that have been disclosed above as well as dyes described previously in the literature may be attached to a carrier with a more general affinity. Dyes may be attached to intercalators that in themselves do not provide signal generation but by virtue of their binding may bring a dye in proximity to a nucleic acid. A further example is attachment of dyes to SDS molecules thereby allowing dyes to be brought into proximity to proteins. Thus this embodiment describes the adaptation of a dye or dyes that lack affinity to a general class of molecules may be adapted by linking them to non-dye molecules or macromolecules that can convey such properties.

Various applications may enjoy the benefits of binding the dyes of the present invention to appropriate targets. As described above, staining of macromolecules in a gel is a methodology that has a long history of use. More recent applications that also may find use are real time detection of amplification (U.S. Pat. No. 5,994,056, U.S. Pat. No. 6,174,670 and U.S. patent application Ser. No. 10/096,076, all of which are hereby incorporated by reference), and binding of nucleic acids to microarrays. In situ assays may also find use where the binding of dyes of the present invention is used to identify the location or quantity of appropriate targets.

Selected embodiments of the compounds of this invention include but are not limited to dyes that are described in FIG. 1 where the level of fluorescence in the presence of aggregates is at least three times higher than the level produced in the presence of monomeric forms. Especially preferred are the compounds listed in Table 1, where a compound previously used for this purpose, Thioflavin T, is included for comparison's sake. These compounds are suitable in a number of different applications where aggregation is being measured or studied. In addition, a number of other useful compounds are described in FIG. 2. Although these do not exhibit the high aggregate/monomer ratios seen for the compounds in FIG. 1, utility is still found in other applications where they may be used as labels. Among notable examples of such compounds are those listed in FIG. 1 or including

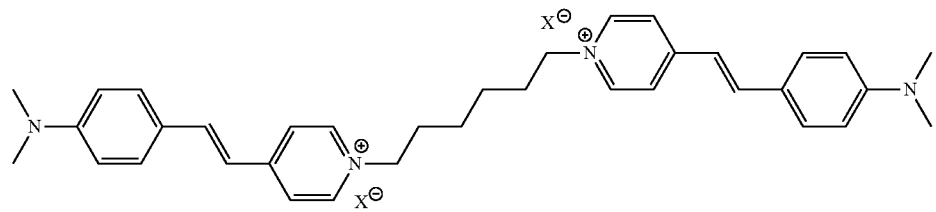

wherein X comprises an anion.

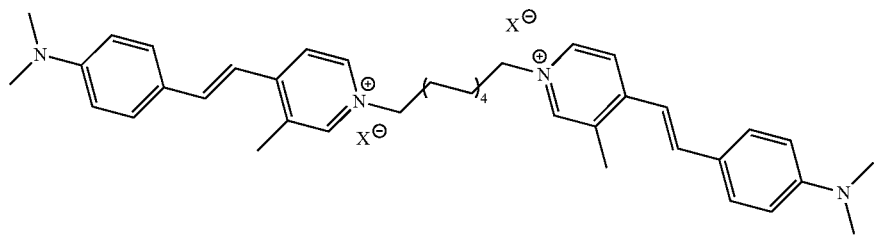

wherein X comprises an anion.

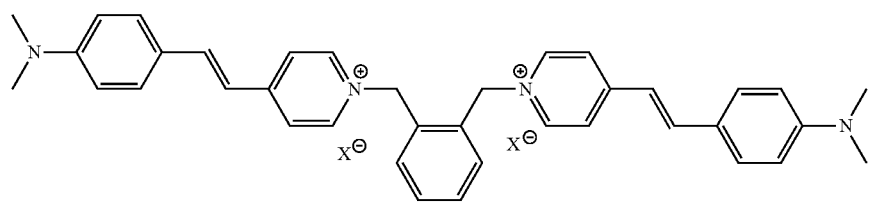
wherein X comprises an anion.
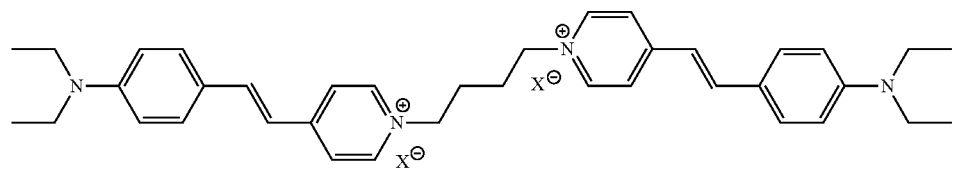
wherein X comprises an anion.
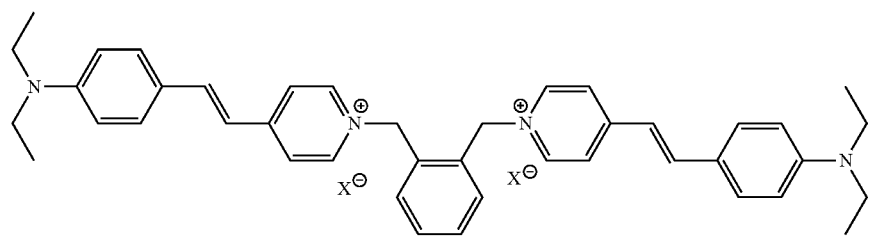
wherein X comprises an anion.
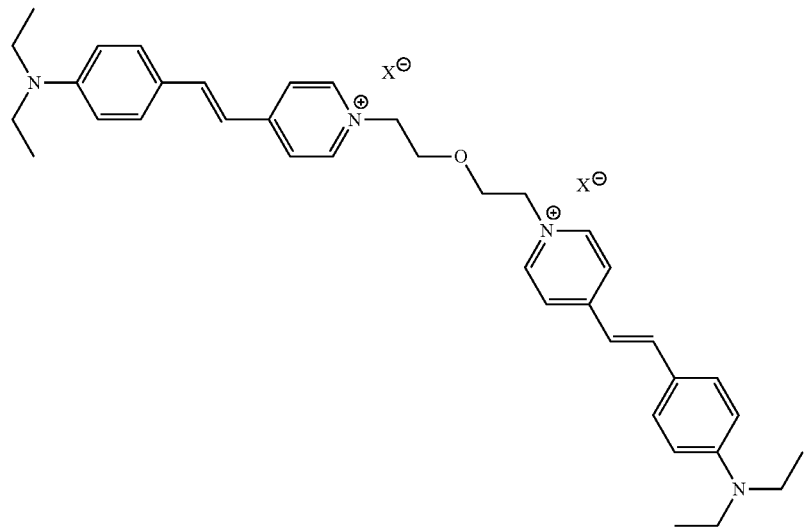
wherein X comprises an anion.

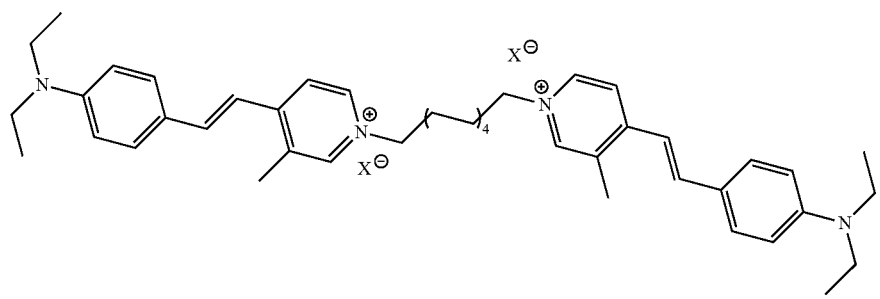

wherein X comprises an anion.

Spectral Properties:

Among the various aspects of the present invention is the provision and use of a series of styryl cyanine dyes that upon binding with an amyloid, peptide or protein aggregate, shows a bathochromic shift in the order of more than 20 nm. Also, the fluorescence intensity derived from the interaction of the protein aggregate and dyes of the invention is up to hundreds of fold higher than that derived from the interaction of dye with native protein, therefore the dyes are highly sensitive.

Especially useful for many purposes are dyes that have fluorescence emissions in the range of 600-650 nM since such dyes can avoid interference of biological proteins for the application in tissue staining, such as GFPs (Green fluorescent proteins). Excitation fluorescence for such dyes are preferred to be in the range of 500-600 nM. It can be seen that the dyes in Table 1 fulfill these requirements where the maxima of the fluorescence excitation spectra of these dyes in the presence of aggregates of alpha-synuclein (ASN) are between 511 and 553 nm, and fluorescence emission have their maxima between 603 and 625 nm. The values of the fluorescence quantum yield (QY) of the dyes of the invention in the presence of saturating concentrations of fibrillar protein are situated in the range between 0.01 and 0.08, which allow using relatively small amounts of dye for interaction with protein aggregates, tissues or cell staining. Stokes shift of the dyes of the invention are in the range of 73 to 95 nm and are much larger than the classic amyloid detection dyes, such as Thioflavin T, which only has a 23 nm Stokes shift (as seen in Table 1). The wider Stokes shift of the dyes of the present invention ensures a much lower overlap between excitation and emission, thus allowing more flexible filter set selection, such as a wide excitation and or emission filter to improve the brightness of the dye or increasing the exposure time to enhance the fluorescence intensity. A further consideration of the present invention, is that detection and/or quantification of aggregates may also be improved by a mixture of dyes where at least one of the dyes is one of the compounds illustrated in FIG. 1 or has the structure shown previously for a dimeric styryl dye. The additional dye or (dyes) may also be from FIG. 1 or have the dimeric styryl structure or they may be drawn from those previously described in the literature. The use of more than one dye may widen the breadth of proteins that will successfully generate signals after aggregation when these dyes become bound. The signal will derive from the net amount of fluorescence enhancement derived from each dye in the mixture.

For assaying aggregation of a protein, this invention provides a kit, comprising in packaged combination: (a) two or more compounds, wherein one compound is from FIG. 1B and the other compound provides a higher intensity of fluorescence when measured in the presence of a protein aggregate as compared to the intensity of fluorescence when measured in the presence of a native monomeric form of the protein; and (b) instructions therefor. This kit may further comprise (c) buffers; or (d) positive controls; or (e) negative controls, or (f) a combination of any of the foregoing. Such positive controls comprise protein aggregates and such negative controls comprise protein monomers. The emission maxima of the compounds can range from about 600 nanometers to about 670 nanometers. In another aspect, the emission maxima of the compounds differ by no more than about 50 nanometers (nm). In yet another aspect, the emission maxima of the compounds differ by no more than about 10 nanometers (nm).

Another kit provided by the present invention also is applicable to assaying aggregation of a protein. In this case, the kit comprises in packaged combination (a) two or more compounds, wherein each of the compounds provides a higher intensity of fluorescence when measured in the presence of a protein aggregate as compared to the intensity of fluorescence when measured in the presence of a native monomeric form of the protein, and wherein the emission maxima of the compounds is within 50 nanometers (nm) of each other when measured in the presence of a protein aggregate; and (b) instructions therefor. This kit may further comprise (c) buffers; or (d) positive controls; or (e) negative controls, or (f) a combination of any of the foregoing. These positive controls comprise protein aggregates and the negative controls comprise protein monomers. The emission maxima of the compounds for this kit range from about 600 nanometers to about 670 nanometers. In other embodiments, the emission maxima of the compounds differ by no more than about 10 nanometers (nm). For this particular kit, at least one of said compounds comprises Dye F, Dye Fm(b), D95, D97, L-30, L-33, Lu-1, Lu-2, S-8, S13. S22, S25, S33, S39, S42, S43, S48, S49, SL2131, SL2592, Tio-1, TOL-2, TOL-3, TOL-5, TOL-6, TOL-7, TOL-11, YA-1, YA-3, YAT2134, YAT2135, YAT2148, YAT2149, YAT2150, YAT2213, YAT2214 or YAT2324.

Fluorescence Methods

The dyes, compounds and compositions of the present invention are fluorescently detectable or localized. Techniques and fluorescence methods are well known in the art. A compilation of such techniques and methods are set forth below in Table A which was obtained from Hawe et al., "Extrinsic Fluorescent Dyes as Tools for Protein Characterization," *Pharmaceutical Research*, Vol. 25, page 1488 (July 2008):

TABLE A

Fluorescence Methods and Their Application with Extrinsic Fluorescent Dyes for Protein Characterization

| Method | Information | Application with Noncovalent Extrinsic Dyes |
|---|---|---|
| Steady-state fluorescence | Spectral information (emission spectrum and fluorescence intensity) | Detection of protein structural changes by dye-protein interactions |
| Time-resolved fluorescence | Fluorescence lifetime | Detection of protein structural changes by dye-protein interactions |
| Anisotrophy (steady-state and time-resolved) | Rotational motions | Study of rotational dynamics Determination of size of dye-protein complexes |
| Fluorescence correlation spectroscopy (FCS) | Translational motions/diffusion | Determination of size of dye-protein complexes |
| Fluorescence microscopy | Visualization of particles | Detection of large dye-protein complexes Determination of size and morphology of large aggregates, fibrils, etc. |

For an expert review on such fluorescence methods, see the entire above cited publication by Hawe et al., pages 1487-1499, the contents of which are incorporated herein by reference.

Observation of Protein Aggregates by Fluorescence Microscopy

Fluorescence microscopy allows an early detection of changes in protein solutions, while minimizing alterations to the observed sample after staining with appropriate dyes. In protein formulation, the ability to detect protein aggregates at early time points with the dyes of the present invention can accelerate stability testing and reduce number of samples in long term stability studies. Fluorescence microscopy provides the possibility of studying subtle changes in the aggregation state of the proteins, which is also of interest in medicine and biology, whenever protein characterization is needed. Also, fluorescence microscopy allows the characterization of high-concentration protein formulations without dilution and with minimal impact on the protein's local environment. Furthermore, high-content screening fluorescence-based imaging methods allow quantification of populations of protein aggregates including number of branches, mean fiber length, mean fiber width, size distribution, polydispersity, kinetics of formation and kinetics of disassembly.

Figure 3:
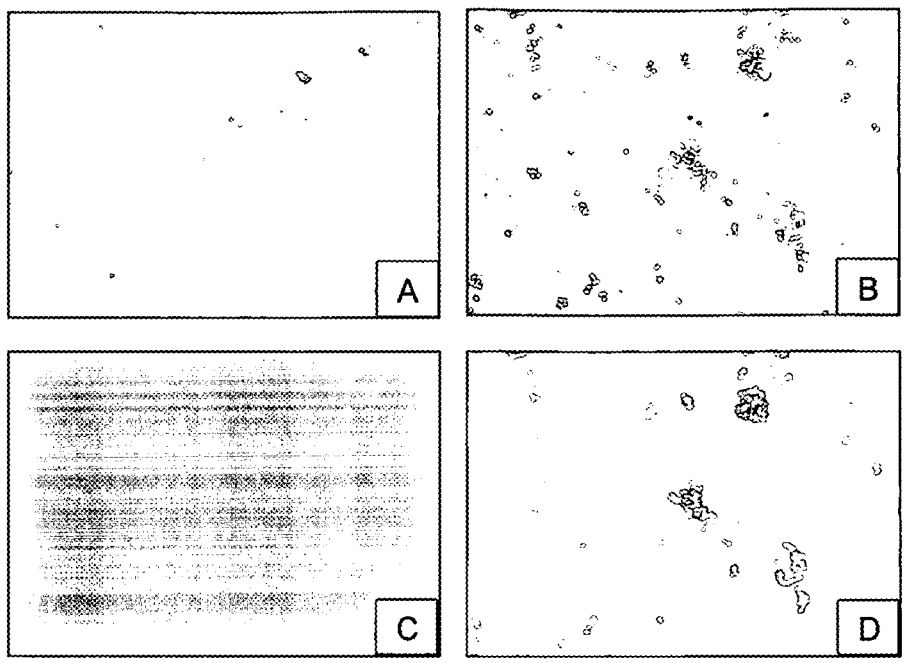
FIG. 3 shows micrographs demonstrating IgG stability in two different buffer formulations.

The present invention includes an example of IgG aggregate detection using dyes of the invention by fluorescence microscopy (FIG. 3). The aggregate formation is barely visible before staining, while clearly becomes visible after staining.

Protein Aggregation Detection and Analysis

The dyes of the invention are also capable of detecting a broader range of protein aggregates than the conventional amyloid detecting dyes, such as Thioflavin T (Thio-T) or Congo Red. These styryl dyes are able to sensitively detect protein aggregates, ranging in size (nanometers to visually observable turbid solution to precipitates) and physico-chemical characteristics (e.g., soluble or insoluble, covalent or non-covalent, reversible or irreversible). Structurally altered proteins have a strong tendency to aggregate, often leading to their precipitation. Irreversible aggregation is a major concern for long-term storage stability of therapeutic proteins and for their shipping and handling.

The styryl dyes of the present invention are also able to detect aggregates at different stages of formation induced by various stresses, such as elevated temperature, agitation and exposure to extremes of pH, ionic strength, or various interfaces (e.g., air-liquid interface) and high protein concentration (as in the case of some monoclonal antibody formulations), chemicals and protein-protein interactions (i.e., PDI-insulin interaction). These fluorescent probes are able to detect broad types and concentration ranges of proteins, in the presence of excipients, at different pH values (2~10) and in the presence of salts and buffers, exhibiting desirable detection limits and dynamic range, excellent sensitivity as well as linear response. This is exemplified by the broad categories of proteins/peptides system in the present invention, including lysozyme, insulin, and IgG molecules, as well as serum proteins, such as β-Lactoglobulin (BLG) and BSA. Therefore, these novel dyes are capable of providing quantitative analysis of protein aggregates in a robust, high throughput fashion.

Thus, the present invention provides a method for detecting the presence of aggregates of a protein in a sample. This detection method comprises the steps of: (i) providing: (a) a sample; (b) one or more dye compounds, wherein at least one of the dye compounds comprises Dye F, Dye Fm(b), D95, D97, L-30, L-33, Lu-1, Lu-2, S-8, S13. S22, S25, S33, S39, S42, S43, S48, S49, SL2131, SL2592, Tio-1, TOL-2, TOL-3, TOL-5, TOL-6, TOL-7, TOL-11, YA-1, YA-3, YAT2134, YAT2135, YAT2148, YAT2149, YAT2150, YAT2213, YAT2214 or YAT2324; and (c) means for detecting fluorescence; (ii) forming a mixture comprising the sample (a) and the one or more dye compounds (b); and (iii) measuring the amount of fluorescence in the mixture, thereby detecting the presence of any protein aggregates in the sample. The sample (a) comprises tissue or cells or proteins derived therefrom, and combinations thereof. In one aspect of this method, the amount of fluorescence measured in step (ii) is compared to the amount of fluorescence when measured in the absence of the sample (a). In another aspect, the amount of fluorescence measured in step (ii) is compared to the amount of fluorescence from a standard curve for protein aggregates and protein monomers in selected proportions. The protein for the standard curve can be the same protein as the protein in the sample, or it can be different.

Another method for detecting the presence of protein aggregates in a sample is also provided by the present invention. Here, the method steps comprise: (i) providing: (a) a sample; (b) one or more compositions having the formula

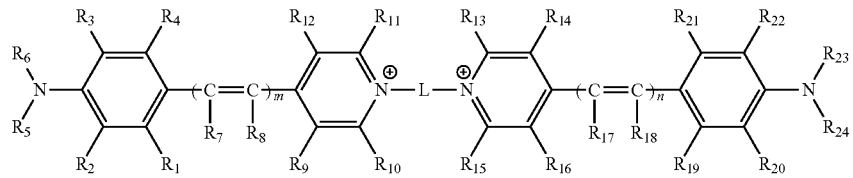

wherein m and n can independently be 1, 2 or 3;

wherein L is a linker arm comprising carbon, sulfur, oxygen, nitrogen, or any combinations thereof;

wherein $R_1$, $R_2$, $R_3$, $R_4$, $R_9$, $R_{10}$, $R_{11}$, $R_{12}$, $R_{13}$, $R_{14}$, $R_{15}$, $R_{16}$, $R_{19}$, $R_{20}$, $R_{21}$ and $R_{22}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken in combination $R_1$ and $R_2$, or $R_3$ and $R_4$, or $R_9$ and $R_{10}$, or $R_{11}$ and $R_{12}$, or $R_{19}$ and $R_{20}$, or $R_{21}$ and $R_{22}$ form a five or six membered ring wherein the ring is saturated or unsaturated, substituted or unsubstituted;

wherein $R_7$, $R_8$, $R_{17}$ and $R_{18}$ can independently be hydrogen, Z, an alkyl group wherein said alkyl group is saturated or unsaturated, linear or branched, substituted or unsubstituted, an alkoxy group wherein the alkoxy group is saturated or unsaturated, branched or linear, substituted or unsubstituted, or when taken together, $R_7$ and $R_8$ and $R_{17}$ and $R_{18}$, may form a 5 or 6 membered ring wherein the ring is saturated or unsaturated, substituted or unsubstituted;

wherein Z comprises a carboxyl group ($CO_2^-$), a carbonate ester ($COER_{25}$), a sulfonate ($SO_3^-$), a sulfonate ester ($SO_2ER_{25}$), a sulfoxide ($SOR_{25}$), a sulfone ($SO_2CR_{25}R_{26}R_{27}$), a sulfonamide ($SO_2NR_{25}R_{26}$), a phosphate ($PO_4^=$), a phosphate monoester ($PO_3^-ER_{25}$), a phosphate diester ($PO_2ER_{25}ER_{26}$), a phosphonate ($PO_3^=$) a phosphonate monoester ($PO_2^-ER_{25}$) a phosphonate diester ($POER_{25}ER_{26}$), a thiophosphate ($PSO_3^=$), a thiophosphate monoester ($PSO_2^-ER_{25}$) a thiophosphate diester ($PSOER_{25}ER_{26}$), a thiophosphonate ($PSO_2$), a thiophosphonate monoester ($PSO^-ER_{25}$) a thiophosphonate diester ($PSER_{25}ER_{26}$), a phosphonamide ($PONR_{25}R_{26}NR_{28}R_{29}$), its thioanalogue ($PSNR_{25}R_{26}NR_{28}R_{29}$), a phosphoramide ($PONR_{25}R_{26}NR_{27}NR_{28}R_{29}$), its thioanalogue ($PSNR_{25}R_{26}NR_{27}NR_{28}R_{29}$), a phosphoramidite ($PO_2R_{25}NR_{28}R_{29}$) or its thioanalogue ($POSR_{25}NR_{28}R_{29}$) where E can be independently O or S;

wherein Z is attached directly, or indirectly through a linker arm comprising carbon, sulfur, oxygen, nitrogen, and any combinations thereof and wherein the linker arm may be saturated or unsaturated, linear or branched, substituted or unsubstituted and any combinations thereof;

wherein $R_9$, $R_{10}$, $R_{11}$, $R_{12}$, $R_{13}$, $R_{14}$, $R_{15}$ and $R_{16}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when $R_9$ and $R_{10}$ or $R_{11}$ and $R_{12}$ or $R_{13}$ and $R_{14}$ or $R_{15}$ and $R_{16}$ comprise alkyl chains that are joined together, a quinoline moiety can be formed;

wherein $R_5$, $R_6$, $R_{23}$ and $R_{24}$ can independently be hydrogen or an alkyl group wherein the alkyl group is saturated or unsaturated, linear or branched, substituted or unsubstituted, or when taken in combination $R_5$ and $R_6$ or $R_2$ and $R_5$ or $R_3$ and $R_6$ or $R_{23}$ and $R_{24}$ or $R_{22}$ and $R_{23}$ or $R_{20}$ and $R_{24}$ form a five or six membered ring wherein the ring is saturated or unsaturated, substituted or unsubstituted; and (c) means for detecting fluorescence; (ii) forming a mixture comprising the sample (a) and the one or more dye compounds (b); and (iii) measuring the amount of fluorescence in the mixture, thereby detecting the presence of any protein aggregates in the sample.

As in earlier embodiments of this invention, the sample (a) comprises tissue or cells or proteins derived therefrom, and combinations thereof. The amount of fluorescence measured in step (ii) can be compared to the amount of fluorescence when measured in the absence of the sample (a). Additionally, the amount of fluorescence measured in step (ii) can be compared to the amount of fluorescence from a standard curve for protein aggregates and protein monomers in selected proportions. The protein for this standard curve can be the same protein as the protein in the sample, or it can comprise a protein that is different from the protein in the sample.

Protein Aggregation Kinetic Studies

Protein aggregation is an important phenomenon that alternatively is part of the normal functioning of nature or has negative consequences via its hypothesized central role in neurodegenerative diseases. A key in controlling protein aggregation is to understand the mechanism(s) of protein aggregation. Kinetic studies, including data curve-fitting, and analysis are, in turn, keys to performing rigorous mechanistic studies. The many approaches in the literature striving to determine the kinetics and mechanism of protein aggregation can be broadly divided into three categories: (i) kinetic and thermodynamic, (ii) empirical, and (iii) other approaches. The large literature of protein aggregation can be distilled down to five classes of postulated mechanisms: i) the subsequent monomer addition mechanism, ii) the reversible association mechanism, iii) prion aggregation mechanisms, iv) an "Ockham's razor"/minimalistic model, and v) quantitative structure activity relationship (QSAR) models [Aimee M. Morris, Murielle A. Watzky, Richard G. Finke, *Biochimica et Biophysica Acta (BBA)—Proteins & Proteomics*, Vol. 1794, No. 3. (March 2009), pp. 375-397]. Corresponding equations derived from aggregation kinetic data can enlighten which proposed mechanism is applicable to the specific protein. Detection of aggregates at their nascent stages, such as intermediates consisting of a couple of monomers, are key in determining critical nucleus size and aggregate growth mechanism. In addition, kinetic studies are also very helpful in screening excipients or inhibitors that can stop or suppress protein aggregation and in assessing enzyme activity in various clinical and research settings. Hence, a sensitive kinetic assay in a robust, high-throughput manner is highly desirable in mechanism determination studies and in drug discovery. Most of the current aggregate analysis technologies, unfortunately, are neither sensitive nor accurate enough to quantify nascent aggregates. Various factors affecting aggregation can be studied by these means; a number of these are described by S Bondos and A Bicknell in (2003) Analytical Biochemistry 316; 223-231 "Detection and prevention of protein aggregation before, during, and after purification" and in addition, Table 1 from this article is reproduced below showing components (including recommended concentrations) that might be used for decreasing aggregation:

TABLE 1

Agents that may promote protein solubility

| | Additive | Recommended concentration range |
|---|---|---|
| Kosmotropes | $MgSO_4$ | 0-0.4M |
| | $(NH_4)_2SO_4$ | 0-0.3M |
| | $Na_2SO_4$ | 0-0.2M |
| | $Cs_2SO_4$ | 0-0.2M |

TABLE 1-continued

Agents that may promote protein solubility

| | Additive | Recommended concentration range |
|---|---|---|
| Weak kosmotropes | NaCl | 0-1M |
| | KCl | 0-1M |
| Chaotropes | CaCl$_2$ | 0-0.2M |
| | MgCl$_2$ | 0-0.2M |
| | LiCl | 0-0.8M |
| | RbCl | 0-0.8M |
| | NaSCN | 0-0.2M |
| | NaI | 0-0.4M |
| | NaClO$_4$ | 0-0.4M |
| | NaBr | 0-0.4M |
| | Urea | 0-1.5M |
| Amino acids | Glycine | 0.5-2% |
| | L-arginine | 0-5M |
| Sugars and polyhydric alcohols | Sucrose | 0-1M |
| | Glucose | 0-2M |
| | Lactose | 0.1-0.5M |
| | Ethylene glycol | 0-60% v/v |
| | Xylitol | 0-30% w/v |
| | Mannitol | 0-15% w/v |
| | Inositol | 0-10% w/v |
| | Sorbitol | 0-40% w/v |
| | Glycerol | 5-50% v/v |
| Detergents | Tween 80 | 0-0.2% w/v |
| | Tween 20 | 0-120 μM |
| | Nonidet P-40 | 0-1% |

Embodiments of the present invention encompass two methods of applying these styryl dyes into kinetics study of protein aggregation, such as Lysozyme and IgG aggregation, induced by various types of stress, including pH, shaking and temperature shift and in the presence or absence of excipient (s). The first method comprises the following steps: (1) apply a stress to a protein formulation for a certain period of time; (2) release stress by switching off the stress, such as heat or harsh pH to freeze or trap the aggregate formation; (3) fluorescence reading of these formulations by addition of selected dyes of the invention; (4) plot the relative fluorescence unit (RFU) vs. time curve and further process the kinetic curve to extract more desired information. This method is beneficial for some proteins whose aggregation can be significantly interfered with by probing dye binding (especially for nascent or intermediate aggregates, characterized by a much smaller surface area than those more matured aggregates) at stressed condition, which is minimized after the release of the stress.

The second method is more convenient compared to the first method. First, mix the dye with the protein formulation prior to the application of the stress; second, apply the stress and start recording the fluorescence response at various points of time; finally, plot a relative fluorescence unit (RFU) vs. time curve and possibly perform further processing of the curve to extract more desired information. This method, though labor saving, much more robust and accurate in time, may not be applicable for some proteins if the dye blocks, promotes or interferes with the addition of monomers to the aggregate intermediates or polymerization of aggregate intermediates. However, notwithstanding the mentioned caveats, the second method is generally preferred, since it allows for a simpler high throughput assay.

Thus, the present invention provides a method for detecting the formation of aggregates of a protein in a sample. In this method, steps are carried out comprising: (i) providing: (a) a sample; (b) one or more of dye compounds, wherein at least one of the dye compounds comprises Dye F, Dye Fm(b), D95, D97, L-30, L-33, Lu-1, Lu-2, S-8, S13. S22, S25, S33, S39, S42, S43, S48, S49, SL2131, SL2592, Tio-1, TOL-2, TOL-3, TOL-5, TOL-6, TOL-7, TOL-11, YA-1, YA-3, YAT2134, YAT2135, YAT2148, YAT2149, YAT2150, YAT2213, YAT2214 or YAT2324; and (c) means for detecting fluorescence; (ii) forming a mixture with the sample (a) and the one or more dye compounds (b); (iii) measuring at preselected time intervals the amount of fluorescence in the mixture formed in step (ii), thereby detecting the formation of protein aggregates.

In aspects of the just described method, the sample (a) comprises tissue or cells or proteins derived therefrom, and combinations thereof. Moreover, the amount of fluorescence measured in step (ii) can be compared to the amount of fluorescence when measured in the absence of the sample (a). Alternatively, the amount of fluorescence measured in step (ii) can be compared to the amount of fluorescence from a standard curve for protein aggregates and protein monomers in selected proportions. In this latter case, the protein for the standard curve can be the same protein as the protein in the sample, or it can be different from the protein in the sample. In another aspect of this method, the prescribed intervals in step (iii) and the prescribed intervals in step (v) comprise minute intervals over the course of an hour.

Another method is also provided by the invention herein for detecting the formation of aggregates of a protein in a sample. This method comprises carrying out the steps of (i) providing: (a) a sample; (b) one or more compositions having the formula

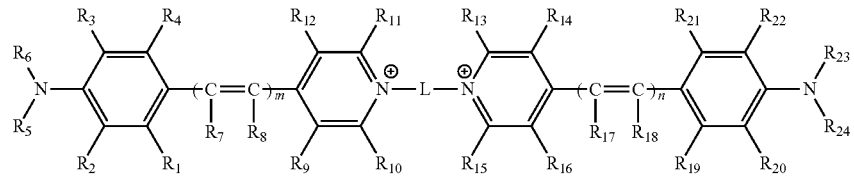

wherein m and n can independently be 1, 2 or 3;

wherein L is a linker arm comprising carbon, sulfur, oxygen, nitrogen, or any combinations thereof;

wherein $R_1$, $R_2$, $R_3$, $R_4$, $R_9$, $R_{10}$, $R_{11}$, $R_{12}$, $R_{13}$, $R_{14}$, $R_{15}$, $R_{16}$, $R_{19}$, $R_{20}$, $R_{21}$ and $R_{22}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken in combination $R_1$ and $R_2$, or $R_3$ and $R_4$, or $R_9$ and $R_{10}$, or $R_{11}$ and $R_{12}$, or $R_{19}$ and $R_{20}$, or $R_{21}$ and $R_{22}$ form a five or six membered ring wherein the ring is saturated or unsaturated, substituted or unsubstituted;

wherein $R_7$, $R_8$, $R_{17}$ and $R_{18}$ can independently be hydrogen, Z, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken together, $R_7$ and $R_8$ and $R_{17}$ and $R_{18}$, may form a 5 or 6 membered ring wherein the ring is saturated or unsaturated, substituted or unsubstituted;

wherein Z comprises a carboxyl group ($CO_2^-$), a carbonate ester ($COER_{25}$), a sulfonate ($SO_3^=$), a sulfonate ester ($SO_2ER_{25}$), a sulfoxide ($SOR_{25}$), a sulfone ($SO_2CR_{25}R_{26}R_{27}$), a sulfonamide ($SO_2NR_{25}R_{26}$), a phosphate ($PO_4^=$), a phosphate monoester ($PO_3^-ER_{25}$), a phosphate diester ($PO_2ER_{25}ER_{26}$), a phosphonate ($PO_3^=$) a phosphonate monoester ($PO_2^-ER_{25}$) a phosphonate diester ($POER_{25}ER_{26}$), a thiophosphate ($PSO_3^=$), a thiophosphate monoester ($PSO_2^-ER_{25}$) a thiophosphate diester ($PSOER_{25}ER_{26}$), a thiophosphonate ($PSO_2^=$), a thiophosphonate monoester ($PSO^-ER_{25}$) a thiophosphonate diester ($PSER_{25}ER_{26}$), a phosphonamide ($PONR_{25}R_{26}NR_{28}R_{29}$), its thioanalogue ($PSNR_{25}R_{26}NR_{28}R_{29}$), a phosphoramide ($PONR_{25}R_{26}NR_{27}NR_{28}R_{29}$), its thioanalogue ($PSNR_{25}R_{26}NR_{27}NR_{28}R_{29}$), a phosphoramidite ($PO_2R_{25}NR_{28}R_{29}$) or its thioanalogue ($POSR_{25}NR_{28}R_{29}$) where E can be independently O or S;

wherein Z is attached directly, or indirectly through a linker arm comprising carbon, sulfur, oxygen, nitrogen, and any combinations thereof and wherein the linker arm may be saturated or unsaturated, linear or branched, substituted or unsubstituted and any combinations thereof;

wherein $R_9$, $R_{10}$, $R_{11}$, $R_{12}$, $R_{13}$, $R_{14}$, $R_{15}$ and $R_{16}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when $R_9$ and $R_{10}$ or $R_{11}$ and $R_{12}$ or $R_{13}$ and $R_{14}$ or $R_{15}$ and $R_{16}$ comprise alkyl chains that are joined together, a quinoline moiety can be formed;

wherein $R_5$, $R_6$, $R_{23}$ and $R_{24}$ can independently be hydrogen or an alkyl group wherein the alkyl group is saturated or unsaturated, linear or branched, substituted or unsubstituted, or when taken in combination $R_5$ and $R_6$ or $R_2$ and $R_5$ or $R_3$ and $R_6$ or $R_{23}$ and $R_{24}$ or $R_{22}$ and $R_{23}$ or $R_{20}$ and $R_{24}$ form a five or six membered ring wherein the ring is saturated or unsaturated, substituted or unsubstituted; and (c) means for detecting fluorescence; (ii) forming a mixture with the sample (a) and the one or more dye compounds (b); and (iii) measuring at preselected time intervals the amount of fluorescence in the mixture formed in step (ii), thereby detecting the formation of protein aggregates.

In this just described method, the sample (a) comprises tissue or cells or proteins derived therefrom, and combinations thereof. Furthermore, the amount of fluorescence measured in step (ii) can be compared to the amount of fluorescence when measured in the absence of the sample (a). The amount of fluorescence measured in step (ii) can also be compared to the amount of fluorescence from a standard curve for protein aggregates and protein monomers in selected proportions. The protein for the standard curve can be the same protein as the protein in the sample. The protein for the standard curve can also comprise a protein that is different from the protein in the sample. In this method, the prescribed intervals in step (iii) and the prescribed intervals in step (v) can comprise minute intervals over the course of an hour. It is noteworthy that the aggregates of the protein can comprise a number of different forms, including but not limited to aggresomes, aggresome-like structures, inclusion bodies, Lewy bodies, Mallory bodies or neurofibriliary tangles, and a combination of the foregoing.

Another useful method of the present invention is a method for determining whether a test compound decreases aggregation of a protein. Here, the method comprises the steps of: (i) providing: (a) the protein; (b) one or more of compounds comprising Dye F, Dye Fm(b), D95, D97, L-30, L-33, Lu-1, Lu-2, S-8, S13. S22, S25, S33, S39, S42, S43, S48, S49, SL2131, SL2592, Tio-1, TOL-2, TOL-3, TOL-5, TOL-6, TOL-7, TOL-11, YA-1, YA-3, YAT2134, YAT2135, YAT2148, YAT2149, YAT2150, YAT2213, YAT2214 or YAT2324; and (c) the test compound; (ii) forming a first mixture comprising the protein (a) and one or more compounds (b); (iii) measuring the amount of fluorescence in the first mixture at prescribed intervals; (iv) forming a second mixture comprising the protein (a), one or more compounds (b) and the test compound (c); (v) measuring the amount of fluorescence in the second mixture at prescribed intervals; and (vi) comparing the amount of fluorescence measured in step (iii) and step (v); thereby determining whether the test compound (c) decreases the aggregation of the protein (a).

In the just described method, the prescribed intervals in step (iii) and the prescribed intervals in step (v) can be the same intervals of time. The prescribed intervals can be measured in a range of time units, including but not limited to minutes, hours or days. In other aspects of this method, the prescribed intervals in step (iii) and the prescribed intervals in step (v) comprise minute intervals over the course of an hour. In other aspects, the prescribed intervals in step (iii) and the prescribed intervals in step (v) comprise daily intervals over the course of at least one month. In another embodiment, in step (iii), fluorescence can be initially measured 30 minutes after forming the first mixture, and in step (v), fluorescence can be initially measured 30 minutes after forming the second mixture. Moreover, in step (iii), fluorescence can be measured in one or more 30 minute intervals after the initial measurement, and in step (v), fluorescence can be measured in one or more 30 minute intervals after the initial measurement. In carrying out this method, it may be useful or desirable after the forming steps (ii) and (iv), that the first mixture and the second mixture are maintained at room temperature prior to measuring fluorescence in steps (iii) and (v). Furthermore, after the forming steps (ii) and (iv), the first mixture and the second mixture can be incubated at a temperature ranging from about 4° C. to about 95° C. In other aspects, the first mixture and the second mixture are incubated at a temperature of about 30° C. after the first mixture and the second mixture have been formed. The first mixture and the second mixture can also be incubated at a temperature of about 37° C. after the first mixture and the second mixture have been formed.

The test compound (c) itself can vary, comprising a kosmotrope, a chaotrope, an amino acid, a peptide, a reducing agent, a carbohydrate, a detergent, a surfactant, a zwitterion or a polyhydric alcohol, and combinations thereof. Any of these test compound forms (c) can have a range of concentrations from about 0 molar to about 2 molar, a range of pH values from about 4 to about 10, and any combinations thereof. The test compound (c) can also comprise a storage buffer for said protein. Such storage buffer can comprise a set of buffer formulations with a range of concentrations from about 0 molar to about 2 molar, a range of pH values from about 4 to about 10, and any combinations thereof.

In other aspects of this method, particularly in steps (iii) and (v), fluorescence can be measured at one or more different temperatures after forming the first mixture and the second mixture. Such different temperatures can be selected from temperatures ranging from about 4° C. to about 100° C. Further, fluorescence measurements can be carried out as a series of discrete temperatures, wherein measuring steps (iii) and (v) are carried out after incubation at each of the different discrete temperatures. Alternatively, measuring steps (iii) and (v) can be carried out while changing temperatures.

Also provided by this invention is a method for determining whether a test compound decreases aggregation of a protein. This method comprises the steps of: (i) providing: (a) the protein; (b) one or more compositions having the formula

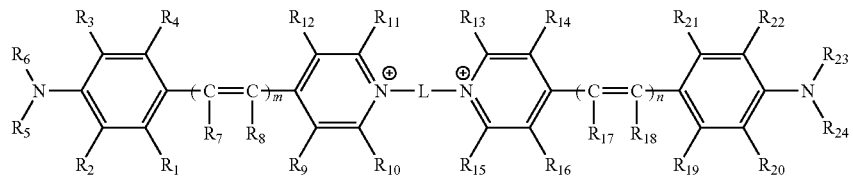

wherein m and n can independently be 1, 2 or 3;

wherein L is a linker arm comprising carbon, sulfur, oxygen, nitrogen, or any combinations thereof;

wherein $R_1$, $R_2$, $R_3$, $R_4$, $R_9$, $R_{10}$, $R_{11}$, $R_{12}$, $R_{13}$, $R_{14}$, $R_{15}$, $R_{16}$, $R_{19}$, $R_{20}$, $R_{21}$ and $R_{22}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken in combination $R_1$ and $R_2$, or $R_3$ and $R_4$, or $R_9$ and $R_{10}$, or $R_{11}$ and $R_{12}$, or $R_{19}$ and $R_{20}$, or $R_{21}$ and $R_{22}$ form a five or six membered ring wherein the ring is saturated or unsaturated, substituted or unsubstituted;

wherein $R_7$, $R_8$, $R_{17}$ and $R_{18}$ can independently be hydrogen, Z, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken together, $R_7$ and $R_8$ and $R_{17}$ and $R_{18}$, may form a 5 or 6 membered ring wherein the ring is saturated or unsaturated, substituted or unsubstituted;

wherein Z comprises a carboxyl group ($CO_2^-$), a carbonate ester ($COER_{25}$), a sulfonate ($SO_3^-$), a sulfonate ester ($SO_2ER_{25}$), a sulfoxide ($SOR_{25}$), a sulfone ($SO_2CR_{25}R_{26}R_{27}$), a sulfonamide ($SO_2NR_{25}R_{26}$), a phosphate ($PO_4^=$), a phosphate monoester ($PO_3^-ER_{25}$), a phosphate diester ($PO_2ER_{25}ER_{26}$), a phosphonate ($PO_3^=$) a phosphonate monoester ($PO_2^-ER_{25}$) a phosphonate diester ($POER_{25}ER_{26}$), a thiophosphate ($PSO_3^=$), a thiophosphate monoester ($PSO_2^-ER_{25}$) a thiophosphate diester ($PSOER_{25}ER_{26}$), a thiophosphonate ($PSO_2^=$), a thiophosphonate monoester ($PSO^-ER_{25}$) a thiophosphonate diester ($PSER_{25}ER_{26}$), a phosphonamide ($PONR_{25}R_{26}NR_{28}R_{29}$), its thioanalogue ($PSNR_{25}R_{26}NR_{28}R_{29}$), a phosphoramide ($PONR_{25}R_{26}NR_{27}NR_{28}R_{29}$), its thioanalogue ($PSNR_{25}R_{26}NR_{27}NR_{28}R_{29}$), a phosphoramidite ($PO_2R_{25}NR_{28}R_{29}$) or its thioanalogue ($POSR_{25}NR_{28}R_{29}$) where E can be independently O or S;

wherein Z is attached directly, or indirectly through a linker arm comprising carbon, sulfur, oxygen, nitrogen, and any combinations thereof and wherein the linker arm may be saturated or unsaturated, linear or branched, substituted or unsubstituted and any combinations thereof;

wherein $R_9$, $R_{10}$, $R_{11}$, $R_{12}$, $R_{13}$, $R_{14}$, $R_{15}$ and $R_{16}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when $R_9$ and $R_{10}$ or $R_{11}$ and $R_{12}$ or $R_{13}$ and $R_{14}$ or $R_{15}$ and $R_{16}$ comprise alkyl chains that are joined together, a quinoline moiety can be formed;

wherein $R_5$, $R_6$, $R_{23}$ and $R_{24}$ can independently be hydrogen or an alkyl group wherein the alkyl group is saturated or unsaturated, linear or branched, substituted or unsubstituted, or when taken in combination $R_5$ and $R_6$ or $R_2$ and $R_5$ or $R_3$ and $R_6$ or $R_{23}$ and $R_{24}$ or $R_{22}$ and $R_{23}$ or $R_{20}$ and $R_{24}$ form a five or six membered ring wherein the ring is saturated or unsaturated, substituted or unsubstituted; (c) a test compound; and (d) means for detecting fluorescence; (ii) forming a first mixture with the protein (a) and the one or more compounds (b); (iii) measuring the amount of fluorescence in the first mixture at prescribed intervals; (iv) forming a second mixture with the protein (a), one or more compounds (b) and the test compound to be assayed (c); (v) measuring the amount of fluorescence in the second mixture at prescribed intervals; and (vi) comparing the amount of fluorescence measured in step (iii) and step (v), thereby determining whether the test compound (c) decreases the aggregation of said protein (a). In certain aspects of this method, the prescribed intervals in step (iii) and the prescribed intervals in step (v) are the same intervals of time. The prescribed intervals can be measured in minutes, hours or days, or other units of time. The prescribed intervals in step (iii) and the prescribed intervals in step (v) can comprise minute intervals over the course of an hour. In another embodiment, the prescribed intervals in step (iii) and the prescribed intervals in step (v) can comprise daily intervals over the course of at least one month.

In a variation of the above described method, in step (iii), fluorescence can be initially measured 30 minutes after forming the first mixture, and in step (v), fluorescence can be initially measured 30 minutes after forming the second mixture. In another variation, in step (iii), fluorescence can be measured in one or more 30 minute intervals after the initial measurement, and in step (v), fluorescence can be measured in one or more 30 minute intervals after the initial measurement. After the forming steps (ii) and (iv), the first mixture and the second mixture can be maintained at room temperature prior to measuring fluorescence in steps (iii) and (v). Furthermore, after the forming steps (ii) and (iv), the first mixture and the second mixture can be incubated at a temperature ranging from about 4° C. to about 95° C. Moreover, the first mixture and the second mixture can be incubated at a temperature of about 30° C. after forming the first mixture and said second mixture. In another aspect, the first mixture and the second mixture can be incubated at a temperature of about 37° C. after the first mixture and the second mixture have been formed.

As in the case of earlier described embodiments of this invention, the test compound (c) can comprise a kosmotrope, a chaotrope, an amino acid, a peptide, a reducing agent, a carbohydrate, a detergent, a surfactant, a zwitterion or a polyhydric alcohol, and combinations thereof. Any of these test compounds (c) can have a range of concentrations from about 0 molar to about 2 molar, a range of pH values from about 4 to about 10, and any combinations thereof. In certain preferred aspects of this invention, the test compound (c) can comprises a storage buffer for the protein. Such a storage buffer can comprises a set of buffer formulations with a range of concentrations from about 0 molar to about 2 molar, a range of pH values from about 4 to about 10, and any combinations thereof. In steps (iii) and (v) of this method, fluorescence can be measured at one or more different temperatures after forming the first mixture and the second mixture. These different temperatures can be selected from temperatures ranging from about 4° C. to about 100° C. Fluorescence measurements in this method can be carried out as a series of discrete temperatures, wherein measuring steps (iii) and (v) are carried out after incubation at each of the different discrete temperatures. Alternatively, measuring steps (iii) and (v) in this method can be carried out while changing temperatures.

Still yet another method for determining whether a test compound affects aggregation of a protein is provided by this invention. This method comprises the steps of: (i) providing: (a) the protein; (b) two or more dyes wherein each of the dyes has a fluorescence intensity that is at least three times higher when measured in the presence of an aggregate of a protein as compared to the fluorescence intensity when measured in the presence of a native monomer of the protein; (c) a test compound; and (d) means for detection of fluorescence; (ii) forming a first mixture with the protein (a) and the two or more dyes (b); (iii) measuring the amount of fluorescence in the first mixture at prescribed intervals; (iv) forming a second mixture with the protein (a), two or more dyes (b) and the compound to be assayed (c); (v) measuring the amount of fluorescence in the second mixture at prescribed intervals; and (vi) comparing the amount of fluorescence measured in step (iii) and step (v), thereby determining whether the test compound (c) affects aggregation of the protein.

In this method, the dyes in the presence of a protein aggregate can have emission maxima within 150 nm of each other, preferably, emission maxima within 50 nm. Further, at least one of the two or more dyes comprises a compound having a structure from FIG. 1B.

In yet another method for determining whether a test compound affects aggregation of a protein, the following steps are carried out: (i) providing: (a) said protein; (b) two or more dyes, wherein each of the two or more dyes in the presence of an aggregate of the protein has a higher florescent intensity as compared to the fluorescent intensity when measured in the presence of the native monomeric form of the protein, and wherein at least one of the dyes has the formula wherein m and n can independently be 1, 2 or 3;

wherein L is a linker arm comprising carbon, sulfur, oxygen, nitrogen, or any combinations thereof;

wherein $R_1$, $R_2$, $R_3$, $R_4$, $R_9$, $R_{10}$, $R_{11}$, $R_{12}$, $R_{13}$, $R_{14}$, $R_{15}$, $R_{16}$, $R_{19}$, $R_{20}$, $R_{21}$ and $R_{22}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken in combination $R_1$ and $R_2$, or $R_3$ and $R_4$, or $R_9$ and $R_{10}$, or $R_{11}$ and $R_{12}$, or $R_{19}$ and $R_{20}$, or $R_{21}$ and $R_{22}$ form a five or six membered ring wherein the ring is saturated or unsaturated, substituted or unsubstituted;

wherein $R_7$, $R_8$, $R_{17}$ and $R_{18}$ can independently be hydrogen, Z, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken together, $R_7$ and $R_8$ and $R_{17}$ and $R_{18}$, may form a 5 or 6 membered ring wherein the ring is saturated or unsaturated, substituted or unsubstituted;

wherein Z comprises a carboxyl group ($CO_2^-$), a carbonate ester ($COER_{25}$), a sulfonate ($SO_3^-$), a sulfonate ester ($SO_2ER_{25}$), a sulfoxide ($SOR_{25}$), a sulfone ($SO_2CR_{25}R_{26}R_{27}$), a sulfonamide ($SO_2NR_{25}R_{26}$), a phosphate ($PO_4^=$), a phosphate monoester ($PO_3^-ER_{25}$), a phosphate diester ($PO_2ER_{25}ER_{26}$), a phosphonate ($PO_3^=$) a phosphonate monoester ($PO_2^-ER_{25}$) a phosphonate diester ($POER_{25}ER_{26}$), a thiophosphate ($PSO_3^=$), a thiophosphate monoester ($PSO_2^-ER_{25}$) a thiophosphate diester ($PSOER_{25}ER_{26}$), a thiophosphonate ($PSO_2^=$), a thiophosphonate monoester ($PSO^-ER_{25}$) a thiophosphonate diester ($PSER_{25}ER_{26}$), a phosphonamide ($PONR_{25}R_{26}NR_{28}R_{29}$), its thioanalogue ($PSNR_{25}R_{26}NR_{28}R_{29}$), a phosphoramide ($PONR_{25}R_{26}NR_{27}NR_{28}R_{29}$), its thioanalogue ($PSNR_{25}R_{26}NR_{27}NR_{28}R_{29}$), a phosphoramidite ($PO_2R_{25}NR_{28}R_{29}$) or its thioanalogue ($POSR_{25}NR_{28}R_{29}$) where E can be independently O or S;

wherein Z is attached directly, or indirectly through a linker arm comprising carbon, sulfur, oxygen, nitrogen, and any combinations thereof and wherein the linker arm may be saturated or unsaturated, linear or branched, substituted or unsubstituted and any combinations thereof;

wherein $R_9$, $R_{10}$, $R_{11}$, $R_{12}$, $R_{13}$, $R_{14}$, $R_{15}$ and $R_{16}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when $R_9$ and $R_{10}$ or $R_{11}$ and $R_{12}$ or $R_{13}$ and $R_{14}$ or $R_{15}$ and $R_{16}$ comprise alkyl chains that are joined together, a quinoline moiety can be formed;

wherein $R_5$, $R_6$, $R_{23}$ and $R_{24}$ can independently be hydrogen or an alkyl group wherein the alkyl group is saturated or

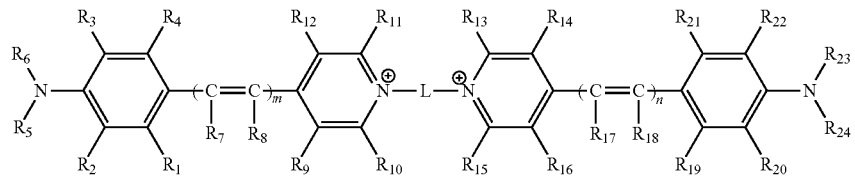

unsaturated, linear or branched, substituted or unsubstituted, or when taken in combination $R_5$ and $R_6$ or $R_2$ and $R_5$ or $R_3$ and $R_6$ or $R_{23}$ and $R_{24}$ or $R_{22}$ and $R_{23}$ or $R_{20}$ and $R_{24}$ form a five or six membered ring wherein the ring is saturated or unsaturated, substituted or unsubstituted; (c) a compound to be assayed; and (d) means for detecting fluorescence; (ii) forming a first mixture with the protein (a) and the two or more dyes (b); (iii) measuring the amount of fluorescence in the first mixture at prescribed intervals; (iv) forming a second mixture with the protein (a), the two or more dyes (b) and the compound to be assayed (c); (v) measuring the amount of fluorescence in the second mixture at prescribed intervals; and (vi) comparing the amount of fluorescence measured in step (iii) and step (v), thereby determining whether the test compound (c) affects aggregation of the protein.

In certain embodiments, at least one dye having the above formula, further has a structure from FIG. 1B.

This invention also provides a method for determining whether a test compound affects aggregation of a protein. In this method, steps are carried out comprising: (i) providing: (a) the protein; (b) two or more dyes, wherein at least one of the dyes comprises Dye F, Dye Fm(b), D95, D97, L-30, L-33, Lu-1, Lu-2, S-8, S13. S22, S25, S33, S39, S42, S43, S48, S49, SL2131, SL2592, Tio-1, TOL-2, TOL-3, TOL-5, TOL-6, TOL-7, TOL-11, YA-1, YA-3, YAT2134, YAT2135, YAT2148, YAT2149, YAT2150, YAT2213, YAT2214 or YAT2324, and wherein each of the two or more dyes in the presence of an aggregate of the protein has a higher florescent intensity as compared to the fluorescent intensity when measured in the presence of the native monomeric form of the protein; (c) a compound to be assayed; and (d) means for detecting fluorescence; (ii) forming a first mixture with the protein (a) and the two or more dyes (b); (iii) measuring the amount of fluorescence in the first mixture at prescribed intervals; (iv) forming a second mixture with the protein (a), the two or more dyes (b) and the compound to be assayed (c); (v) measuring the amount of fluorescence in the second mixture at prescribed intervals; and (vi) comparing the amount of fluorescence measured in step (iii) and step (v), thereby determining whether the test compound (c) affects aggregation of the protein. Preferably, the dyes in the presence of a protein aggregate have emission maxima within 150 nm of each other. More preferably, the emission maxima is within 50 nm.

Methods of Evaluating Protein Formulation Stability Using Accelerated Stability Testing Embodiments of the present invention are directed to reliable, time and cost-efficient methods for evaluating the relative chemical and physical stability of a particular protein formulation. Thus, embodiments of the invention are useful analytical tools for developing new protein formulations with increased stability, as well as for use in evaluating the stability of newly prepared batches of known protein formulations in quality control procedures, or the like.

Embodiments of the present invention encompass a fully automated assay of protein stability that generally requires less than one week for evaluating protein formulations. The present invention method comprises preparing two series of formulations, one formed before stress test (pre-stress formulations), another formed after stress test (post-stress formulations), followed by an adding aggregate detection reagent that include one or more dyes of the present invention. The dye or dyes of the present invention may be used alone for this purpose oror they may be used in conjunction with other commercial dyes, such as Nile Red, Thioflavin-T, ANS or Congo Red. This is followed by comparing the fluorescence response of different formulations to rank the amount of aggregates existing within individual formulations.

In one exemplification of this method, the following 6 steps may be carried out:

Step (1). A selected group of components, including, but not limited to excipients, salts, buffers, co-solvents, metal ions, preservatives, surfactants, and ligands are collected and their stock solutions are prepared.

Step (2). Preliminary formulations comprising one or more components following a standard design of experiment procedure aimed at generating relevant information are designed and the protein formulations, preferably containing the same concentration of protein are prepared.

Step (3). A stress such as heat, agitation, rotation, harsh pH, ultrasound, shearing or the like, is simultaneously applied externally to multiple protein formulations under evaluation, which are held in individual containers, preferably in separate wells of one microplate (s), which is preferably sealed, each with zero, one or more components of interests; meanwhile, the formulation with zero component of interests, but the same protein concentration as the formulations with component (s) of interests can be prepared in a separately sealed container in bulk quantity.

Step (4). After stress is released, the bulk protein formulation that has zero components of interests is split and mixed with one or more components of interests to make up similar formulations as those subjected to the stress test, preferably in wells of another microplate. Note that the later added components of interest solutions dilute the resulted non-stressed formulations, making them less concentrated as their stressed counterpart; this can be adjusted later in the step where the probing dyes are added. These control formulations which have not experienced the stress test allow accurate evaluation of the functions of the components of interests during the stress test since components of interests themselves can affect the fluorescence response of protein aggregates to some extent.

Step (5). A solution of the dye or dyes of the present invention (and the buffer in which the dyes are dissolved) are added into the protein formulations such that post-stress formulations are more concentrated than that added to the stressed formulations to result in the same concentration of protein, components of interests and dye(s) for both pre-stress formulation and post-stress counterpart. After an incubation period, the microplates are read in a conventional plate reader by, for example, fluorescence intensity or fluorescence polarization measurement.

Step (6). The formulations can be first evaluated within the group (i.e. either pre-stress or post-stress formulations), which are preferably tested in one microplate, by comparing formulations containing one or more components of interests with that containing no components of interests. This method can eliminate the errors produced during the preparation of different plates (the sample formulation plate(s) and the control formulation plate(s), which can take 10~60 minutes. Then fluorescence ratio of each stress tested formulation to its corresponding control without stress application can be further calculated. The function of components of interests during stress is evaluated by using the fluorescence ratio of components of interests added before application of stress vs. after application of stress using zero components of interests as a reference. Therefore, the present invention is further directed to a method to evaluate components of interests that can stabilize or destabilize protein in order to optimize protein formulations.

The distinguished properties of the dyes of the invention allow their wide application in the protein/peptide formulation field, especially on a high-throughput technology platform. Compared with other fluorescent probes, such as intrinsic tyrosine or externally added probes, such as 1-anilino-naphthalene-8-sulfonate (ANS), Nile Red or Thioflavin-T, the dyes of the present invention are better capable of providing quantitative analysis of protein aggregates in a robust, high throughput fashion and are applicable to more categories of proteins under various conditions. In some instances two or more dyes of the present invention are applied to a sample. This facilitates detection of the broadest range of protein aggregates since these means provide that if one dye does not bind a particular aggregate, another can compensate for this deficiency.

Protein Stability Shift Assay Based on Fluorescent Detection of Protein Aggregation Using Exogenously Added Fluorophores Protein stability can be altered by various components discussed in protein formulation embodiments, including, but not limited to excipients, salts, buffers, co-solvents, metal ions, preservatives, surfactants, and ligands. Protein stability can be shifted by various stresses, including elevated temperature, which is often referred to as a thermal shift or by addition of chemical denaturants, such as urea, guanidinium isocyanate or the like. A protein stability shift assay has a wide spectrum of applications in, but not limited to investigation of protein refolding conditions, optimization of recombinant protein expression/purification conditions, protein crystallization conditions, selection of ligand/drug/vaccine/diagnostic reagents and protein formulations.

The classic thermal shift technologies based on protein aggregate detection utilize a melting point device to raise the temperature stepwise, coupled with aggregation detection technologies, such as light scattering technology (an example includes but is not limited to differential static light scattering (DSLS)) to monitor protein aggregation. This type of technology usually requires a high protein concentration, therefore, it is not cost effective. In addition, it cannot work effectively on formulations with low protein concentrations or finalize protein formulations which require a very low detection limit for aggregates (typically ~1-5%), which is usually beyond the detection limit of these classic technologies.

Thermofluor® (J&J, 3-Dimensional Pharmaceuticals, Inc, Exton, Pa., U.S. Pat. No. 6,020,141) is a biophysical technique used to study (relative) protein stabilities. The solution of protein is heated up stepwise from room temperature to ~95° C. and the fluorescence is monitored at each step. The rising temperature causes protein unfolding and the fluorophore [SYPRO Orange® (Invitrogen) or ANS] partitions itself into the melted protein and hence the overall effect is an increase in fluorescence with increasing temperature. If a drug or ligand is included which binds to the protein, the mid-point of the curve can shift, arising from stabilizing or destabilizing effects (e.g., ligand binding). Thermofluor® can rank binding affinity in a rapid, HTS manner and help setup structure-activity relationship. However, this particular methodology is related to both denaturation of proteins as well as subsequent aggregations of the denatured proteins and the patent clearly indicates that the focus is on the unfolding and denaturation of proteins and as described in column 16, lines 25-56, the fluorescent probes chosen for application of this method are drawn from compounds that are "capable of binding to an unfolded or denatured receptor". However, some of the compounds that are listed (ANS, bis-ANS and JCVJ) are known to bind to aggregates (Lindgren et al., 2005 Biophysical J 88; 4200-4212) and as such no particular emphasis is laid upon distinguishing between denaturation and aggregation events. In contrast, the present invention is specifically directed towards aggregation detection.

As such, one of the embodiments of the present invention encompasses a novel thermal shift assay in which protein is heated up stepwise from room temperature to ~95° C. using a device, including, but not limited to, a microplate reader, a thermocycler, a melting device or similar equipment, preferably with a heating stage that can raise temperature stepwise and record fluorescence change simultaneously, and the fluorescence of externally added dyes of the present invention is monitored at each heating step. Since the dyes that are used in the present invention selectively interact with protein aggregates and not hydrophobic domains exposed by protein unfolding, the increase in fluorescence with increasing temperature is not due to protein unfolding as seen in the technique described in the '141 patent, but rather is due to protein aggregation. Therefore, this particular embodiment of the present invention can be applied to directly targeting at ranking components, including, but not limited to, excipients, salts, buffers, co-solvents, metal ions, preservatives, surfactants, and ligands in protein stabilization by preventing protein aggregation to improve formulations, or to screening drugs (inhibitors) preventing protein aggregates found in some diseases, including, but not limited to, organic synthetic compounds, peptides and proteins (recombinant or natural source). For most proteins, unfolding directly precedes their aggregation. Hence, similar to the unfolding-based Thermofluor® technique, the aggregation-based thermal shift assay technology embodied in this present invention also has the potential to being applied to ranking the affect of additives on protein stability. So, its application can be expanded to more broad fields, including, but not limited to, investigation protein refolding conditions, optimization of recombinant protein expression/purification conditions, protein crystallization conditions, and selection of ligands, drug, vaccine and diagnostic reagents.

Thus, the present invention provides a method of determining temperature dependency of aggregation of a protein. In this method, the following steps are carried out: (i) providing: (a) the protein; (b) two or more dyes, wherein each of the two or more dyes in the presence of an aggregate of the protein has a higher florescent intensity as compared to the fluorescent intensity when measured in the presence of the native monomeric form of the protein, and wherein at least one of the two or more dyes is selected from S13, S25, S39, S42, S43, TOL-2, TOL-3, YAT2134, YAT2135, YAT2148, YAT2149, YAT2150, YAT2213, YAT2214 and YAT2324; (c) means for detecting fluorescence; (ii) forming a first mixture with the protein (a) and the two or more dyes (b); (iii) measuring the amount of fluorescence in the first mixture at prescribed intervals; (iv) heating the first mixture and measuring the amount of fluorescence continuously or incrementally as the temperature of the first mixture is raised; and (iv) comparing the measurements of fluorescence as the temperature is raised in step (iv) with the amount of fluorescence measured in step (iii), thereby determining the temperature dependency of aggregation of the protein.

This just described method can further comprise a test compound (d) for determining whether the test compound decreases aggregation. In other aspects, in step (iv), heating can be carried out in a temperature range of from about 4° C. to about 95° C. Furthermore, in step (iv), incremental measuring can be carried out as the temperature is raised in increments of 1° C., 5° C. or 10° C.

In yet another embodiment, this invention provides a method of determining temperature dependency of aggregation of a protein. To make this determination, the following steps are carried out: (i) providing: (a) the protein; (b) two or more dyes, wherein each of the two or more dyes in the presence of an aggregate of the protein has a higher florescent intensity as compared to the fluorescent intensity when measured in the presence of the native monomeric form of the protein, and wherein at least one of the dyes has the formula

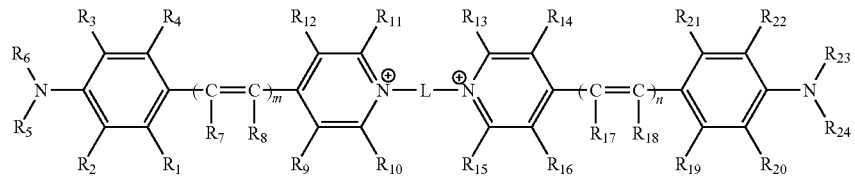

wherein m and n can independently be 1, 2 or 3;

wherein L is a linker arm comprising carbon, sulfur, oxygen, nitrogen, or any combinations thereof;

wherein $R_1$, $R_2$, $R_3$, $R_4$, $R_9$, $R_{10}$, $R_{11}$, $R_{12}$, $R_{13}$, $R_{14}$, $R_{15}$, $R_{16}$, $R_{19}$, $R_{20}$, $R_{21}$ and $R_{22}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken in combination $R_1$ and $R_2$, or $R_3$ and $R_4$, or $R_9$ and $R_{10}$, or $R_{11}$ and $R_{12}$, or $R_{19}$ and $R_{20}$, or $R_{21}$ and $R_{22}$ form a five or six membered ring wherein the ring is saturated or unsaturated, substituted or unsubstituted;

wherein $R_7$, $R_8$, $R_{17}$ and $R_{18}$ can independently be hydrogen, Z, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken together, $R_7$ and $R_8$ and $R_{17}$ and $R_{18}$, may form a 5 or 6 membered ring wherein the ring is saturated or unsaturated, substituted or unsubstituted;

wherein Z comprises a carboxyl group ($CO_2^-$), a carbonate ester ($COER_{25}$), a sulfonate ($SO_3^-$), a sulfonate ester ($SO_2ER_{25}$), a sulfoxide ($SOR_{25}$), a sulfone ($SO_2CR_{25}R_{26}R_{27}$), a sulfonamide ($SO_2NR_{25}R_{26}$), a phosphate ($PO_4^=$), a phosphate monoester ($PO_3^-ER_{25}$), a phosphate diester ($PO_2ER_{25}ER_{26}$), a phosphonate ($PO_3^=$) a phosphonate monoester ($PO_2^-ER_{25}$) a phosphonate diester ($POER_{25}ER_{26}$), a thiophosphate ($PSO_3^=$), a thiophosphate monoester ($PSO_2^-ER_{25}$) a thiophosphate diester ($PSOER_{25}ER_{26}$), a thiophosphonate ($PSO_2^=$), a thiophosphonate monoester ($PSO^-ER_{25}$) a thiophosphonate diester ($PSER_{25}ER_{26}$), a phosphonamide ($PONR_{25}R_{26}NR_{28}R_{29}$), its thioanalogue ($PSNR_{25}R_{26}NR_{28}R_{29}$), a phosphoramide ($PONR_{25}R_{26}NR_{27}NR_{28}R_{29}$), its thioanalogue ($PSNR_{25}R_{26}NR_{27}NR_{28}R_{29}$), a phosphoramidite ($PO_2R_{25}NR_{28}R_{29}$) or its thioanalogue ($POSR_{25}NR_{28}R_{29}$) where E can be independently O or S;

wherein Z is attached directly, or indirectly through a linker arm comprising carbon, sulfur, oxygen, nitrogen, and any combinations thereof and wherein the linker arm may be saturated or unsaturated, linear or branched, substituted or unsubstituted and any combinations thereof;

wherein $R_9$, $R_{10}$, $R_{11}$, $R_{12}$, $R_{13}$, $R_{14}$, $R_{15}$ and $R_{16}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when $R_9$ and $R_{10}$ or $R_{11}$ and $R_{12}$ or $R_{13}$ and $R_{14}$ or $R_{15}$ and $R_{16}$ comprise alkyl chains that are joined together, a quinoline moiety can be formed;

wherein $R_5$, $R_6$, $R_{23}$ and $R_{24}$ can independently be hydrogen or an alkyl group wherein the alkyl group is saturated or unsaturated, linear or branched, substituted or unsubstituted, or when taken in combination $R_5$ and $R_6$ or $R_2$ and $R_5$ or $R_3$ and $R_6$ or $R_{23}$ and $R_{24}$ or $R_{22}$ and $R_{23}$ or $R_{20}$ and $R_{24}$ form a five or six membered ring wherein the ring is saturated or unsaturated, substituted or unsubstituted; and (c) means for detecting fluorescence; (ii) forming a first mixture with the protein (a) and the two or more dyes (b); (iii) measuring the amount of fluorescence in the first mixture; (iv) heating the first mixture and measuring the amount of fluorescence continuously or incrementally as the temperature of the first mixture is raised; and (iv) comparing the measurements of fluorescence as the temperature is in step (iv) with the amount of fluorescence measured in step (iii), thereby determining (measuring) the thermal profile of aggregation of the protein.

In carrying out the just described method, the dyes in the presence of a protein aggregate have emission maxima within 150 nm of each other. Preferably, the emission maxima is within 50 nm. Furthermore, in this method, at least one dye having the formula, further has a structure from FIG. 1B.

The invention described herein also provides a method of determining temperature dependency of aggregation of a protein. Here, the following steps are carried out to determine temperature dependency: (i) providing: (a) the protein; (b) two or more dyes, wherein each of the two or more dyes in the presence of an aggregate of the protein has a higher florescent intensity as compared to the fluorescent intensity when measured in the presence of the native monomeric form of the protein, and wherein the dyes have emission maxima within 150 nm of each other in the presence of an aggregate of the protein; and (c) means for detecting fluorescence; (ii) forming a first mixture with the protein (a) and the two or more dyes (b); (iii) measuring the amount of fluorescence in the first mixture; (iv) heating the first mixture and measuring the amount of fluorescence continuously or incrementally as the temperature is raised; and (iv) comparing the measurements of fluorescence in step (iv) with the amount of fluorescence measured in step (iii), thereby determining the temperature dependency of aggregation of the protein. At least one of the two or more dyes comprises a compound having a structure from FIG. 1B. Preferably, the emission maxima is within 50 nm.

High-Throughput Fluorometric Assay for Measuring Aggregates Formed by Members of the Thioredoxin Superfamily In another embodiment of the present invention, assays are disclosed to measure the activity of thioredoxin-like enzymes by detecting the induction of aggregates formation by means of the dyes of FIG. 1. Such assays can be used to measure the amount of activity in a sample, identify the suitability of proteins as substrates for such activity and to screen for inhibitors of these enzymes. As described previously, a single dye may be used for this purpose or a mixture may be used where at lest one of the dyes is a compound described in FIG. 1. The method of the present invention allows an accurate assay of multiple samples, such as samples from patients, or therapeutic agents for drug discovery. The method can be used in a high throughput manner using a microplate, as reflected in the insulin aggregate detection example included in the present invention.

Thioredoxins and related proteins act as antioxidants by facilitating the reduction of other proteins by cysteine thiol-disulfide exchange. Such exchanges can lead to intermolecular bridges being formed, thereby forming covalently linked aggregates. Thioredoxins are characterized at the level of their amino acid sequence by the presence of two vicinal cysteines in a CXXC motif. These two cysteines are the key to the ability of thioredoxin to reduce other proteins. A number of different families (thioredoxins, protein disulfide isomerases [PDI's] and glutaredoxins) form what can be considered the thioredoxin superfamily. With regard to the glutaredoxins, they share many of the functions of thioredoxins, but are reduced by glutathione rather than a specific reductase and may be assayed by the described methods of the present invention.

The assay of the present invention essentially consists of a process where a mixture is formed comprising a member of the thioredoxin superfamily, its substrate, a reducing agent, assay buffer, and one or more aggregate detection dyes from FIG. 1 or dyes having the structure of a dimeric styrl dye shown previously. In some applications mixture comprises optimized enzyme and substrate concentrations to maximize signal to background ratio. Substrates include, but are not limited to, insulin, hypoxia-inducible factor, prolyl 4-hydroxylase, HIV gp 120, TXNIP, ASK1, Collagen, type I, alpha 1 and Glucocorticoid receptor. In a preferred embodiment, insulin is used as a substrate at a concentration of less than 0.2 mM. The assay of the present invention may also be used to test the ability of a particular protein to be used as a substrate by a member of the thioredoxin superfamily to form aggregates.

The reducing reagent concentration should be optimized to reduce the substrate disulfide bonds without minimizing the competing chemical reaction. The reducing reagents may include, but are not limited to glutathione, dithiothreitol (DTT), dithioerythritol, β-mercaptoethanol, thioglycolate, and cysteine, with DTT being a preferred embodiment. The preferred DTT concentration is less than 10 mM, and more preferably less than 1 mM. The assay buffer can include those buffers that stabilize thioredoxin superfamily members and their substrates, with optimized pH, salts, chelating agents (e.g. EDTA, and the like), dyes, and potentially organic solvents such as DMSO.

When testing for the presence or amount of a particular member of the thioredoxin superfamily in a sample (or for overall activity), a variety of sources may be used that include biological tissues, biological fluids and cells. Thus for instance, samples may include cells up-regulating PDI during hypoxia or cells with surface expressed PDI, including endothelial cells, platelets, lymphocytes, hepatocytes, pancreatic cells and fibroblasts. The sample may also include a thioredoxin superfamily member complexed with other proteins, such as PDI complexed with hypoxia-inducible transcription factor HIFα. Samples may also include fragments of a member of the thioredoxin superfamily as well as recombinant forms of these members, and in vitro protein synthesis reactions that are presumed to have generated such proteins.

The assays of the present invention may also find utility in identifying modulators of thioredoxin superfamily activity; such modulators can comprise enzyme mimetics, interacting proteins, competitive inhibitors, small molecular inhibitors, and the like.

The method may also comprise the use of appropriate controls for the sample, including controls that do not include any thioredoxin superfamily member activity as well as controls that do not include any reducing reagents. These controls can be used as background to be subtracted from gross signal to gain net signal induced by the enzyme activity.

A preferred addition sequence of the present invention is: (1) Substrate and related buffers; (2) Dye(s) dissolved in organic solvent (s), (3) PDI or similar thioredoxin-like enzyme (s) and related buffers; (4) Reducing reagent (s). The enzyme (s) and reducing reagents are preferred to be added with a multi-channel addition device that can simultaneously add reducing agent into the multiple assay containers, such as wells of a microplate to minimize the time interval between the addition of enzyme and the reducing reagent. This may be important for kinetic assays under some circumstances since PDI and similar thioredoxin-like enzymes can induce enzymatic reaction in the absence of reducing agent, especially with a high concentration of enzyme or substrate or both. This can minimize the background levels. The multi-channel addition device can minimize the background levels derived from the foregoing effects it may also minimize timing errors among the multiple samples to be analyzed, which can minimize statistical deviation among the samples.

In addition to the methods described above, the thioredoxin superfamily aggregation assays can be formulated into kits comprising one or more thioredoxin superfamily members, appropriate substrates, buffers, reducing agents and one or more dyes of the described in FIG. 1 as well as instructions for their use. These kits may be used for any of the applications described above.

Thus, the present invention provides a method for measuring activity of a member of the thioredoxin superfamily in which the following steps are carried out: (i) forming a reaction mixture comprising: (a) a member of the thioredoxin superfamily; (b) a substrate for the member of the thioredoxin superfamily; (c) a reducing agent; and (d) one or more of compounds comprising Dye F, Dye Fm(b), D95, D97, L-30, L-33, Lu-1, Lu-2, S-8, S13. S22, S25, S33, S39, S42, S43, S48, S49, SL2131, SL2592, Tio-1, TOL-2, TOL-3, TOL-5, TOL-6, TOL-7, TOL-11, YA-1, YA-3, YAT2134, YAT2135, YAT2148, YAT2149, YAT2150, YAT2213, YAT2214 or YAT2324; (ii) incubating the reaction mixture for a period of time sufficient to reduce disulfide bonds in the substrate; and (iii) measuring the fluorescence intensity of the mixture, wherein an increase in the fluorescence intensity compared with the fluorescence intensity of a negative control is indicative of activity of the member of the thioredoxin superfamily.

Such member of the thioredoxin superfamily (a) can comprise a protein disulfide isomerase, a thioredoxin or a glutaredoxin, and combinations thereof. The substrate (b) in this method can comprise insulin ribonuclease, choriogonadotropin, coagulation factor, glucocorticoid receptor or HIV gp 120, and combinations thereof. The reducing agent (c) can be selected from the group comprising dithiothreitol (DTT), Tris(2-carboxyethyl)phosphine hydrochloride (TCEP HCl) or dithioerythritol (DTE), and combinations thereof. The reaction mixture can be preferably incubated for a period of time from about 15 to about 60 minutes. The protein disulfide isomerase can comprise PDI, ERp57, PDIp, ERp72, P5, PDIr, ERp28/29, ERp44, ERjd5/JPDI or ERp18, and combinations thereof.

This method can further comprise the step of terminating the reaction prior to the measuring step (iii) by adding hydrogen peroxide to the incubating reaction mixture. As in the case of earlier described embodiments of this invention, a plurality of such methods can be performed in parallel.

Chaperone/Anti-Chaperone Activity Assays

Chaperone and anti-chaperone function oppositely in the sense that one helps prevent aggregates and the other helps induce aggregate formation. To assay activity of the opposite functions, one needs to quantitatively analyze the substrate aggregate change with time. The present invention uses methods described above in the PDI/thioredoxin activity assay to analyze chaperone/anti-chaperone activity, which has similar advantages over methods based on other aggregate detection technologies, particularly turbidity and back-scatter methods. The present invention also encompasses a kit or kits comprising similar components as the PDI isomerase activity kit (s) included in the present invention. Assays can be devised to monitor assembly or disassembly of protein aggregates or both.

In connection with this concept, therefore, this invention provides a method for measuring chaperone-like activity in which the following steps are carried out: (i) forming a reaction mixture comprising: (a) a chaperone; (b) a substrate for the chaperone; (c) one or more of compounds comprising Dye F, Dye Fm(b), D95, D97, L-30, L-33, Lu-1, Lu-2, S-8, S13. S22, S25, S33, S39, S42, S43, S48, S49, SL2131, SL2592, Tio-1, TOL-2, TOL-3, TOL-5, TOL-6, TOL-7, TOL-11, YA-1, YA-3, YAT2134, YAT2135, YAT2148, YAT2149, YAT2150, YAT2213, YAT2214 or YAT2324; (ii) exposing the reaction mixture to a stress for a period of time sufficient to induce aggregation of the substrate (b); and (iii) measuring the fluorescence intensity of the exposed mixture, wherein a decrease in the fluorescence intensity compared with the fluorescence intensity of a negative control is indicative of chaperone activity.

In carrying out this just described method, the chaperone comprises a member selected from conserved classes and small heat-shock proteins (sHSPs). Such conserved classes comprise HSP33, HSP60, HSP70, HSP90 or HSP100, and combinations thereof. Furthermore, the chaperone comprises GRP94, GRP170, calnexin, calreticulin, HSP 40, HSP47 and ERp29, GroEL, GroES, HSP60, Cpn10, DnaK, DnaJ, Hsp70, Hsp71, Hsp72, Grp78 (BiP), PDI, Erp72, Hsx70, Hdj1, Hdj2, Mortalin, Hsc70, Hsp70-A1, fHtpG, C62.5, Hsp90 alpha, Hsp90 beta, Grp94, ClpB, ClpA, ClpX, Hsp100, Hsp104, Hsp110, TRiC, alpha crystallin, HspB1, Hsp 25, Hsp27, clusterin, GrpE, Trigger Factor, or Survival of Motor Neuron (SMN1, SMN2), and combinations thereof. The substrate (b) can comprise R-lactoglobulin, citrate synthase, lysozyme, imuunoglobulin, CRYBB2, HSPB8, CRYAA, TGFB1I1, HNRPD or CRYAB, and combinations thereof. The reaction mixture can be incubated for a period of time from about 15 to about 60 minutes. The stress can be an elevated temperature, preferably, from about 37° C. to about 95° C. Alternatively, the stress can be a chaotropic agent, such as guanidine-HCl or urea, or both. The concentration of the chaotropic agent can be from about 4 to 8 M. Moreover, a plurality of these methods can be performed in parallel.

Reagent Kits:

Commercial kits are valuable because they eliminate the need for individual laboratories to optimize procedures, saving both time and resources. They also allow better cross-comparison of results generated from different laboratories. The present invention additionally provides reagent kits, i.e., reagent combinations or means, comprising all of the essential elements required to conduct a desired assay method. The reagent system is presented in a commercially packaged form, as a composition or admixture where the compatibility of the reagents will allow, in a test kit, i.e., a packaged combination of one or more containers, devices or the like holding the necessary reagents, and usually written instructions for the performance of the assays. Reagent systems of the present invention include all configurations and compositions for performing the various labeling and staining formats described herein.

The reagent system will generally comprise (1) one or more dye of the present invention preferably in the form of concentrated stock solutions in an aprotic dipolar solvent, for example, DMSO designed to target specific protein aggregate structures; (2) a buffer, such as Tris-HCl or phosphate buffer; (3) a positive control comprising both protein aggregates and protein monomers in the state of solution or lyophilized powder; and (4) instructions for usage of the included reagents. Generic instruction, as well as specific instructions for the use of the reagents on particular instruments, such as a wide-field microscope, confocal microscope, flow cytometer, high content screening instrument, microplate-based detection platform, RT-PCR instrument or standard fluorometer may be provided. Recommendations regarding filter sets and/or illumination sources for optimal performance of the reagents for a particular application may be provided.

Assaying Various Enzymatic Activities and Post-Translational Modifications by Monitoring Protein Aggregation Status.

With respect to various pathological disorders, abnormal protein aggregates are often sequestered into intracellular protein deposits such as aggresomes, aggresome-like structures, inclusion bodies. Lewy bodies or Mallory bodies (Stefani (2004) "Protein misfolding and aggregation: new examples in medicine and biology of the dark side of the protein world". *Biochimica et Biophysica Acta* 1739: 5-25; Garcia-Mata et al (2002) "Hassles with Taking Out the Garbage: Aggravating Aggresomes" *Traffic;* 3: 388-396). These may trigger in turn the expression of inflammatory mediators, such as cyclooxygenase 2 (COX-2) (Li et al "Δ12-Prostaglandin J2 inhibits the ubiquitin hydrolase UCH-L1 and elicits ubiquitin—protein aggregation without proteasome inhibition". *Biochemical and Biophysical Research Communications* 319 (2004) 1171-1180). Disruption of the ubiquitin—proteasome pathway, as for example, thru impairment of ubiquitin hydrolase activity, triggered by modulators such as Δ12-PGJ2, Lactacystin β-Lactone or MG-132 can readily be analyzed directly in cells using the disclosed methods to detect intracellular protein deposits as well as in either cell-based or biochemical assays for screening of other selective inhibitors of the ubiquitin—proteasome pathway that lead to protein aggregation.

The principle advantages of the delineated approach relative to use of conventional substrates of ubiquitin hydrolase activity, such as ubiquitin-7-amino-4-methylcoumarin (ubiquitin-AMC), include employment of a natural protein substrate in the assay as well as an inherent signal amplification, arising from the formation of polymerized amyloid fibrils as reporters. Examples of potential protein substrates useful in this regard include, but are not limited to, α-synuclein, synphilin-1, TCRα, P23H mutant of rhodopsin, ΔF508 mutant of CFTR, amyloid-β, prion protein, Tau, SOD1, Ig light chains, ataxin-1, ataxin-3, ataxin-7, calcium channel, atrophin-1, androgen receptor, p62/sequestosome1 (SQSTM1), Pael receptor, serum amyloid A, transthyretin, β2-microglobulin, apolipoprotein A-1, gelsolin, atrial natriuretic factor, lysozyme, insulin, fibrinogen, crystallins, surfactant protein C, lactoferrin, βig-h3, PAPB2, corneodesmosin, neuroserpin, cochlin, RET, myelin, protein 22/0, SCAD, prolactin, lactadherin, p53, procalcitonin, cytokeratins, GFAP, ATP7B, prolyl hydroxylase PHD3, presenilin, and huntingtin. Additionally, proteins specifically engineered to be unstable or highly prone to self-association into aggregates may be employed as substrates using the disclosed assay methods.

With respect to coupled enzyme reactions the product of one reaction is used as the substrate of another, more easily-detectable reaction. The cited compositions and methods are especially advantageous in the development of biochemical assays involving coupled reactions leading to the formation of protein aggregates. In this instance no meaningful physiological relationship between the activity being monitored and the generation of the aggregated protein-dye reporter is explicitly required. The protein aggregate-dye complex is simply serving as an indicator to establish the amount of product formed in a particular catalytic reaction. For example, a protein substrate may be employed that is marginally stable under the specified solution conditions employed in the assay. When this substrate is acted upon by a histone acetyltransferase, a particular lysine residue becomes acetylated, the overall protein structure is destabilized and the protein undergoes a conformational change resulting in its aggregation. The dyes described in this disclosure are then able to bind to the aggregates, generating a fluorescent signal. While illustrated with histone acetyltransferase, a wide range of activities that could potentially modify a substrate protein, leading to its structural destabilization under the assay conditions employed, could be performed by similar approaches. In addition activities that do not directly modify the substrate protein can also be considered. For instance, an enzyme activity that leads to the acidification of the assay buffer could in turn lead to destabilization of the substrate protein structure and its aggregation.

Separation of Protein Aggregates from Protein Monomers

Those skilled in the art will appreciate that the present invention is applicable to the separation or isolation of protein aggregates from other protein forms, notably protein monomers. The dyes described above are useful in subtraction of protein aggregates from protein monomers.

Thus, the present invention provides a method for separating aggregates of proteins from monomeric forms of the proteins. In this separation method, the following steps are carried out: (i) providing: (a) a sample that having aggregates of the proteins and monomeric forms of the proteins; (b) one or more compounds, wherein at least one of the compounds is selected from Dye F, Dye Fm(b), D95, D97, L-30, L-33, Lu-1, Lu-2, S-8, S13. S22, S25, S33, S39, S42, S43, S48, S49, SL2131, SL2592, Tio-1, TOL-2, TOL-3, TOL-5, TOL-6, TOL-7, TOL-11, YA-1, YA-3, YAT2134, YAT2135, YAT2148, YAT2149, YAT2150, YAT2213, YAT2214 and YAT2324, and wherein one or more compounds are attached to a solid matrix; (ii) forming under binding conditions a mixture with the sample (a) and one or more dyes (b) to allow binding between one or more compounds (b) and any aggregates of the proteins in the sample (a); and (iii) separating unbound proteins from the aggregates bound to the one or more compounds (a) in step (ii).

In carrying out the above isolation method, the solid support can comprise glass particle, glass surface, natural polymers, synthetic polymers, plastic particle, plastic surface, silicaceous particle, silicaceous surface, glass, plastic or latex beads, controlled pore glass, metal particle, metal oxide particle, microplate or microarray, and combinations of any of the foregoing.

In another aspect of isolation and separation, this invention provides a method for separating aggregates of proteins from monomeric forms of the proteins. In this case, the following steps are carried out: (i) providing: (a) a sample suspected of having aggregates of proteins and monomeric forms of the proteins; (b) two or more dyes, wherein each of the two or more dyes in the presence of an aggregate of the protein has a higher florescent intensity as compared to the fluorescent intensity when measured in the presence of the native monomeric form of the protein, and wherein at least one of the dyes has the formula

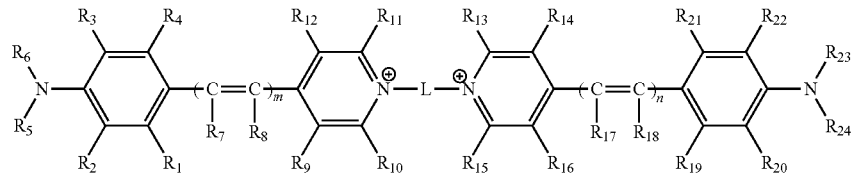

wherein m and n can independently be 1, 2 or 3;

wherein L is a linker arm comprising carbon, sulfur, oxygen, nitrogen, or any combinations thereof;

wherein $R_1$, $R_2$, $R_3$, $R_4$, $R_9$, $R_{10}$, $R_{11}$, $R_{12}$, $R_{13}$, $R_{14}$, $R_{15}$, $R_{16}$, $R_{19}$, $R_{20}$, $R_{21}$ and $R_{22}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken in combination $R_1$ and $R_2$, or $R_3$ and $R_4$, or $R_9$ and $R_{10}$, or $R_{11}$ and $R_{12}$, or $R_{19}$ and $R_{20}$, or $R_{21}$ and $R_{22}$ form a five or six membered ring wherein the ring is saturated or unsaturated, substituted or unsubstituted;

wherein $R_7$, $R_8$, $R_{17}$ and $R_{18}$ can independently be hydrogen, Z, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken together, $R_7$ and $R_8$ and $R_{17}$ and $R_{18}$, may form a 5 or 6 membered ring wherein the ring is saturated or unsaturated, substituted or unsubstituted;

wherein Z comprises a carboxyl group ($CO_2^-$), a carbonate ester ($COER_{25}$), a sulfonate ($SO_3^-$), a sulfonate ester ($SO_2ER_{25}$), a sulfoxide ($SOR_{25}$), a sulfone ($SO_2CR_{25}R_{26}R_{27}$), a sulfonamide ($SO_2NR_{25}R_{26}$), a phosphate ($PO_4^=$), a phosphate monoester ($PO_3^-ER_{25}$), a phosphate diester ($PO_2ER_{25}ER_{26}$), a phosphonate ($PO_3^=$) a phosphonate monoester ($PO_2^-ER_{25}$) a phosphonate diester ($POER_{25}ER_{26}$), a thiophosphate ($PSO_3^=$), a thiophosphate monoester ($PSO_2^-ER_{25}$) a thiophosphate diester ($PSOER_{25}ER_{26}$), a thiophosphonate ($PSO_2^=$), a thiophosphonate monoester ($PSO^-ER_{25}$) a thiophosphonate diester ($PSER_{25}ER_{26}$), a phosphonamide ($PONR_{25}R_{26}NR_{28}R_{29}$), its thioanalogue ($PSNR_{25}R_{26}NR_{28}R_{29}$), a phosphoramide ($PONR_{25}R_{26}NR_{27}NR_{28}R_{29}$), its thioanalogue ($PSNR_{25}R_{26}NR_{27}NR_{28}R_{29}$), a phosphoramidite ($PO_2R_{25}NR_{28}R_{29}$) or its thioanalogue ($POSR_{25}NR_{28}R_{29}$) where E can be independently O or S;

wherein Z is attached directly, or indirectly through a linker arm comprising carbon, sulfur, oxygen, nitrogen, and any combinations thereof and wherein the linker arm may be saturated or unsaturated, linear or branched, substituted or unsubstituted and any combinations thereof;

wherein $R_9$, $R_{10}$, $R_{11}$, $R_{12}$, $R_{13}$, $R_{14}$, $R_{15}$ and $R_{16}$ can independently be hydrogen, halogen, amino, ammonium, nitro, sulfo, sulfonamide, carboxy, ester, cyano, phenyl, benzyl, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when $R_9$ and $R_{10}$ or $R_{11}$ and $R_{12}$ or $R_{13}$ and $R_{14}$ or $R_{15}$ and $R_{16}$ comprise alkyl chains that are joined together, a quinoline moiety can be formed;

wherein $R_5$, $R_6$, $R_{23}$ and $R_{24}$ can independently be hydrogen or an alkyl group wherein the alkyl group is saturated or unsaturated, linear or branched, substituted or unsubstituted, or when taken in combination $R_5$ and $R_6$ or $R_2$ and $R_5$ or $R_3$ and $R_6$ or $R_{23}$ and $R_{24}$ or $R_{22}$ and $R_{23}$ or $R_{20}$ and $R_{24}$ form a five or six membered ring wherein the ring is saturated or unsaturated, substituted or unsubstituted; and, and wherein at least of said one or more compounds is attached to a solid support; (ii) forming under binding conditions a mixture with the sample (a) and the one or more dyes (b) to allow binding between the one or more compounds (b) and any aggregates of the proteins in the sample (a); and (iii) separating unbound proteins from the aggregates bound to the one or more compounds (a) in step (ii).

The solid support can comprise glass particle, glass surface, natural polymers, synthetic polymers, plastic particle, plastic surface, silicaceous particle, silicaceous surface, glass, plastic or latex beads, controlled pore glass, metal particle, metal oxide particle, microplate or microarray, and combinations of any of the foregoing.

The following examples are put forth so as to provide those of ordinary skill in the art with a complete disclosure and description of how to make and use the present invention, and are not intended to limit the scope of what the inventors regard as their invention nor are they intended to represent that experiments are all or the only experiments performed.

DESCRIPTION OF THE PREFERRED EMBODIMENTS

Table 1 summarizes the spectral properties of various dyes freely dissolved in buffer and in the presence of monomeric and aggregated protein according to the present invention. Immediately following Table 1 is Table 2 which provides excipient sensitivity of fluorescence enhancement (fold) for different protein aggregate sensors, using IgG (Goat-Anti-Mouse).

TABLE 1

Maximum Fluorescence excitation and emission wavelengths of protein aggregation sensors

| Dye | Dye freely dissolved in buffer: Excitation wavelength (nm) | Dye freely dissolved in buffer: Emission wavelength (nm) | In the presence of aggregate: Excitation wavelength (nm) | In the presence of aggregate: Emission wavelength (nm) |
|---|---|---|---|---|
| S25 | 485 | 613 | 516 | 607 |
| TOL3 | 471 | 611 | 511 | 603 |
| S43 | 527 | 637 | 550 | 623 |
| Yat 2134 | 500 | 620 | 535 | 613 |
| Yat 2148 | 520 | 632 | 553 | 625 |
| Yat 2149 | 502 | 614 | 534 | 617 |
| Yat 2150 | 485 | 612 | 515 | 610 |
| Thioflavin-T | 400 | 472 | 447 | 480 |

Fluorescent readings were carried out in 50 mM Tris-HCl, pH 7.8 using 10 µM dye. When present, 1 µM recombinant human alpha-synuclein (ASN, Sigma-Aldrich, St. Louis, Mo.) aggregated as described [van Raaij, M. E.; Segers-Nolten, I. M.; Subramaniam, V. *Biophys J.* 2006, 91, L96] was included. Fluorescence excitation and emission spectra were collected on a Cary Eclipse fluorescence spectrophotometer (Varian, Australia). Fluorescence spectra were measured with excitation and emission slit widths set to 5 nm, and at a constant PMT voltage. Spectroscopic measurements were performed in standard quartz cells. All measurements were made at the respective excitation maxima of each dye. All measurements were carried out at room temperature.

TABLE 2

Fluorescence sensitivity for different protein aggregate sensing dyes in the presence of excipients

| Excipients & Concentrations | S25 | TOL3 | Y2150 | Thio-T |
|---|---|---|---|---|
| Sodium Chloride, 10 mM | 14.0 | 16.0 | 14.4 | 1.6 |
| Sodium Chloride, 100 mM | 13.6 | 16.2 | 11.3 | 1.3 |
| Sodium Chloride, 1000 mM | 11.7 | 17.4 | 15.0 | 2.7 |
| Calcium Chloride, 10 mM | 9.7 | 14.9 | 12.4 | 3.1 |
| Calcium Chloride, 50 mM | 9.6 | 13.9 | 14.7 | 1.5 |
| Calcium Chloride, 200 mM | 6.7 | 14.8 | 13.9 | 1.7 |
| Ammonium Sulfate, 10 mM | 15.4 | 15.6 | 12.4 | 2.8 |
| Ammonium Sulfate, 100 mM | 14.6 | 13.4 | 12.5 | 2.6 |
| Ammonium Sulfate, 300 mM | 13.3 | 16.9 | 14.6 | 1.4 |
| Sorbitol, 100 mM | 16.4 | 20.0 | 17.3 | 3.0 |
| Sorbitol, 300 mM | 21.0 | 19.2 | 15.6 | 1.9 |
| Sorbitol, 600 mM | 25.4 | 29.3 | 18.7 | 3.6 |
| Mannitol, 100 mM | 16.7 | 17.5 | 11.2 | 3.1 |
| Mannitol, 300 mM | 15.2 | 25.2 | 13.8 | 3.7 |
| Mannitol, 600 mM | 20.9 | 27.5 | 17.7 | 1.8 |
| Trehalose, 100 mM | 17.8 | 18.9 | 14.0 | 2.2 |
| Trehalose, 300 mM | 32.1 | 20.1 | 19.4 | 0.2 |
| Trehalose, 600 mM | 30.1 | 30.4 | 18.9 | 4.8 |
| Lactose, 100 mM | 23.0 | 19.9 | 17.5 | 1.2 |
| Lactose, 300 mM | 38.9 | 34.6 | 31.0 | 1.4 |
| Ascoric Acid, 1 mM | 13.9 | 15.4 | 14.5 | 1.5 |
| X100, 0.01% | 19.2 | 6.2 | 4.1 | 5.3 |

TABLE 2-continued

Fluorescence sensitivity for different protein aggregate sensing dyes in the presence of excipients

| Excipients & Concentrations | S25 | TOL3 | Y2150 | Thio-T |
|---|---|---|---|---|
| X100, 0.2% | 7.3 | 3.4 | 2.6 | 6.6 |
| X100, 1% | 2.9 | 1.9 | 1.7 | 3.4 |
| Arginine, 200 mM | 14.8 | 18.6 | 14.4 | 1.4 |
| Arginine, 500 mM | 13.5 | 17.6 | 14.3 | 2.0 |
| Glycine, 0.5% | 14.1 | 16.3 | 12.5 | 3.1 |
| Glycine, 2% | 15.1 | 15.5 | 19.0 | 3.2 |
| Tween 20, 0.01% | 70.8 | 8.5 | 5.5 | 4.6 |
| Tween 20, 0.2% | 26.7 | 3.4 | 2.6 | 2.6 |
| DTT, 1 mM | 13.2 | 13.8 | 11.3 | 1.6 |
| Average | 19.3 | 17.6 | 14.8 | 2.9 |

IgG aggregate was prepared by adjusting 5.83 mg/ml of purified goat-anti-mouse IgG (H&L, Pel Freez, Rogers, Ark.) to pH 2.7 using HCl and incubating at 22° C. for 24 hours. The assay was performed using 2.8 µM IgG, either native or aggregated, and a dye concentration of 0.625 µM. The protein and dye were mixed together for 15 minutes at 22° C., then this was further incubated in the presence of the excipients shown in the table. The fluorescence intensity of S-25, Tol3 and Y2150 were determined with a FLUOstar OPTIMA plate reader (BMG LABTECH) at excitation wavelength of 550 nm and emission wavelength of 610 nm; while the fluorescence intensity for Thioflavin-T was determined using a SpectraMAX GeminiXS (Molecular device, with Softmax Pro 7.0) using an excitation wavelength of 435 nm and emission wavelength of 495 nm. The fluorescence enhancement (aggregate/native IgG) is shown.

Example 1 Synthesis of S25

(a) Preparation of 6-methylsulfonyloxyhexyl methylsulfonate (Compound 1)

A solution of 1,6-hexanediol (13.15 g, 111.3 mmol) in 70 mL of anhydrous pyridine was cooled to 0° C. using ice bath. To this methanesulfonyl chloride (27 g, 235.7 mmol) was slowly added under mixing such that the temperature was maintained at 5-6° C. The combined mixture was stirred overnight at the temperature below 10° C. and the precipitate formed was filtered off, washed with 20% HCl (3×), water (3×), 5% solution of sodium bicarbonate (3×), and then again with water (3×). Product was dried under vacuum to obtain Compound 1 as a white solid (yield 32.8%). The structure of Compound 1 is given below:

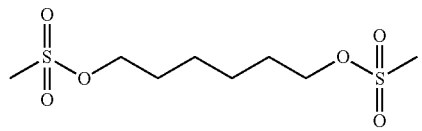

Compound 1

(b) Preparation of Compound 2

A mixture of 4-methylpyridine (3.06 g, 32.9 mmol) and Compound 1 (4.11 g, 15 mmol) was heated at 120° C. for 3 hours. The reaction mixture was cooled and then 4 mL of isopropyl alcohol was added and the combined mixture was refluxed for an hour. After cooling the precipitate was collected by centrifugation, washed with isopropyl alcohol (40 mL, 3×), followed by diethyl ether (40 ml, 3×) and dried under vacuum overnight to provide Compound 2 (yield 85%) which was then used without any further purification. The structure of Compound 2 is given below:

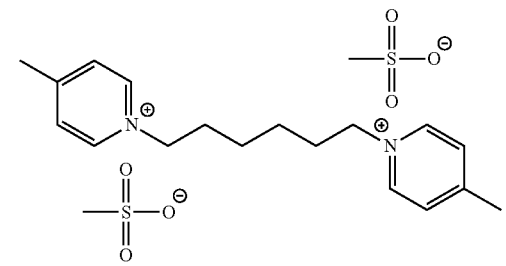

Compound 2

(c) Preparation of S-25

To a suspension of Compound 2 (1.38 g) in n-butanol (15 mL), p-dimethylaminobenzaldehyde (0.9 g) was added and the combined mixture was stirred until it became homogeneous. To this mixture ~24 drops of piperidine was added and it was refluxed for 4.5 hours. Upon cooling, the precipitate formed was collected by centrifugation, washed with isopropyl alcohol (40 ml, 3×), diethyl ether (40 ml, 2×) and dried under vacuum to provide dye S25 in a yield of about 68%. Abs=485 nm, Em=613 nm. The structure of S25 is given below:

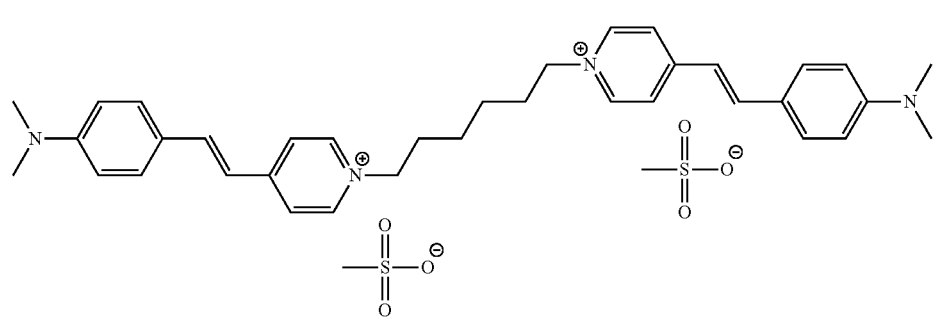

S25

Example 2 Synthesis of Tol3

(a) Preparation of Compound 3

A mixture of 3,4-dimethylpyridine (1.18 g, 11 mmol) and 1,10-diiododecane (1.97 g, 5 mmol) was alloyed during 3 hours at 120° C. To the reaction mixture 5 mL of isopropyl alcohol was added and the mixture was refluxed for an hour. Upon cooling, the solvent was decanted, and the residue thus obtained was washed with cold diethyl ether (40 ml, 2×), followed by centrifugation to remove residual solvents. The solid obtained was then dissolved in methanol (~4 mL) and dropwise added to cold diethyl ether. Precipitated product was collected by centrifugation, washed with diethyl ether (40 ml, 3×) and dried under vacuum to provide Compound 3 in 88% yield. This product was used without any further purification. The structure of Compound 3 is given below:

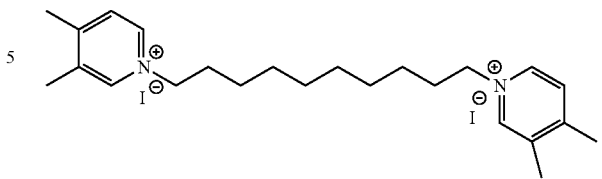

Compound 3

(b) Preparation of Tol3

A mixture of Compound 3 (0.61 g), p-dimethylaminobenzaldehyde (0.3 g) and 6-8 drops of piperidine in 5 mL of n-butanol was refluxed for 4 hours. After cooling the precipitated solid was collected by centrifugation, washed first with isopropyl alcohol (40 ml, 3×), diethyl ether (40 ml, 2×) and then again isopropyl alcohol (40 ml, 1×) and diethyl ether (40 ml, 3×). The product was dried under vacuum to provide dye Tol3 in 82% yield. Abs=471 nm, Em=611 nm. The structure of Tol3 is given below:

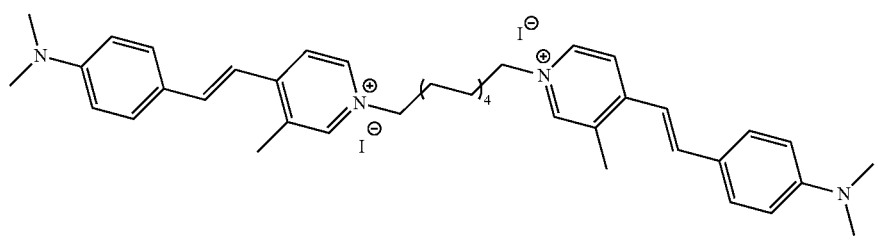

Tol3

Example 3 Synthesis of S43

(a) Preparation of 1,1'-(1,2-phenylenebis(methylene))bis(4-methyl pyridinium) bromide (Compound 4)

A mixture of 4-methylpyridine (1.02 g) and 1,2-bis-bromomethyl-benzene (1.32 g) was heated during 2.5 hours at 120° C. To the reaction mixture 5 mL of isopropyl alcohol was added and the mixture was refluxed for 2 hours. After cooling the product was filtered, washed with diethyl ether and dried under vacuum to provide Compound 4 in 87% yield. The structure of Compound 4 is given below:

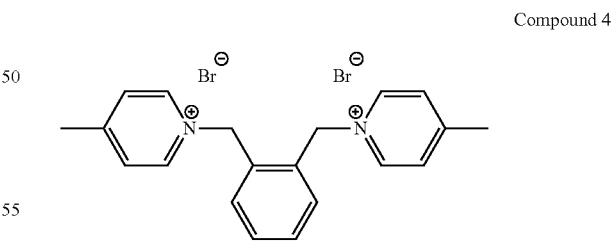

Compound 4

(b) Preparation of S43

A mixture of Compound 4 (0.45 g), p-dimethylaminobenzaldehyde (0.3 g) and 6 drops of piperidine in 5 mL of n-butanol were refluxed for 4 hours. After cooling the product was filtered and washed with isopropyl alcohol and diethyl ether. The residue obtained was recrystallized from the DMF-methanol mixture to provide S43 in 72% yield. Abs=527 nm, Em=637 nm. The structure of S43 is given below:

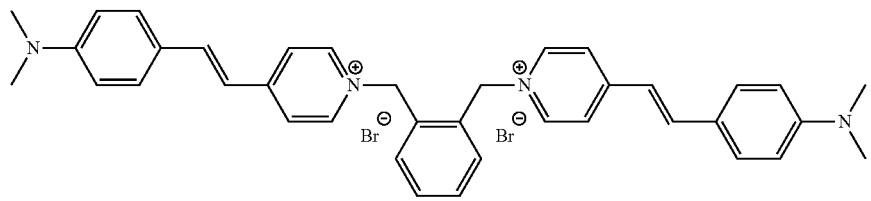

S43

Example 4 Synthesis of Yat 2134

(a) Preparation of 1,1'-(butane-1,4-diyl)bis(4-methylpyridinium) iodide (Compound 5)

A mixture of 4-methylpyridine (1.02 g) and 1,4-diiodobutane (1.55 g) in 5 mL of dioxane was refluxed for 8 hours. The obtained salt was precipitated with diethyl ether and filtered. The precipitate was washed with ether and dried under vacuum to provide Compound 5 in 91% yield. This product was used without any further purification. The structure of Compound 5 is given below:

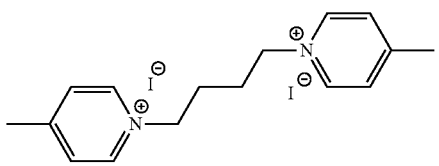

Compound 5

(b) Preparation of Yat 2134

This procedure was carried out as described previously in step (b) of Example 3 with Compound 5 (0.5 g), piperidine (~6 drops), p-diethylamino benzaldehyde (0.36 g) and n-butanol (5 mL). Purification was carried out by recrystallization from DMF-methanol mixture to provide Yat 2134 in 70% yield. Abs=500 nm, Em=620 nm. The structure of Yat 2134 is given below:

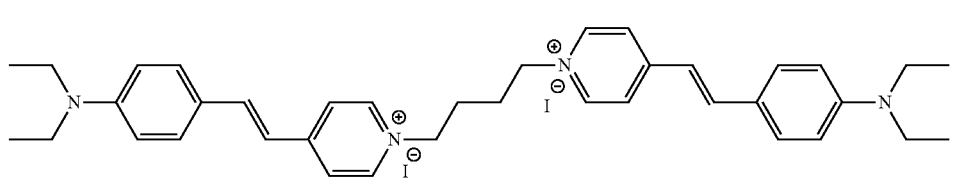

Yat 2134

Example 5 Synthesis of Yat 2148

A mixture of Compound 4 [0.45 g, obtained in step (a) of Example 3], p-dimethylaminobenzaldehyde (0.36 g) and 6 drops of piperidine in 5 mL of n-butanol was refluxed for 4 hours. Upon cooling the product was filtered and washed with isopropyl alcohol and diethyl ether. The crude dye obtained was recrystallized from the DMF-methanol mixture to provide Yat 2148 in 69% yield. Abs=520 nm, Em=632 nm. The structure of Yat 2148 is given below:

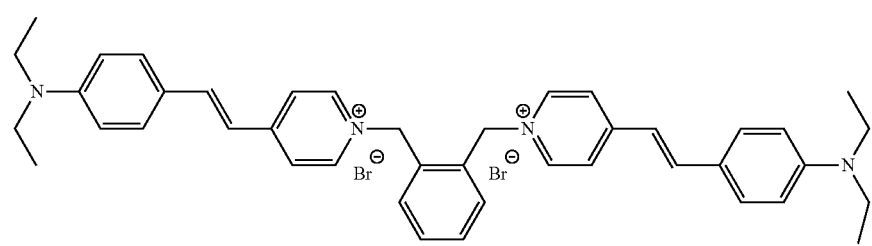

Yat2148

Example 6 Synthesis of Yat 2149

(a) Preparation of 1,1'(2,2'-oxybis(ethane-2,1-diyl))bis(4-methylpyridinium) chloride (Compound 6)

A mixture of 4-methylpyridine (1.02 g) and 0.72 g of 1-Chloro-2-(2-chloro-ethoxy)-ethane (0.72 g) was heated at 120-130° C. for 3-4 hours. To the reaction mixture 5 mL of isopropyl alcohol was added and the mixture was refluxed for an hour. Upon cooling the product was filtered and washed with diethyl ether to provide Compound 6 in 81% yield. This product was used without any further purification. The structure of Compound 6 is given below:

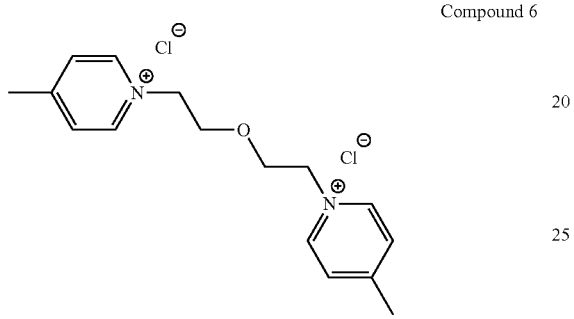

Compound 6

(b) Preparation of Yat 2149

This procedure was carried out as described previously in step (b) of Example 3 with Compound 6 (0.33 g), piperidine (~6 drops), p-diethylamino benzaldehyde (0.36 g) and n-butanol (5 mL). After cooling the dye was precipitated with isopropyl alcohol or diethyl ether. In order to obtain the iodide salt, a saturated aqueous solution of KI (0.34 g) was added to the dye solution in methanol. After cooling, the product was filtered, washed with isopropyl alcohol, diethyl ether and dried under vacuum to provide Yat 2149 in 65% yield. Abs=502 nm, Em=614 nm. The structure of Yat 2149 is given below:

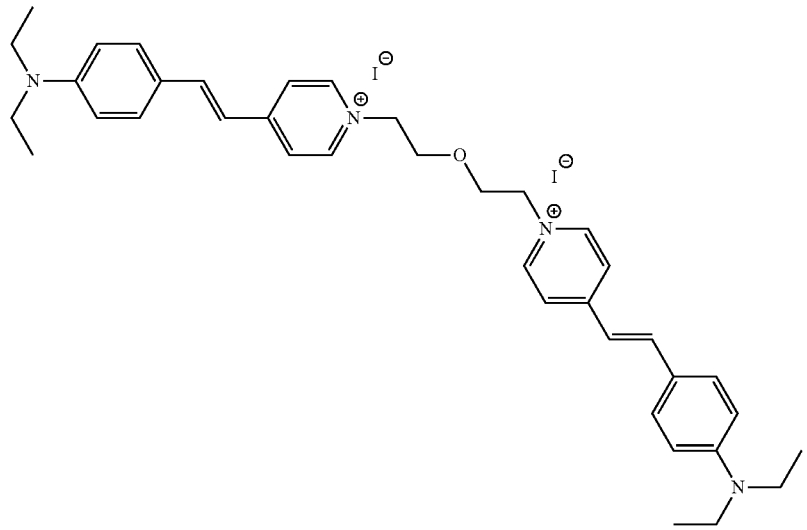

Yat2149

Example 7 Synthesis of Yat 2150

This procedure was carried out as described previously in step (b) of Example 2 with Compound 3 (0.61 g), piperidine (~5 drops), p-diethylamino benzaldehyde (0.36 g) and n-butanol (5 mL). Purification was carried out by recrystallization from DMF-methanol mixture to provide Yat 2150 in 71% yield. Abs=485 nm, Em=612 nm. The structure of Yat 2150 is given below:

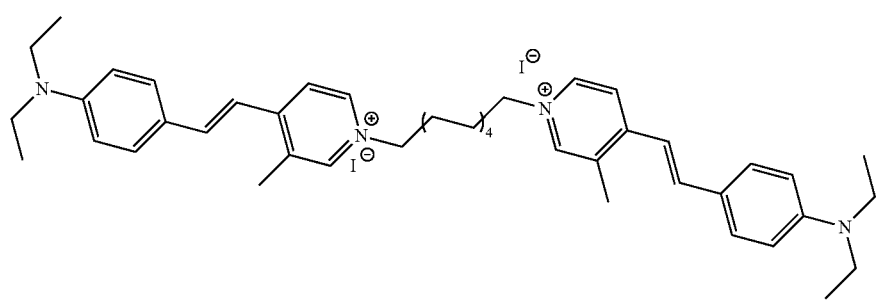

Yat2150

Example 8 Monitoring Protein Stability in Two Different Buffer Formulations

Goat anti-mouse IgG from Vector Labs (1.5 mg) was resuspended in 150 μl deionized water (dH$_2$O). Phosphate was removed from the IgG using an Ambion NucAway spin column, following the manufacturer's instructions, briefly the column was resuspended in 700 μl dH$_2$O and allowed to hydrate for 60 minutes. Excess liquid was removed by centrifugation at 700×g for 2 minutes. The column was placed in a fresh collection tube and the sample was carefully loaded on the center of the column. The IgG was eluted by centrifugation at 700×g for 2 minutes. The purified IgG was diluted 10 fold in either 100 mM HCl or 12 mM Phosphate pH 7.4, 150 mM sodium chloride. The samples were incubated for 18 hours at 37° C. The solutions were stained with a final concentration of 100 mM MES, pH 6, 0.25 mg/ml IgG, 3 μM S-25 and 3 μM Tol3 (1:1 ratio) for at least 15 minutes. The stained protein was spotted on the surface of a glass microscope slide and overlaid with a cover slip, sealed with nail polish and observed using a BX51 microscope (Olympus, Tokyo, Japan). Images were acquired with a 40× objective lens (Olympus). Fluorescent images were acquired using a Texas Red filter set (Chroma Technoloogy Corp., Rockingham, Vt.). FIG. 3 shows that fibrils were formed in HCl solution, but not in the neutral phosphate buffer. The fibrils formed exhibited fluorescence that was bright and specific to the fibers using the S-25 and Tol3 dye mixture. There was little or no fluorescence when fibrils had not formed.

Figure 4:
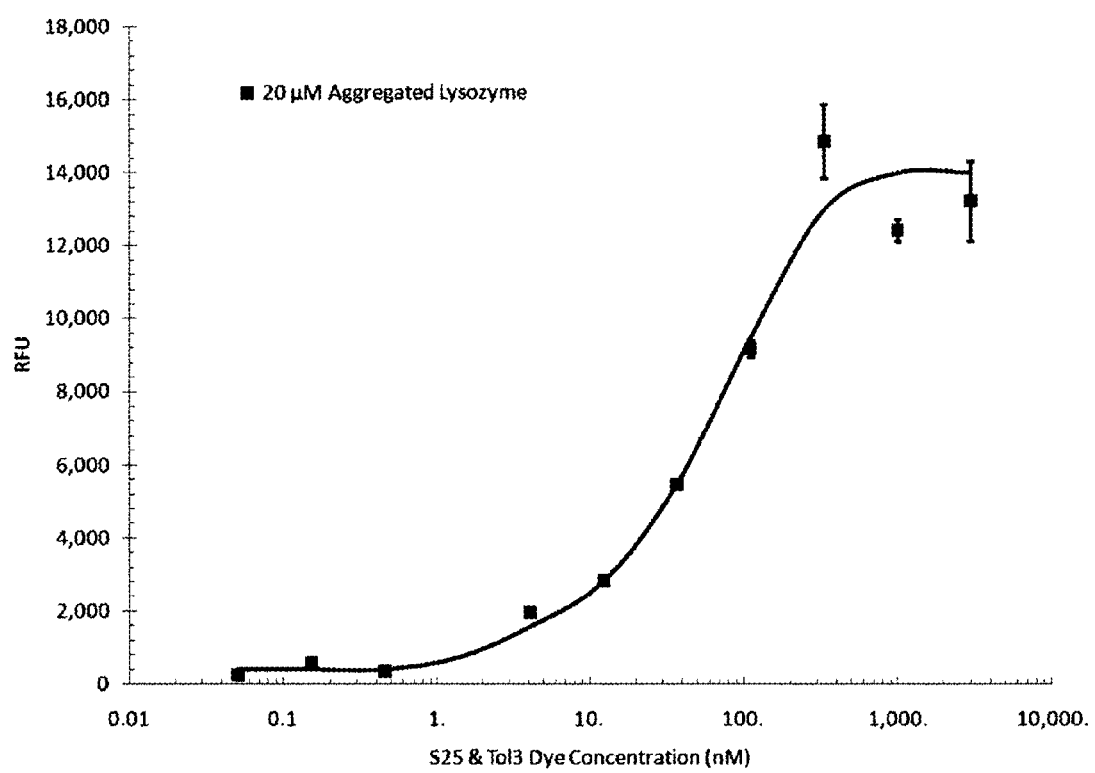
FIG. 4 shows the binding curves of different fluorescent probes with 20 µM of aggregated Lysozyme.

Example 9 Binding Curve of Different Fluorescent Probes to 20 uM of Aggregated Lysozyme Protein Lysozyme aggregates were formed by dissolving Lysozyme in 10 mM HCl to make a 1 mM Lysozyme solution (14.8 mg/ml). The Lysozyme solution was heated to 65° C. with shaking at 750 rpm in an Eppendorf thermomixer for 90 hours. The lysozyme was diluted to 20 μM in a 50 mM potassium phosphate solution containing different concentrations of a mixture of the dyes S-25 and Tol3. The aggregate was incubated for 15 minutes prior to measuring the fluorescence using a BioTek SynergyMx plate scanner, with excitation set at 515 nm and emission set to 603 nm, both with a 9 nm slit-width. Readings were taken in at least triplicate in a Greiner μClear black, clear bottom 96-well microplate. As can be seen in FIG. 4, there is little or no signal generate with up to 1 nM of each of the dyes. Above 1 nM, the signal increases until about 1 μM each of the dyes, at which point no further signal increase is observed. This indicates that above 1 μM S-25 and 1 μM Tol3, the fluorescence of 20 μM aggregated Lysozyme is dependent on aggregate concentration, and not dye concentration.

Example 10 pH Sensitivity of Fluorescence Response to Aggregated Lysozyme

Chicken egg white lysozyme (Sigma-Aldrich) was dissolved at 1 mM in 10 mM HCl. This monomer solution was stored at 4° C. Lysozyme aggregate was formed by shaking the protein solution at 750 rpm in a Thermomixer (Eppendorf) at 65° C. for 90 hours. The aggregation process was monitored by Thioflavin T binding and after saturation of the fluorescence signal (for lysozyme after 90 hrs), the aggregate solution was also stored at 4° C.

Figure 5A:
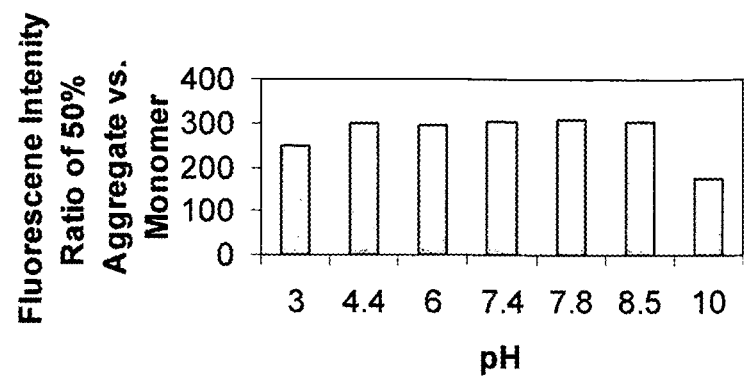
FIGS. 5A and 5B show the effect of pH on fluorescent detection sensitivity and linearity for different probes of the invention.

FIG. 5A. The effect of pH on the aggregation-specific fluorescence of the dyes S-25 ant Tol3 was determined by incubation of 4 μM aggregated lysozyme, 4 μM monomer lysozyme (or 8 μM lysozyme monomer alone) with 0.5 μM S-25 and 0.5 μM Tol3 in buffers with a pH ranging from 3~10. The buffers used were: 8 mM of Glycine-HCl of pH 3; 8 mM of sodium acetate, pH 4.4; 8 mM ammonium acetate, pH 6.0; 8 mM of Tris-HCl of pH 7.4; 40 mM of Tris-HCl, pH 7.8; 8 mM of Tris-HCl of pH 8.5; and 8 mM of sodium carbonate, pH 10. The dye-protein mixture was incubated at room temperature (22° C.) for at least 15 minutes. Four replicates for either the 50% aggregate or monomer at each pH were prepared and the plate was scanned on a FLUOstar OPTIMA plate reader using an excitation wavelength of 550 nm and an emission of 610 nm.

Figure 5B:
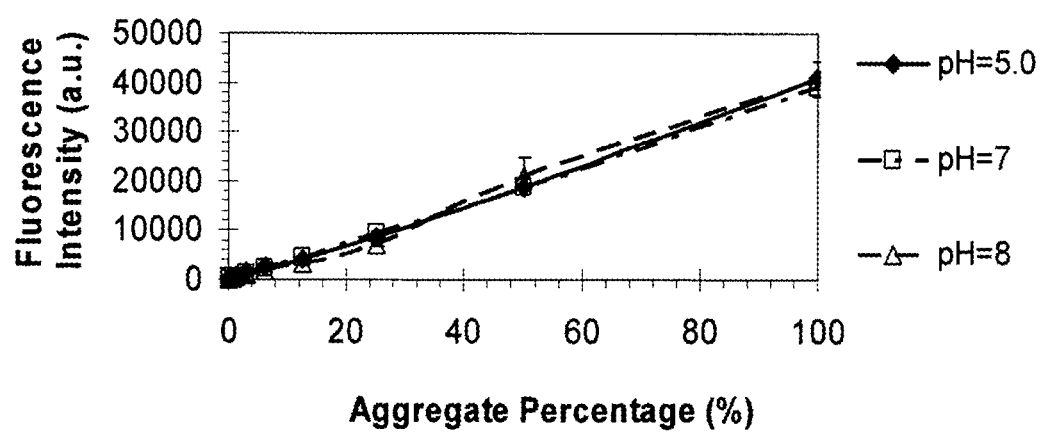

FIG. 5B. The effect of pH on the linearity of aggregation specific fluorescence was determined using 1.25 μM S-25 and 1.25 μM Tol3 in 50 mM of the following buffers: succinic acid-HCl, pH 5.0; Histidine-HCl, pH 7.0; and Tris-HCl, pH 8.0. The total concentration of lysozyme was kept constant at 20 μM, but the percent of the total that was aggregated as opposed to monomeric was varied from 0% to 100% aggregate. At least three replicates of each sample was prepared, incubated at 22° in the dark for 15 minutes, then scanned on a FLUOstar OPTIMA plate reader using an excitation wavelength of 550 nm and an emission of 610 nm.

Figure 6:
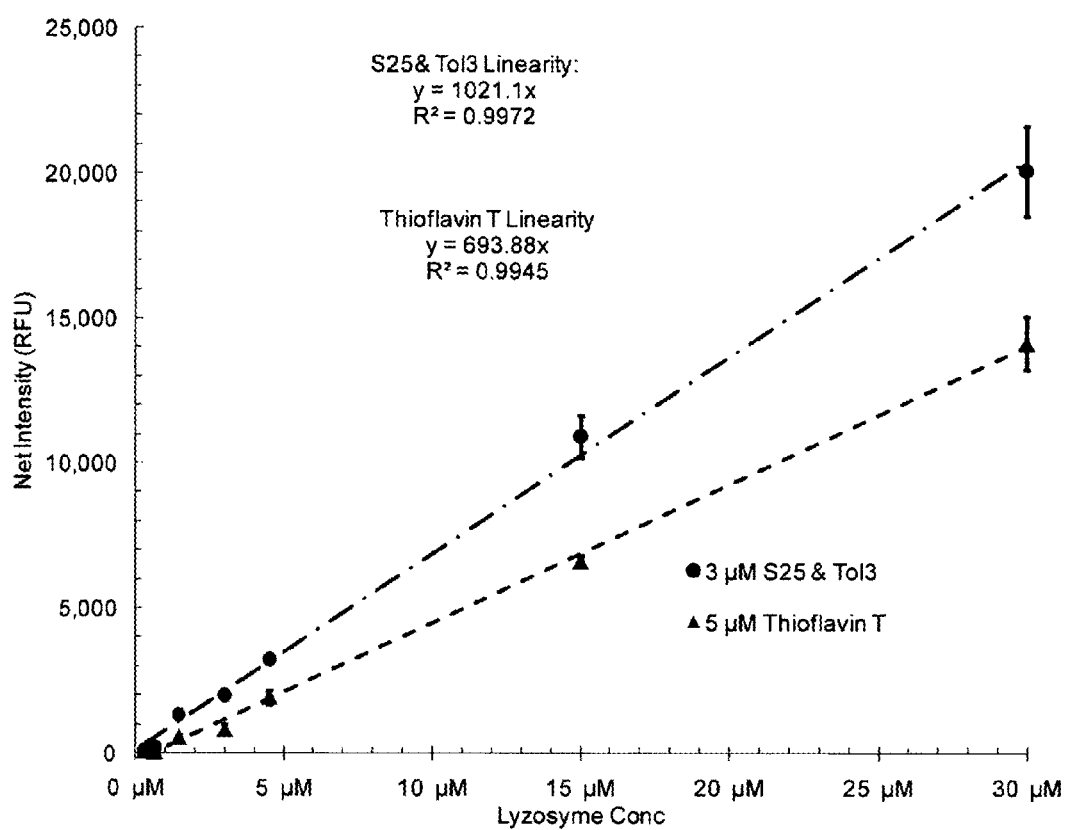
FIG. 6 shows the linear dynamic range of Lysozyme aggregate detection using a two dye combination ST (S25 and Tol3) compared with Thioflavin T.

Example 11 Linear Dynamic Range of Lysozyme Aggregate Detection Using a Two Dye Combination ST (525& Tol3) Compared with Thioflavin T Hen egg white lysozyme was solubilized in 10 mM HCl and heated to 65° C. for 90 hours to form aggregates. The signal from the aggregate was determined after mixing aggregated lysozyme with monomeric lysozyme at different ratios such that the total Lysozyme concentration remained at 20 µM protein. The readings were taken in 50 mM potassium phosphate, pH 7, containing either ST (3 µM S-25 and 3 µM Tol3) or 5 µM Thioflavin T. Protein was incubated with dye for 15 minutes prior to determining the fluorescence using a BioTek Synergy Mx plate scanner, with excitation setting at 515 nm and emission setting at 603 nm, both with a 9 nm slit-width for S-25 and Tol3, and Thioflavin T was detected with excitation setting at 435 nm and emission setting at 495 nm, both with a 9 nm slit-width. Readings were taken in at least triplicate in a Greiner pClear black, clear bottom 96-well microplate. As seen in FIG. 6 the concentration curve is more linear with S25/Tol3 as compared to Thioflavin T.

Figure 7:
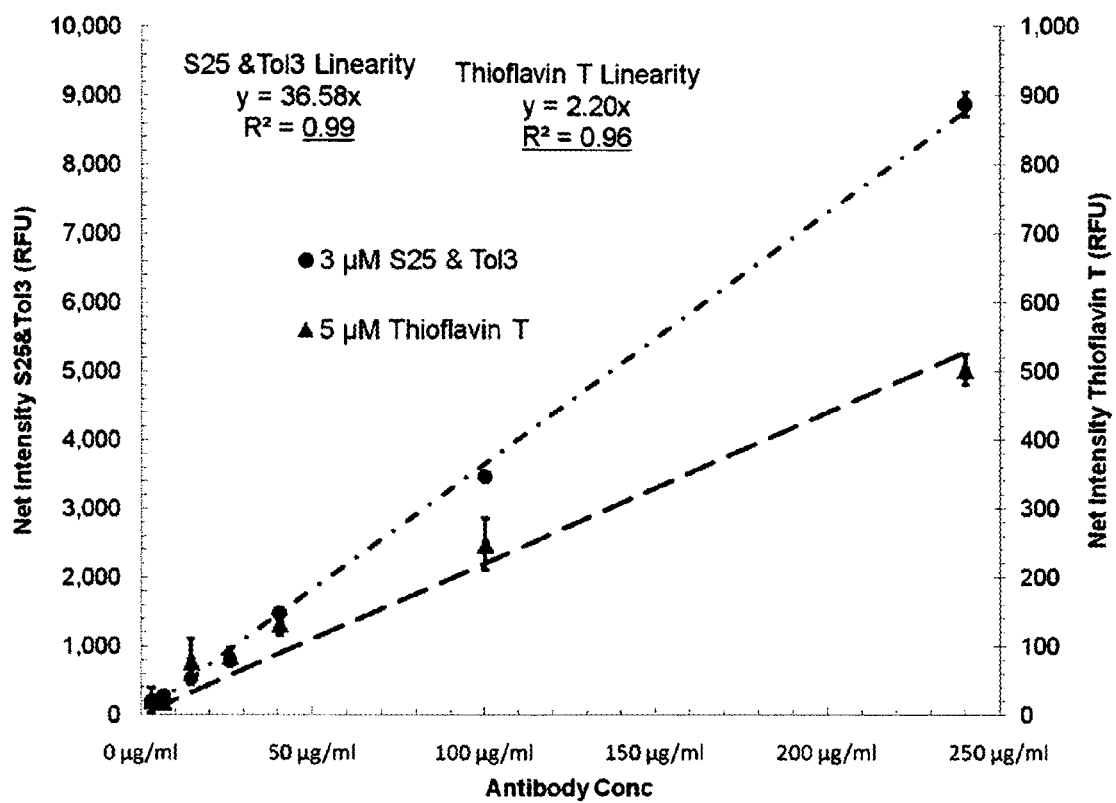
FIG. 7 shows the effective linear dynamic range of antibody aggregate detection using a two dye combination ST (S25 and Tol3) compared with Thioflavin T.

Example 12 Effective Linear Dynamic Range of Antibody Aggregate Detection Using a Two Dye Combination ST (S25& Tol3), Compared with Thioflavin T Purified Rabbit anti-Goat IgG (4,260 µg/ml) was incubated in HCl, pH 2.7 at 80° for 90 minutes to form aggregates. The signal from the aggregate was determined after mixing aggregate with monomer at different ratios such that the total IgG concentration remained 240 µg/ml protein. The readings were taken in 50 mM potassium phosphate, pH 7, containing either ST (3 µM S-25 and 3 µM Tol3) or 5 µM Thioflavin T. Protein was incubated with dye for 15 minutes prior to determining the fluorescence using a BioTek Synergy Mx plate scanner, with excitation setting at 515 nm and emission setting at 603 nm, both with a 9 nm slit-width for S-25 and Tol3, and Thioflavin T was detected with excitation setting at 435 nm and with emission setting at 495 nm, both with a 9 nm slit-width. Readings were taken in at least triplicate in a Greiner µClear black, clear bottom 96-well microplate. As can be seen in FIG. 7, the signal from ST is 10 times higher than the signal from Thioflavin T under these conditions. Also the concentration curve is more linear with S-25/Tol3 as compared to Thioflavin T. The scale for the Thioflavin T data is displayed on the right hand axis of the graph.

Example 13 Protein Aggregate Detection as a Function of Protein Species

The linearity of aggregation induced fluorescence of S-25, Tol3 and Thioflavin T (Thio-T) for four different proteins was determined (Hen egg white lysozyme (A), rabbit anti-goat IgG (B), Bovine insulin (C) and ß-lactoglobulin (D)).

Figure 8A:
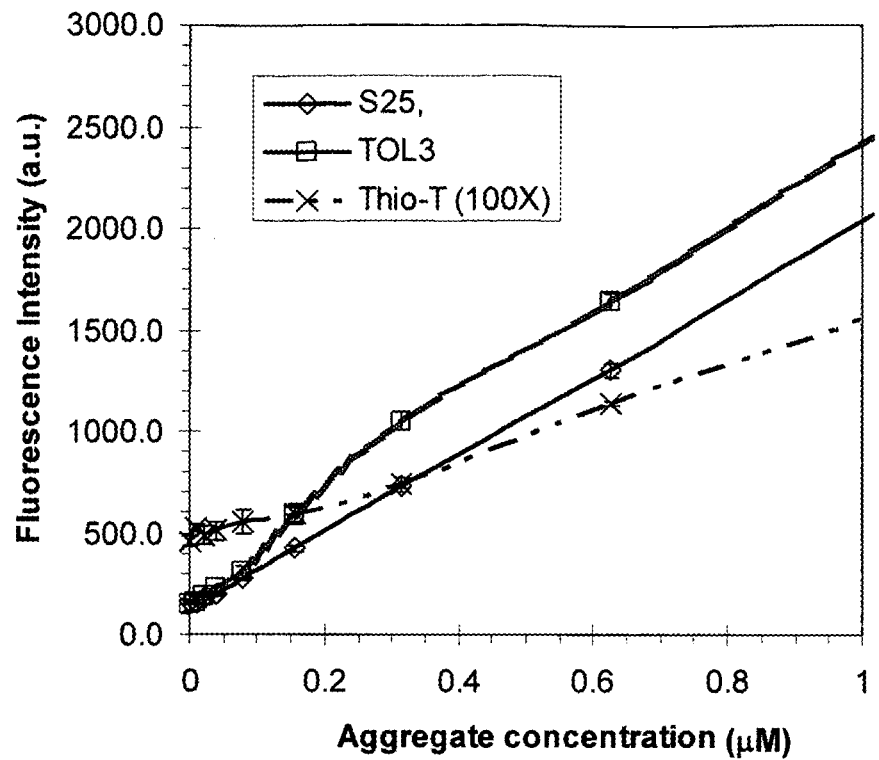
FIGS. 8A, 8B, 8C and 8D show protein aggregate detection as a function of various protein species with the dyes S25, Tol3 and Thioflavin T.

FIG. 8A. Chicken egg white lysozyme aggregate solution and monomer solution as well as their mixtures were prepared as described in Example 10. The protein concentration was maintained at 20 µM, and the dye concentration was 2.5 µM in 50 mM Tris-HCl, pH 8. The ratio of aggregated protein to native protein was varied from 0 to 100% aggregate. Each sample was analyzed in at least 3 replicates. The mixtures were incubated in the dark at 22° C. for 15 minutes, then the fluorescence intensity was determined with a FLUOstar OPTIMA plate reader (BMG LABTECH) with excitation setting at 550 nm and emission setting of 610 nm; while the fluorescence intensity for Thioflavin-T was determined using a SpectraMAX GeminiXS (Molecular Devices, with Softmax Pro 7.0) using an excitation wavelength of 435 nm and emission wavelength of 495 nm.

Figure 8B:
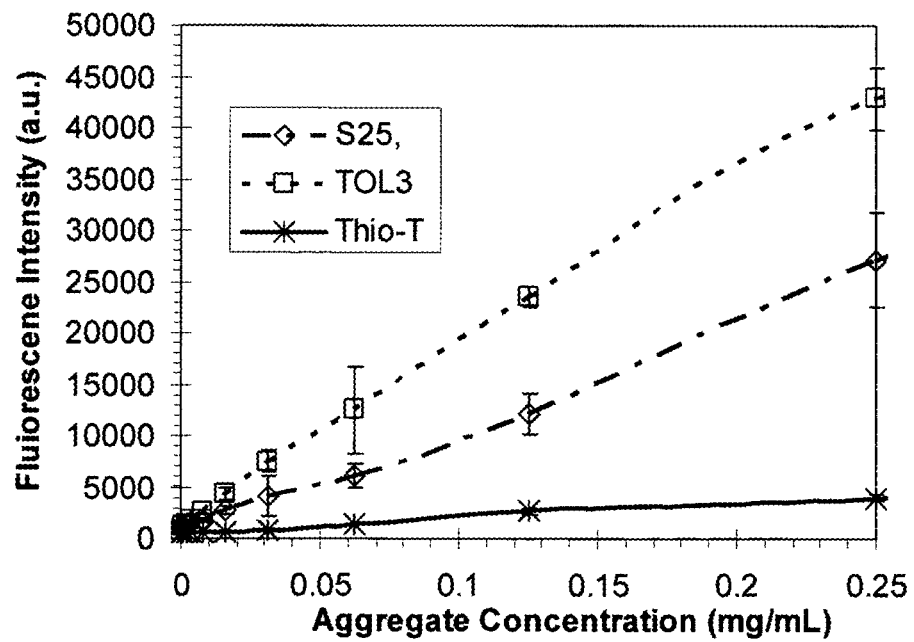

FIG. 8B. Rabbit-anti-goat IgG (H&L, Pel-Freez, formulated in the same manner as goat-anti-mouse IgG, described in table 2) was diluted to 29.4 µM with double deionized water adjusted to pH 2.7 using HCl. Then IgG aggregate was prepared by shaking the protein solutions at 750 rpm in a Thermomixer (Eppendorf) at 80° C. for 2 hours. Using a final protein concentration of 3 µM, the linearity of aggregation induced fluorescence was determined as described above for lysozyme.

Figure 8C:
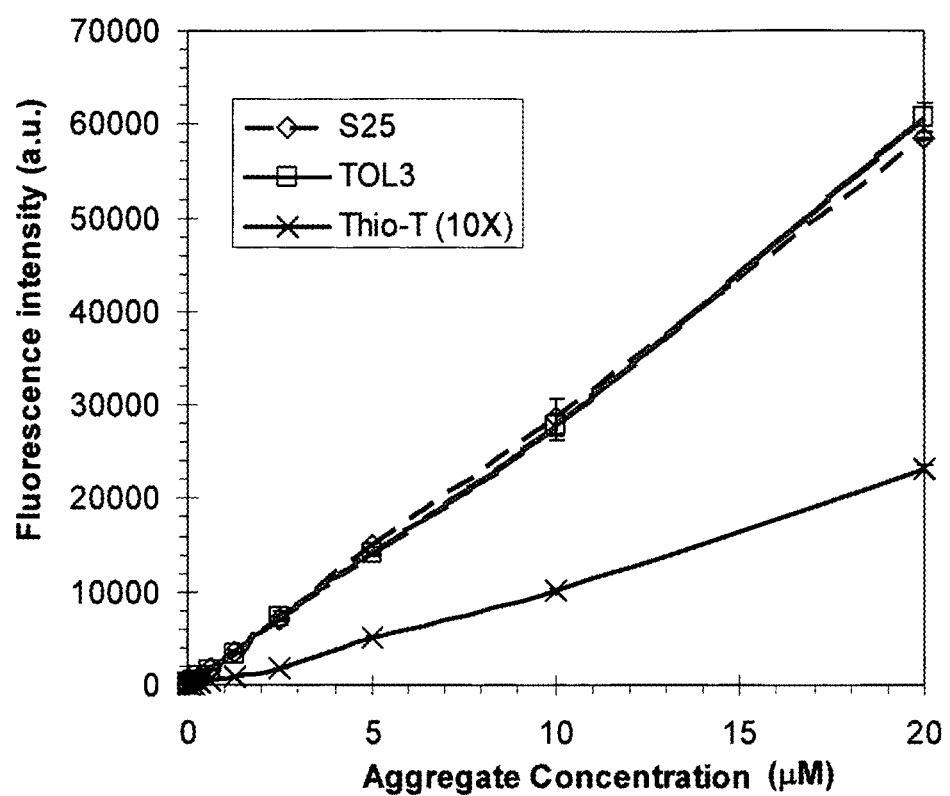

FIG. 8C. Insulin aggregate was prepared by dissolving bovine pancreas insulin (Sigma-Aldrich) at 170 µM in 100 mM HCl, which was subsequently transferred to a Thermomixer (Eppendorf), set at 750 rpm continuous shaking at 65° C. for 150 min. Using a final protein concentration of 20 µM, the linearity of aggregation induced fluorescence was determined as described above for lysozyme.

Figure 8D:
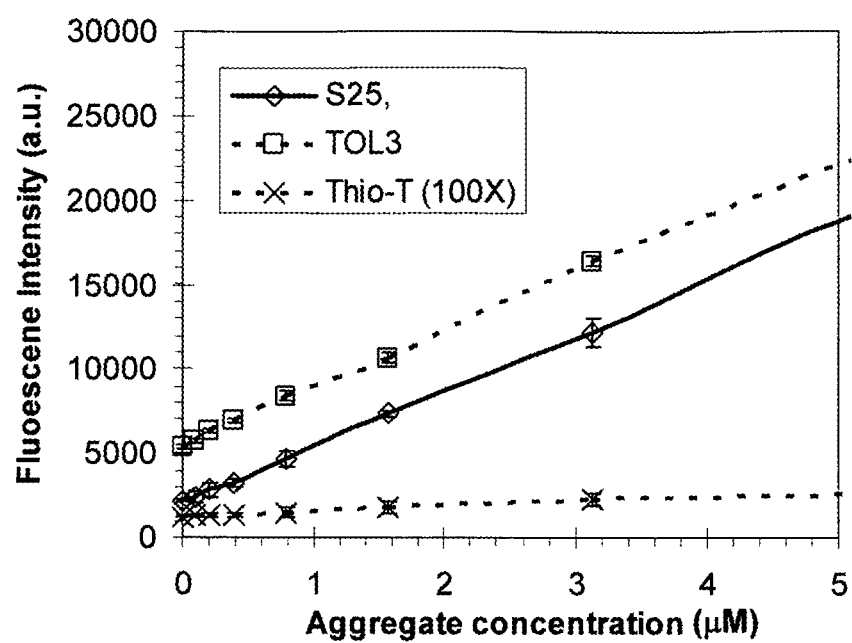

FIG. 8D. β-Lactoglobulin (BLG, Sigma-Aldrich) was dissolved at 1 mM in double deionized water. The aggregate was prepared by shaking the protein solutions at 750 rpm in a Thermomixer (Eppendorf) at 80° C., which was stopped after 24 hours. Using a final protein concentration of 50 µM, the linearity of aggregation induced fluorescence was determined as described above for lysozyme.

Example 14 Kinetics of Lysozyme Aggregation

Figure 9:
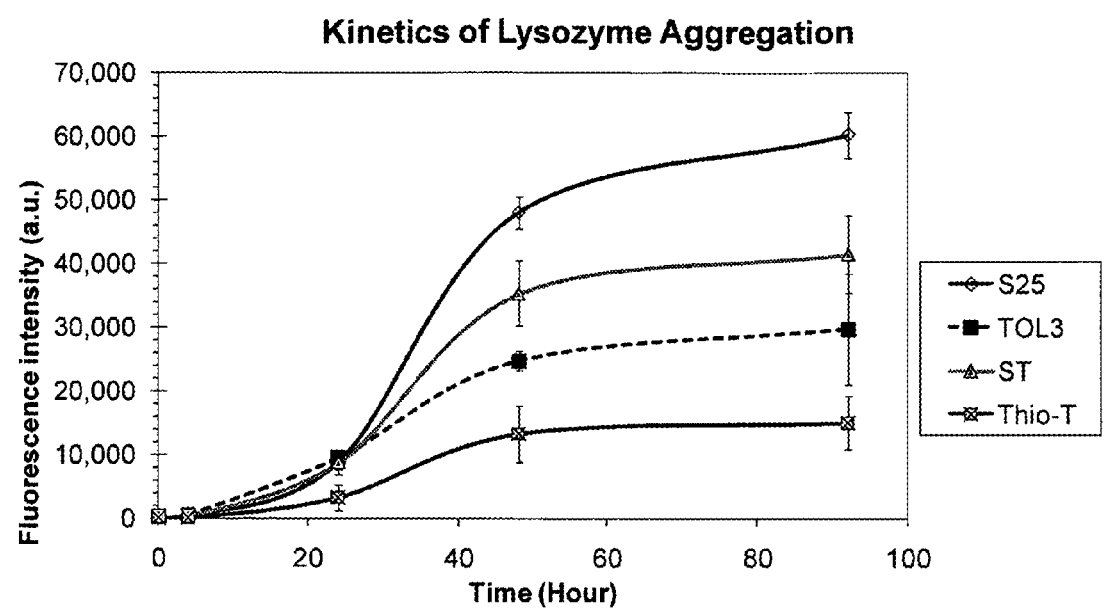
FIG. 9 shows the kinetics of Lysozyme aggregation monitored with dyes S25, Tol3, Thioflavin T and the two dye combination ST (S25 and Tol3).

A 1 mM solution of Hen Egg White Lysozyme in 10 mM HCl was incubated at 65° C. in an Eppendorf thermomixer shaking at 750 rpm. At the indicated times, aliquots of the Lysozyme were removed, diluted to 30 µM in 100 mM Tris-HCl, pH 8.0, and incubated with 5 µM of the indicated dye. After 15 minutes incubation, the fluorescent intensity was determined with a FLUOstar OPTIMA plate reader (BMG LABTECH) at excitation wavelength of 550 nm and emission wavelength of 610 nm; while the fluorescence intensity for Thioflavin-T was determined using a SpectraMAX GeminiXS (Molecular Devices, with Softmax Pro 7.0) using an excitation wavelength of 435 nm and emission wavelength of 495 nm. Every sample was evaluated in 4 replicates. As can be seen in FIG. 9, Tol3, S-25 and Thioflavin T all detect similar kinetics for protein aggregate formation.

Example 15 Protein Aggregation as a Function of Temperature

Figure 10:
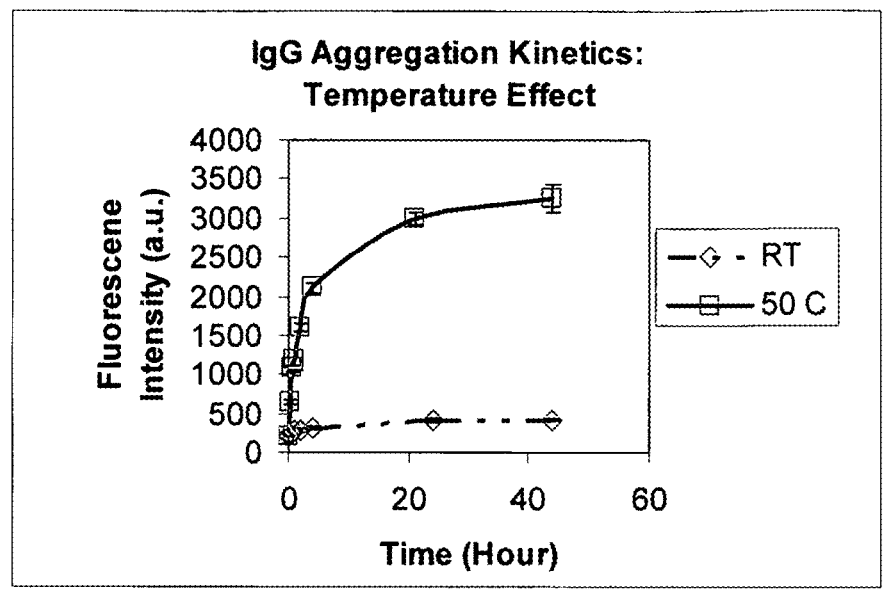
FIG. 10 shows the kinetics of IgG aggregation as a function of temperature.

A solution of Goat-anti-mouse IgG (Pel Freeze) of 0.9 mg/ml was made in 73 mM sodium acetate, pH 4.5. This solution was incubated at 21° C. or 50° C. for the indicated time. At the indicated time, this was diluted further to create a solution that was 50 mM Histidine, pH 7, 0.45 mg/ml IgG, 2.5 µM S-25 and 2.5 µM Tol3. After 15 minutes incubation the fluorescent intensity was determined with a FLUOstar OPTIMA plate reader (BMG LABTECH) at excitation wavelength of 550 nm and emission wavelength of 610 nm. As seen in FIG. 10, aggregation is much more rapid at 50° C. than at 21° C.

Example 16 Protein Aggregation as a Function of pH

Figure 11:
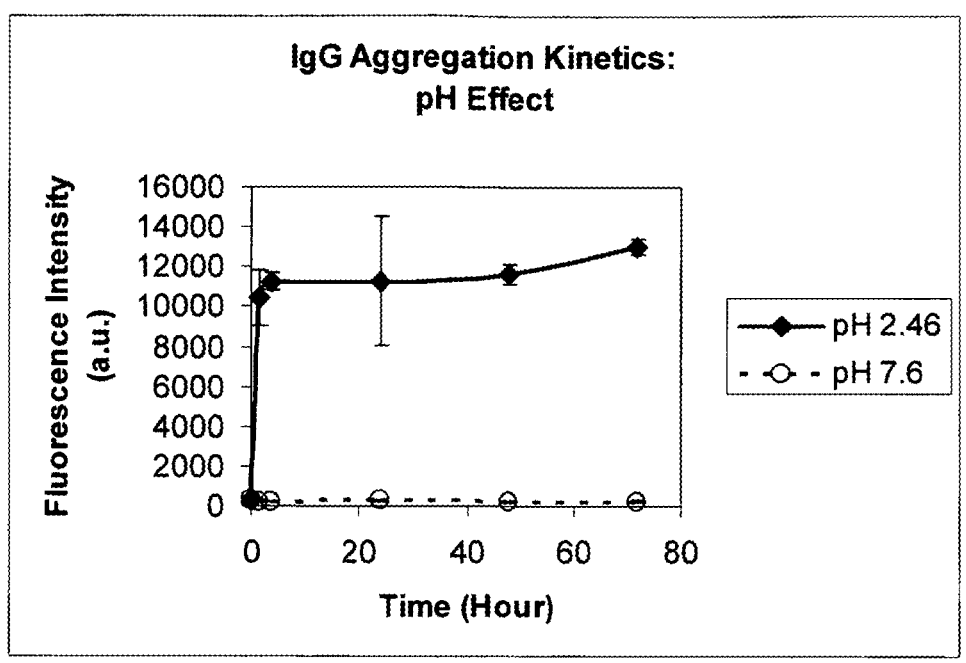
FIG. 11 shows IgG aggregation induced by temperature (50° C.) as a function of pH.

Goat-anti-mouse IgG was diluted to 40 µM at either pH 7.6 in sodium phosphate buffer, or adjusted to pH 2.46 using HCl. Both solutions were then kept at 21°. After the indicated time, aliquots were removed and diluted to a final concentration of 2 µM in 100 mM histidine buffer, pH 7 with 2.5 µM S-25 and 2.5 µM Tol3. After 15 minutes of incubation at 21° C., the fluorescence intensity was recorded. As seen in FIG. 11, aggregation is observed to be much more rapid under acidic pH conditions.

Figure 12A:
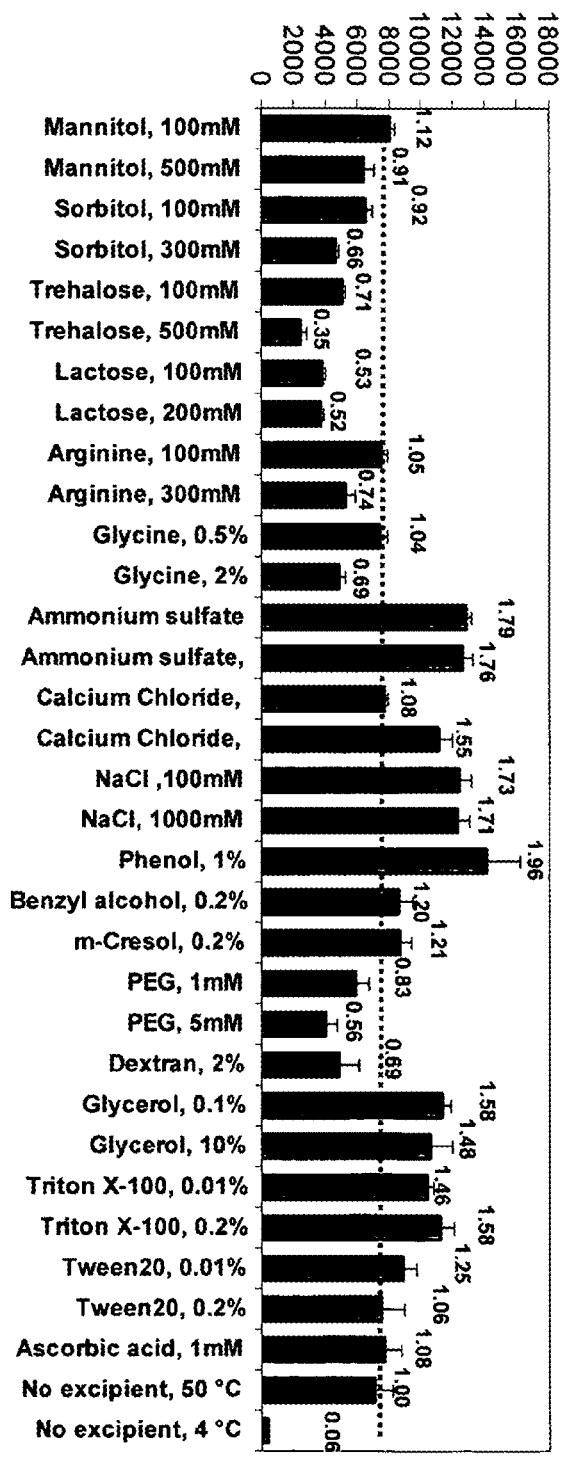
FIGS. 12A, 12B and 12C are illustrations of a high-throughput protein formulation optimization workflow using IgG and the two dye combination ST (S25 and Tol3).

Example 17 Illustration of High-Throughput Protein Formulation Optimization (A). Goat anti-mouse IgG was diluted in sodium acetate, pH 4.5, then mixed with the excipients shown in FIG. 10 A giving a final concentration of 400 mM sodium acetate, 18 µM IgG and the excipient concentration shown in the Table 2. This mixture was heated to 50° C. for 6 hours. At this time the protein solution was diluted two-fold to give a final concentration of 50 mM Histidine buffer, originally pH 7, 2.5 µM S-25, 2.5 µM Tol3 and 9 µM IgG. After 30 minutes of incubation on the shaker, the fluorescence intensity was recorded on the plate reader (FLUOstar Optima). The fluorescence intensity from each individual excipient was then compared with that without any excipient (Value set as 1.0) as shown on the top of the corresponding excipient bar in FIG. 12 A.

(B). In the control plate, the IgG was added to the plate, at the same volume and concentration given above (Example 17A) in 400 mM Sodium Acetate. This mixture was heated to 50° C. for 6 hours, as described above. After 6 hours, the excipient was added followed by S-25 and Tol3 to give all the final concentrations as shown in Example 17A. Similar to the sample plate, the fluorescence intensity from individual excipients was also compared with that from water without any excipient (Values set as 1.0) to obtain the relative fluorescent intensity as shown on the top of the corresponding excipient bar in FIG. 12B.

Figure 12B:
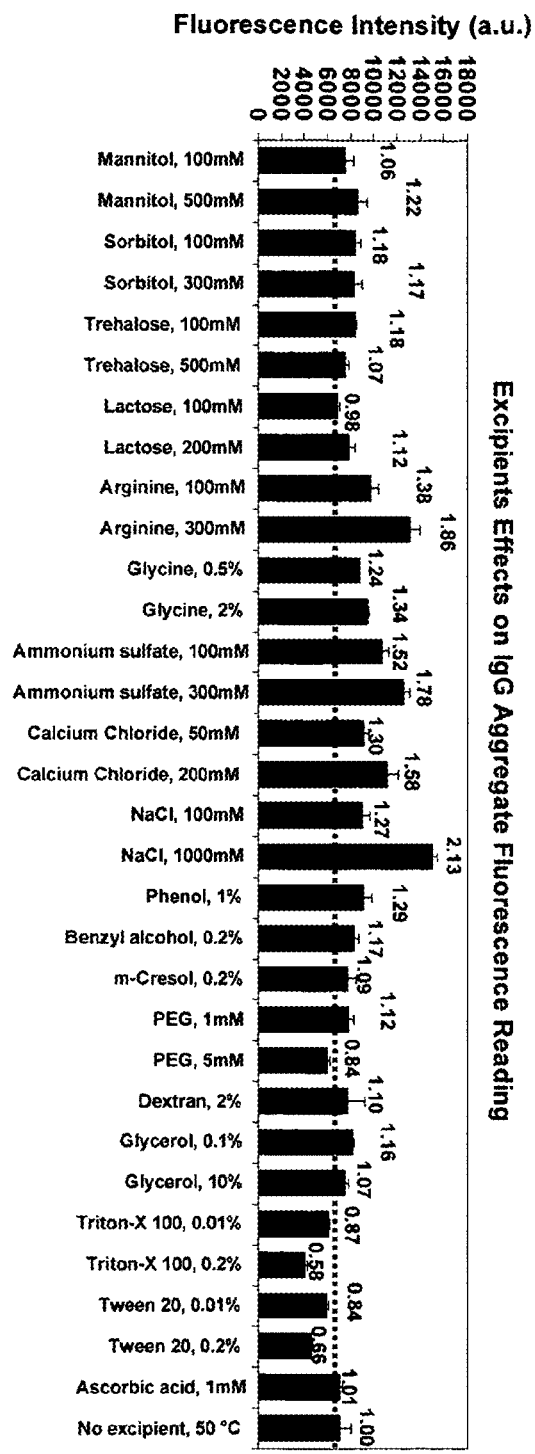
Figure 12C:
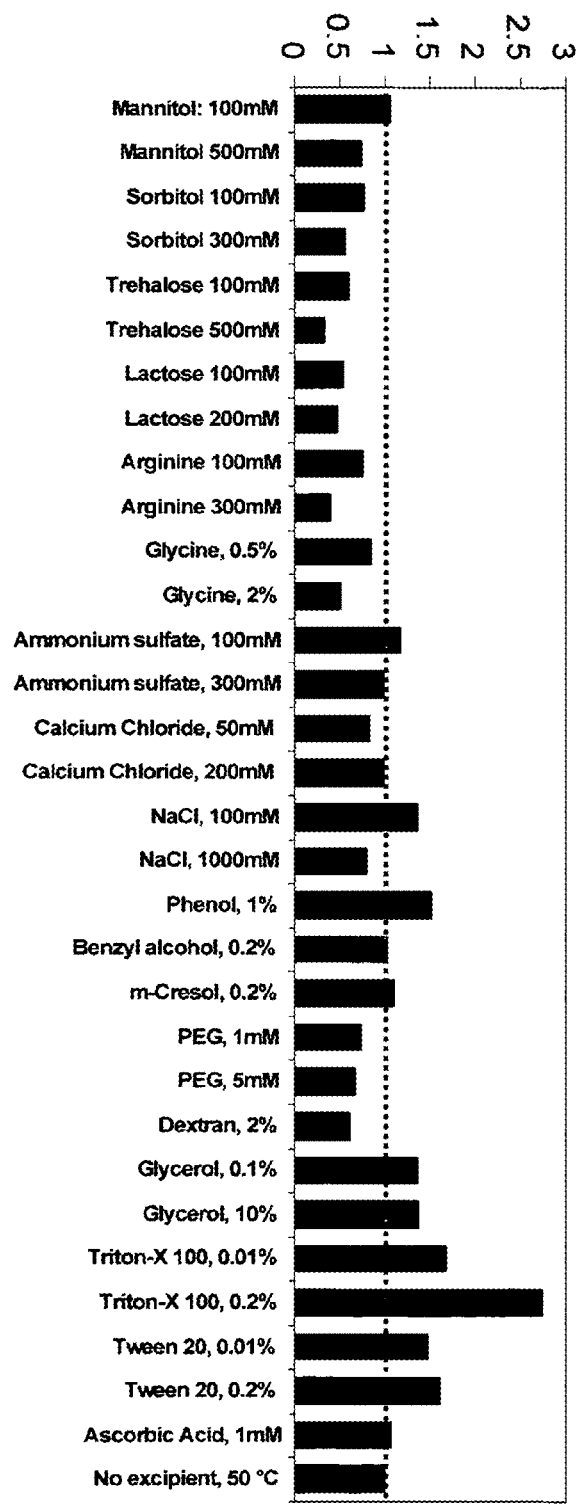

(C). A ratio between the fluorescent intensity of the protein aggregated with the excipient versus the intensity derived from the protein aggregated without excipient is a good measure of the effect of the given excipient on aggregation. FIG. 12C shows the ratio of fluorescence intensity in the sample plate (FIG. 12 A) divided by the fluorescence intensity of the control plate (FIG. 12B). Those compounds with a value of 1 (dotted line) do not significantly affect aggregation of IgG. Those compounds substantially higher than 1, such as 0.2% Triton X-100 induce aggregation of IgG. Those compounds with a value substantially lower than 1, such as 100 mM Trehalose inhibit or slow down aggregation of IgG.

Example 18 Inhibition of Lysozyme Aggregation by Chitotriose

Figure 13:
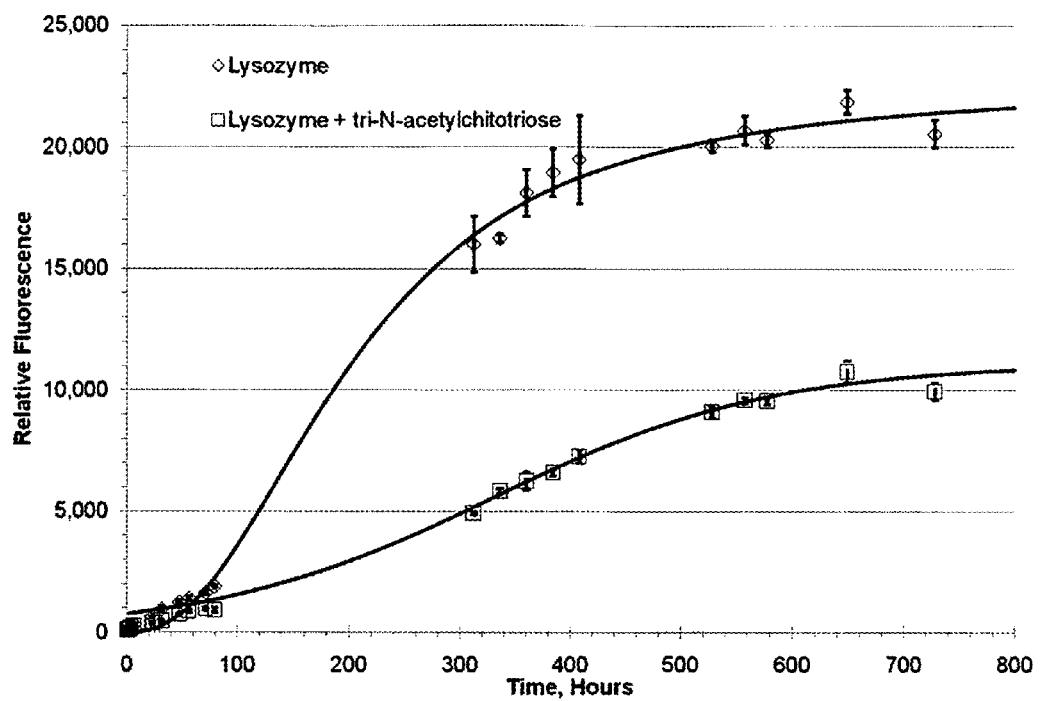
FIG. 13 shows measurement of the inhibition of Lysozyme aggregation by Chitotriose.

Hen egg white Lysozyme (300 µM) was incubated with or without N,N',N"-triacetyl-chitotriose (Chitotriose, 510 µM) in 10 mM potassium phosphate, pH 7.3 for 16 hours. Aggregation was induced by 3.5 fold dilution into 50 mM potassium phosphate, pH 12.2. Aggregation was followed by removing an aliquot of the protein and diluting such that the final composition was 20 µM protein, 50 mM potassium phosphate, pH 7, 3 µM S-25 and 3 µM Tol3. Protein was incubated with dye for 15 minutes prior to determining the fluorescence using a BioTek Synergy Mx plate scanner, with excitation setting at 515 nm and emission setting at 603 nm, both with a 9 nm slit-width. The zero time point was taken before dilution to pH 12.2. Readings were taken in at least triplicate in a Greiner µClear black, clear bottom 96-well microplate. Aggregation was followed for several weeks at room temperature (19°-23° C.). As seen in FIG. 13, S-25 and Tol3 easily demonstrate that Chitotriose inhibits Lysozyme aggregation, as previously demonstrated by Kumar et al. (2009) [Satish Kumar, Vijay Kumar Ravi and Rajaram Swaminanthan, "Suppression of Lysozyme aggregation at alkaline pH by tri-N-acetyl-chitotriose" Biochimica et Biophysica Acta 1294, 913-920 (2009)].

Example 19 Thermal Shift Assays of BLG Aggregation

Figure 14:
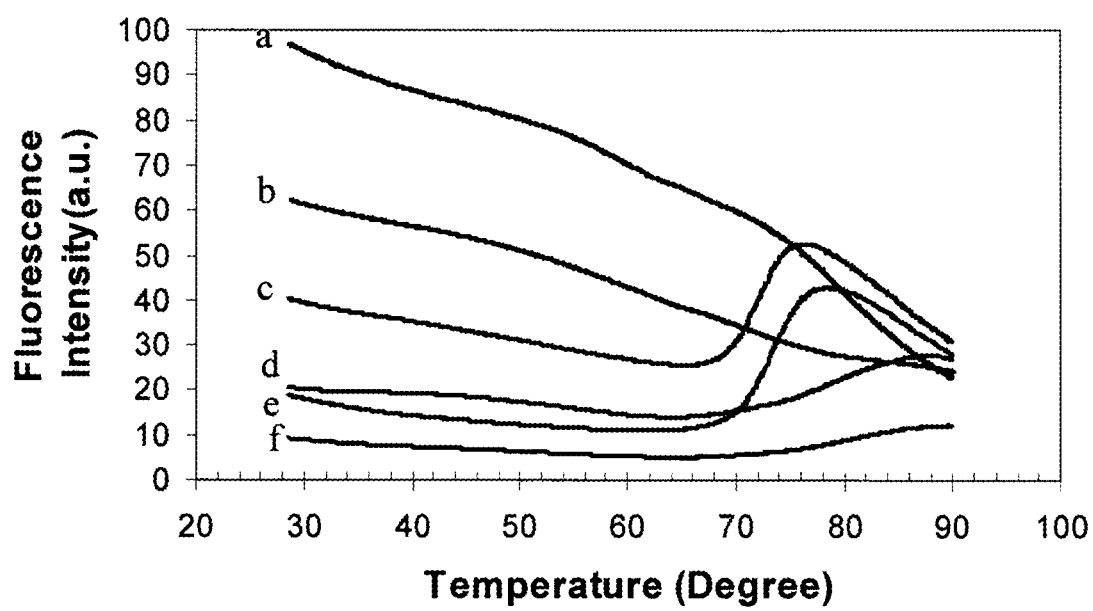
FIG. 14 shows a thermal shift assay of BLG aggregation using a dye of the present invention.

A solution containing 4 or 16 mg/mL of β-lactoglobulin (BLG) and 2×SYPRO® Orange dye (Molecular Probes, supplied as 5000× with unknown concentration) or 4 µM TOL3 or 4 µM S25 was prepared using 1×PBS, pH 7.4 as the dilution buffer. This solution was then loaded into LightCycler® capillaries (20 µL, Roche Diagnostics GmbH). These capillaries were then mounted on the sample holder of a LightCycler® 480 Real-Time PCR System (Roche), programmed to heat from 28° C. to 90° C. at 3° C./min, followed by cooling down to 28° C. at the same rate. The thermal shift curves were achieved by plotting fluorescence intensity vs. temperature. After the heating cycle, protein aggregates were visually apparent. However, SYPRO® Orange dye, known to detect protein, failed to show a melting peak, probably because of a low binding affinity to the aggregated BLG; but both TOL3 and S25 were able to detect BLG thermal shift peaks due to the aggregation, as shown in FIG. 14. The temperature of aggregation detected by TOL3 or S25 both showed a protein concentration dependence, down-shifting from 81~83° C. to 71~73° C. when the BLG concentration was increased from 4 mg/mL to 16 mg/mL, a characteristic of protein aggregation, as opposed to protein unfolding. This demonstrates that both TOl3 and S25 are detecting aggregation thermal shift peaks of BLG, not transitions do to unfolding of the protein.

Example 20 Thermal Shift Assays of Carbonic Anhydrase II Aggregation

Figure 15A:
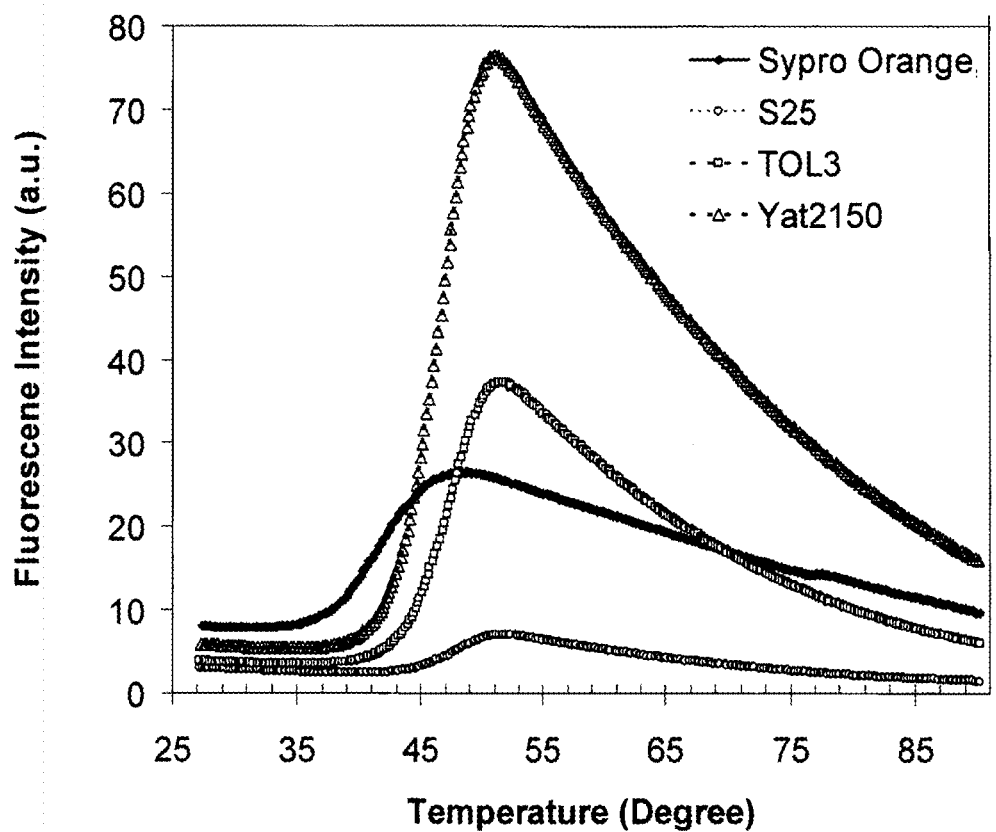
FIGS. 15A and 15B show a thermal shift assay of carbonic anhydrase II aggregation at two different pH values using a dye of the present invention.
Figure 15B:
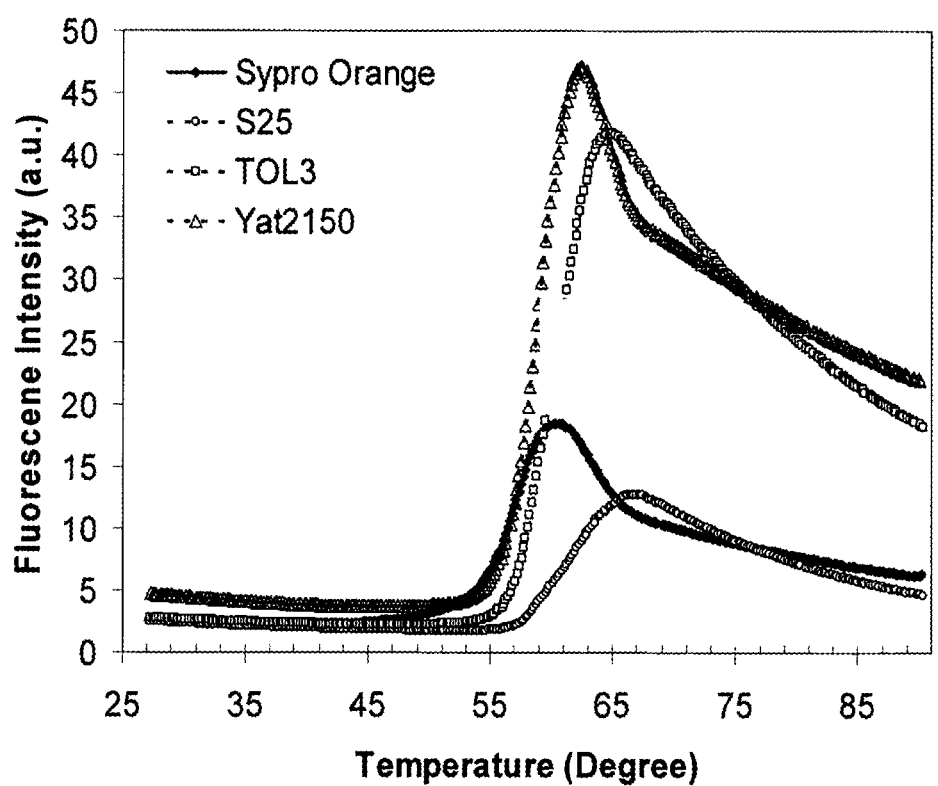

Carbonic anhydrase II (Sigma, 10 µM) containing 5×SYPRO® Orange or 10 µM TOL3 or S25 or Yat 2150 was prepared using either 50 mM sodium acetate, pH 4.5 or 25 mM PIPES, pH 7.0 buffer containing 100 mM NaCl and 0.5 mM EDTA. Then, sample preparation and the thermal shift assay were performed using the same conditions as described in Example 19. As shown in FIG. 15, although SYPRO® orange and dyes of the invention all show thermal shift peaks, there is a ~5° C. up-shift for peaks from dyes of the invention, between pH 4.5 and pH 7.0. This also highlights the fundamentally different detection mechanism between SYPRO® Orange dye and the dyes described in this invention; the former is detecting protein unfolding, while the later are detecting protein aggregation.

Example 21 Comparison of Fluorescence Response Between Unfolded and Aggregated Form of IgG Using Dyes of the Present Invention (A) Chemical shift assay based on internal tryptophan fluorescence: Rabbit-anti-goat IgG (Pel Freeze) in 1×PBS buffer of pH 7.4 was mixed with urea in 1×PBS to achieve a final IgG concentration of 0.25 mg/mL. After mixing on ice for 10 minutes, the fluorescence emission intensity at 330 nm was recorded by exciting at 280 nm using a MD-5020 fluorimeter (Phototechnology International). A chemical shift curve was plotted based on internal tryptophan fluorescence intensity at each given urea concentration. Urea denatures proteins but prevents them from aggregating.

Figure 16A:
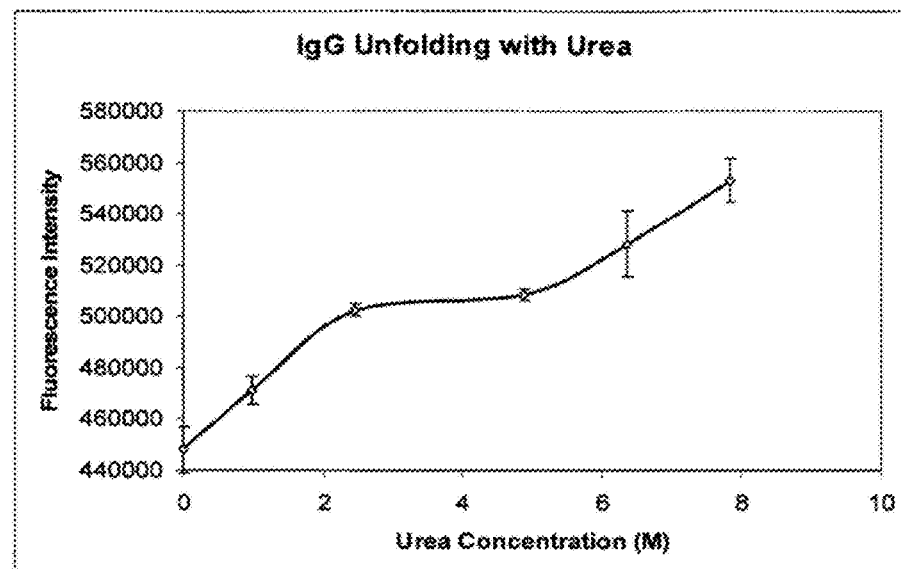
FIGS. 16A and 16B compare the fluorescence response between unfolded and aggregated forms of IgG.
Figure 16B:
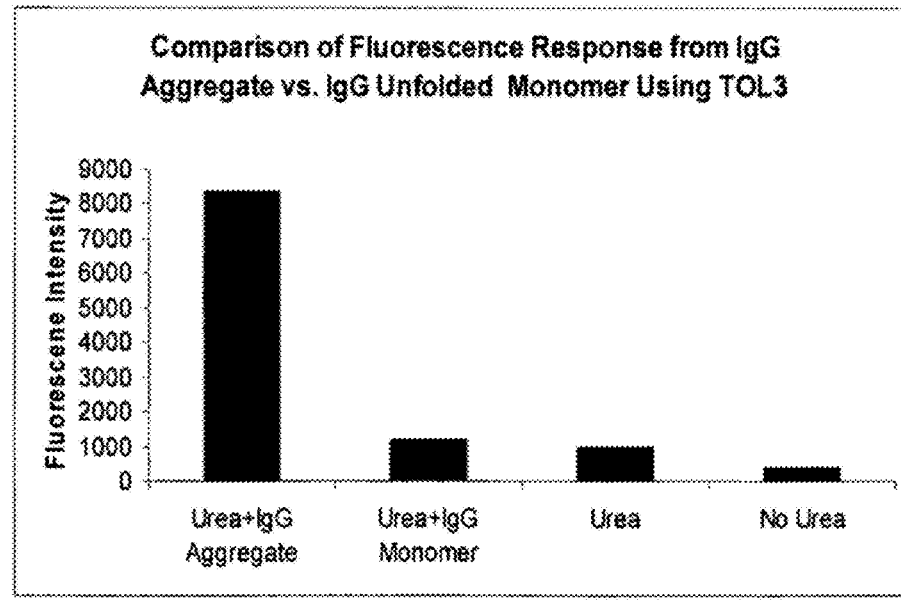

(B) A solution containing aggregated IgG (formed as in Example 13 (B)) or monomeric IgG at 0.033 mg/mL, 4.55 M urea and 6.67 µM Tol3 was prepared and transferred into a microplate. After incubating at 4° C. degree for about 10 minutes, the fluorescence was recorded. Two control solutions without IgG, but with the same concentration of TOl3, were included, one including 4.55M urea, another without urea. From the previous chemical shift curve generated (seen in FIG. 16 (A)), 4.55 M urea is known to unfold approximately 60% of the IgG. The results shown in FIG. 16 (B) indicate that TOL3 is sensitive to IgG aggregates, which shows significant fluorescence enhancement relative to controls without IgG, but it is not sensitive to unfolded IgG monomer, which shows insignificant fluorescence enhancement relative to controls without IgG.

Figure 17A:
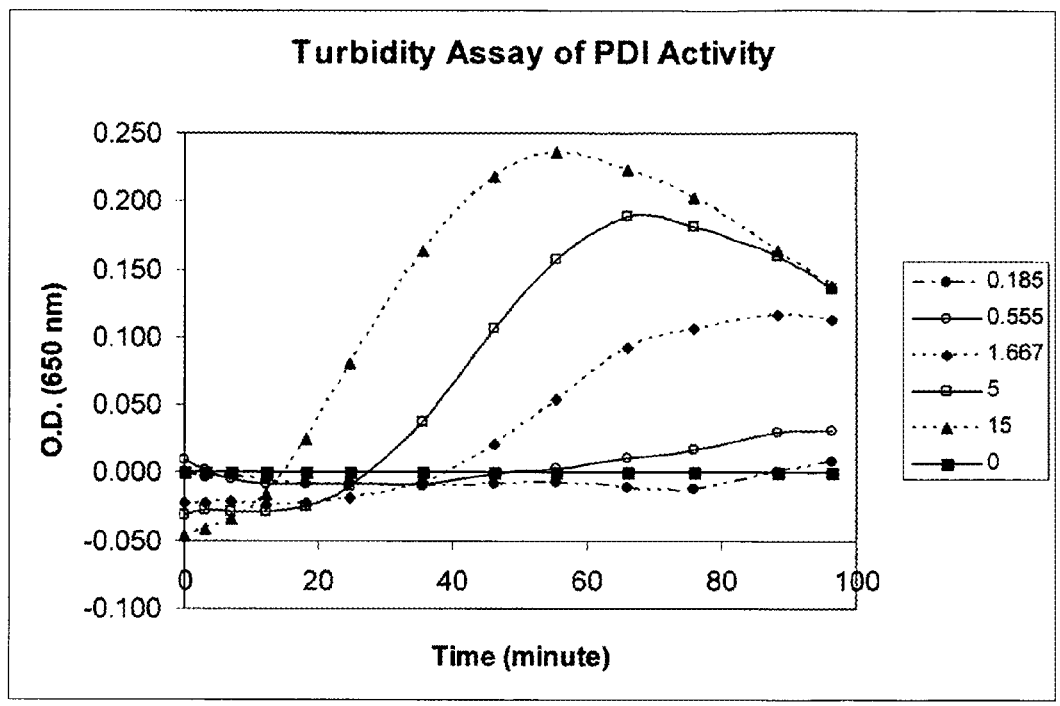
FIGS. 17A, 17B and 17C show PDI activity monitored by turbidity and by a fluorometric assay using a dye of the present invention.
Figure 17B:
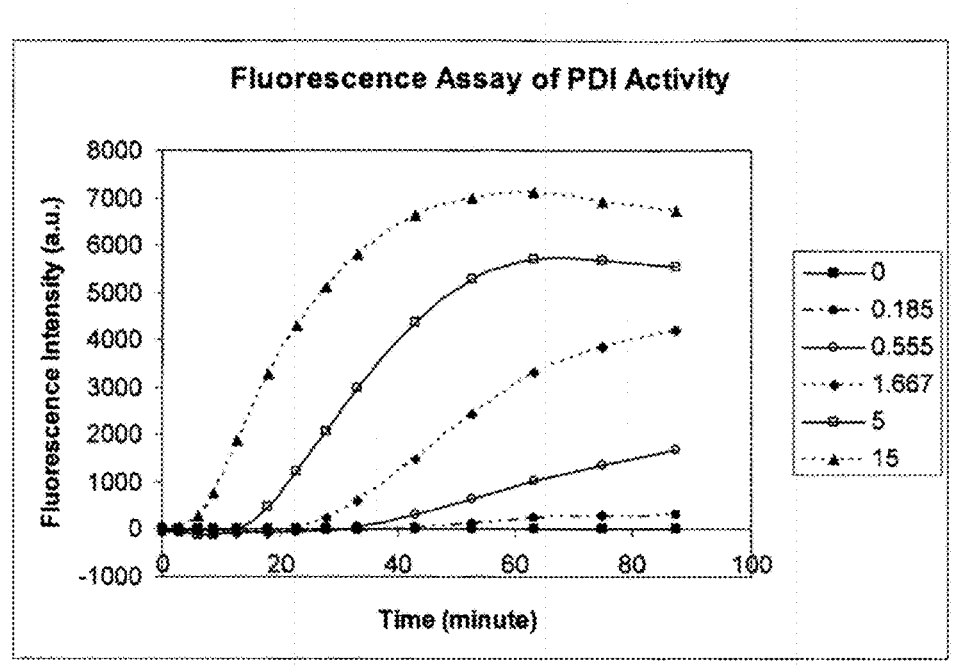
Figure 17C:
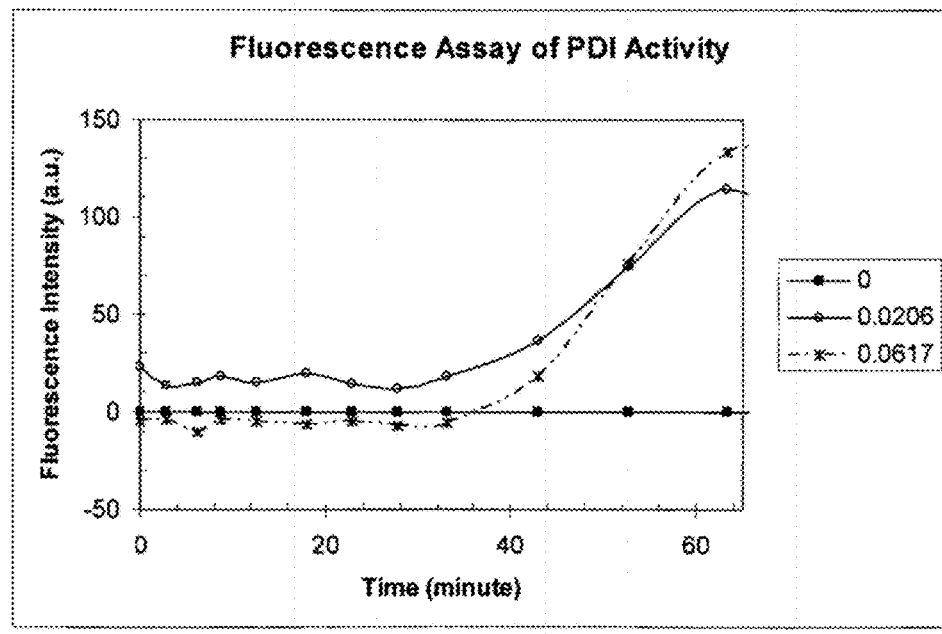

Example 22 PDI Isomerase Activity Assay by Monitoring Insulin Aggregation Kinetics (A) Turbidity assay: Protein Disulfide Isomerase (PDI, Assay Designs) was diluted with 0.5M of sodium phosphate, pH 6.8. A mixture was made with insulin to give a final solution comprising 188 mM Sodium phosphate, pH 6.8, 5 mM TrisHCl, 2 mM EDTA, 1 mM DTT, 1 mg/mL insulin and PDI at the desired concentrations (0, 5, 10, 15, 20, 25 µg/mL). The optical density (OD) at 630 nm was recorded immediately after the addition of DTT in a 96-well microplate reader at 2 minute-intervals, with every well containing 300 µL solution. The OD from 0 µg/mL of PDI at any time point was used as a background value and was subtracted from the OD value of samples with PDI at the same time point. Results are seen in FIG. 17 A.

(B) Fluorometric assay: PDI and insulin solutions were prepared as the turbidity assay above. S25 and TOL3 were mixed with the insulin solution and placed into a black Greiner 96-well plate with flat bottom. PDI solutions containing various amount of PDI were then added. Just prior to fluorescence recording, DTT was added. The final solution was 188 mM Sodium phosphate, pH 6.8, 5 mM Tris-HCl, 2 mM EDTA, 1 mM DTT, 0.225 mg/mL insulin and PDI at 0, 5, 10, 20 µg/mL. A FLUOstar Optima plate reader was used to record the fluorescence change after 5 seconds' shaking with excitation set at 550 nm and emission set at 610 nm. The fluorescence intensity from 0 µg/mL of PDI solution at the corresponding time point was used as a background value and was subtracted from the corresponding reading in the presence of enzyme. Results are seen in FIG. 17B. The turbidity assay and fluorometric assay, though of significantly different sensitivities, are orthogonal to each other, further supporting that dyes of the present invention monitor aggregation status and not unfolding status.

Example 23

Figure 18:
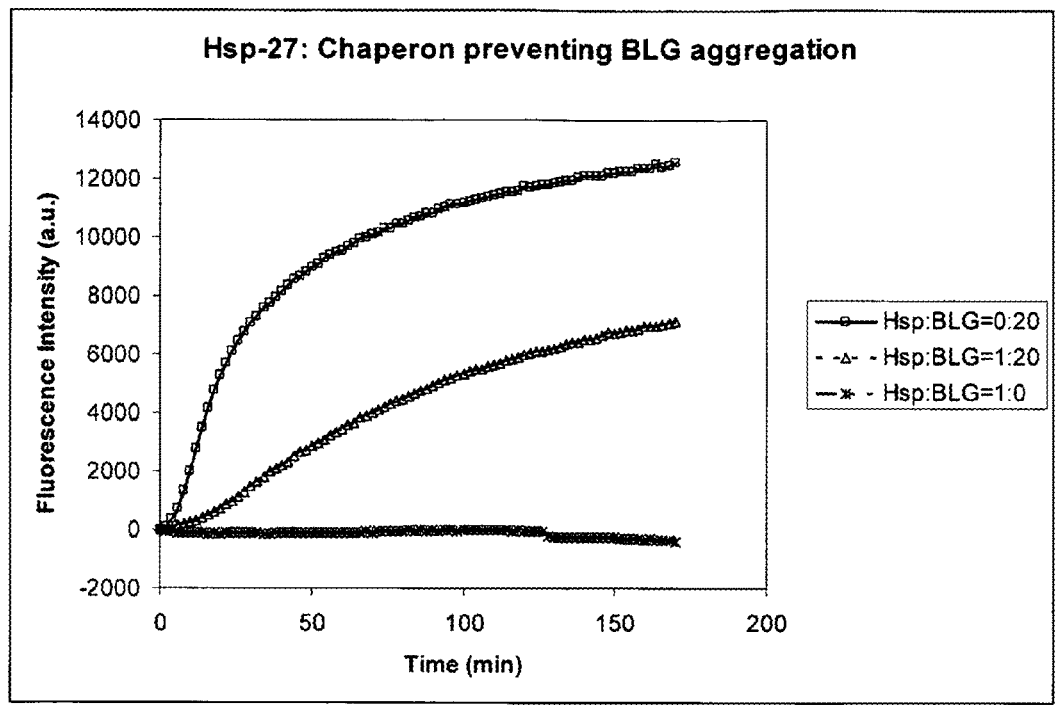
FIG. 18 shows activity assay of Hsp 27 (heat shock protein) as a chaperone preventing β-Lactoglobulin (BLG) aggregation induced by heat.

Aggregation of ß-lactoglobulin was monitored in the presence or absence of the chaperone HSP 27. Aggregation of 8 mg/ml ß-lactoglobulin was monitored using 1.25 µM Tol3 and 1.25 µM S25 in PBS, pH 7.4 with 2.5 mM EDTA and 0.05% sodium azide. When the chaperone HSP 27 was added it was added to a final concentration of 0.4 mg/ml. HSP 27 was also run in the absence of R-lactoglobulin as a control. Aggregation was initiated by heating the protein solution to 68° C. in a 96 well half-volume clear plate (Biomol international, Inc). The fluorescence intensity was then recorded every 2 minutes, with shaking between reads. The excitation wavelength was set to 550 nm and the emission was set to 610 nm on a BMG Fluorstar plate reader. The fluorescence intensity of the starting point was subtracted from the remaining points. The results (FIG. 18) indicate that Hsp 27 can significantly prevent the aggregation of BLG at a mass ratio as low as 1:20. Since Hsp 27 is binding with unfolded BLG intermediate, thus preventing protein aggregation, these styryl cyanine dyes are detecting protein aggregation, as opposed to unfolding.

Other chaperone activity assays can be configured using R-lactoglobulin or other substrates, such as citrate synthase (CS). Below is provided a table with suggestions for chaperone-to-CS ratios that should find application for the disclosed assay methods.

| Chaperone system | Members | ADI catalog #s | Chaperone:CS |
|---|---|---|---|
| DnaK/DnaJ/GrpE | DnaK | SPP-630 | 1:1 or less |
| | DnaJ | SPP-640 | |
| | GrpE | SPP-650 | |
| Hsp70/Hsp40 | Hsp70 | NSP-555, ESP-555, SPP-758 | 1:1 or less |
| | Hdj1 | SPP-400 | |
| | Hdj2 | SPP-405 | |
| | Mortalin | SPP-828 | |
| | Hsc70 | SPP-751 | |
| | Hsp70-A1 | SPP-502, ESP-502 | |
| Hsp90 | Hsp90 alpha | SPP-776 | Depends on cochaperones |
| | Hsp90 beta | SPP-777 | |
| Chaperonins (human) | Hsp60/Cpn10 | NSP-540, ESP-540 | 1:1 or less |
| | Cpn10 | SPP-110 | |
| Chaperonins (bacterial) | GroEL | SPP-610 | 1:1 or less |
| | GroES | SPP-620 | |
| Small heat shock proteins | Hsp25 | SPP-510 | 20:01 |
| | Hsp27 | SPP-715, SPP-716 | |
| | Crystallins | SPP-225, SPP-226, SPP-235, SPP-236 | |
| ER the chaperones | Grp78 | SPP-765 | 5:1 |
| | PDI | SPP-891 | 10:1 |
| | Erp72 | H00009601-Q01 (abnova) | 20:1 |
| | Grp94 (ER Hsp90) | SPP-766 | Depends on cochaperones |
| Nascent chain chaperones | NAC | none | 20:1 |
| | Trigger Factor | none | 20:1 |

Chaperone: CS ratios are based upon the known biology of the individual systems. Active folders are likely to show significant signal at less than 1:1 molar ratio to substrate, as each chaperone complement will be able to inhibit aggregation while it actively folds. Aggregate inhibitors like the small heat shocks and trigger factor require substantially more, as they need to saturate the solution to prevent aggregation. Pairs of holders and folders (e.g., crystalline with low Hsp70 complex) may provide synergistic effects.

What is claimed is:

1. The dye TOL-11.
2. The dye TOL-2.
3. The dye TOL-6.
4. A kit comprising one or more dyes selected from the group consisting of TOL-11, TOL-2, and TOL-6.
5. The kit of claim 4, further comprising a dye selected from the group consisting of S-43, S13, S-39, and S-42.
6. The kit of claim 4, further comprising a dye selected from the group consisting of YAT-2134, YAT-2148, YAT-2149, YAT-2150, YAT-2135, YAT-2214, YAT-2213, and YAT-2324.
7. The kit of claim 4, comprising more than one dye selected from the group consisting TOL-11, TOL-2, and TOL-6.

* * * * *